United States Patent
Kazman et al.

(10) Patent No.: US 12,329,861 B2
(45) Date of Patent: Jun. 17, 2025

(54) TRANSDERMAL DRUG DELIVERY SYSTEM AND USES THEREOF

(71) Applicant: Ategenos Pharmaceuticals Inc., Cambridge, MA (US)

(72) Inventors: William Kazman, Westford, MA (US); Donald DeGolyer, Kiawah Island, SC (US); Darren Leo Miller, Westford, MA (US)

(73) Assignee: ATEGENOS PHARMACEUTICALS INC., Cambridge, MA (US)

( * ) Notice: Subject to any disclaimer, the term of this patent is extended or adjusted under 35 U.S.C. 154(b) by 0 days.

(21) Appl. No.: 18/674,321

(22) Filed: May 24, 2024

(65) Prior Publication Data
US 2024/0390288 A1    Nov. 28, 2024

Related U.S. Application Data

(63) Continuation of application No. PCT/US2024/031005, filed on May 24, 2024.
(Continued)

(51) Int. Cl.
*A61K 9/70* (2006.01)
*A61K 9/00* (2006.01)
(Continued)

(52) U.S. Cl.
CPC .......... *A61K 9/7038* (2013.01); *A61K 9/0009* (2013.01); *A61M 35/10* (2019.05);
(Continued)

(58) Field of Classification Search
CPC .............. A61M 35/10; A61M 2205/14; A61M 2205/3306; A61M 2205/3327;
(Continued)

(56) References Cited

U.S. PATENT DOCUMENTS 7,969,307 B2    6/2011    Peeters
8,077,042 B2    12/2011    Peeters
(Continued)

FOREIGN PATENT DOCUMENTS

WO    WO-2019090125 A2    5/2019
WO    WO-2021037653 A1    3/2021

OTHER PUBLICATIONS

PCT/US2024/031005 International Search Report and Written Opinion dated Oct. 30, 2024.

*Primary Examiner* — Andrew J Mensh
(74) *Attorney, Agent, or Firm* — WILSON SONSINI GOODRICH & ROSATI

(57) ABSTRACT

The present disclosure provides transdermal drug delivery systems, methods, and platforms. In one example, the smart patch includes a drug-containing layer, a communication interface, and one or more sensors configured to detect a status change of the smart patch to the smart patch, the status change of the smart patch including one or more of removing a packaging from the smart patch and applying the smart patch to skin of the patient. The smart patch further includes a processor communicatively coupled to the one or more sensors and the communication interface, wherein the processor is configured to perform operations including automatically transiting between a plurality of working conditions based on the status change of the smart patch, the plurality of working conditions of the smart patch comprising a hibernation mode, a sleep mode, and a work mode and transmitting smart patch usage data via the communication interface.

20 Claims, 31 Drawing Sheets

Related U.S. Application Data

(60) Provisional application No. 63/504,475, filed on May 26, 2023.

(51) Int. Cl.
*A61M 35/00* (2006.01)
*G16H 20/13* (2018.01)
*G16H 40/67* (2018.01)

(52) U.S. Cl.
CPC ............. G16H 20/13 (2018.01); G16H 40/67 (2018.01); *A61M 2205/13* (2013.01); *A61M 2205/14* (2013.01); *A61M 2205/3306* (2013.01); *A61M 2205/3327* (2013.01); *A61M 2205/3576* (2013.01)

(58) Field of Classification Search
CPC .......... A61M 2205/3576; G16H 40/67; G16H 20/13; A61K 9/7039; A61K 9/0009
USPC .......................................................... 604/307
See application file for complete search history.

(56) References Cited

U.S. PATENT DOCUMENTS

| | | | |
|---|---|---|---|
| 8,095,213 B1 * | 1/2012 | Sexton | A61N 1/0492 604/20 |
| 8,821,945 B2 | 9/2014 | Imran et al. | |
| 8,926,509 B2 | 1/2015 | Magar et al. | |
| 9,327,105 B2 | 5/2016 | Ramdas et al. | |
| 9,743,880 B1 | 8/2017 | Euliano et al. | |
| 9,931,251 B2 | 4/2018 | Euliano et al. | |
| 10,004,887 B2 | 6/2018 | Gross et al. | |
| 10,035,010 B1 | 7/2018 | Wagstaff | |
| 10,213,586 B2 | 2/2019 | Netzel et al. | |
| 10,271,738 B2 | 4/2019 | Peeters | |
| 10,292,642 B2 | 5/2019 | Euliano et al. | |
| 10,321,849 B2 | 6/2019 | Euliano et al. | |
| 10,517,508 B2 | 12/2019 | Myers et al. | |
| 10,521,561 B1 | 12/2019 | Euliano et al. | |
| 10,765,360 B2 | 9/2020 | Euliano et al. | |
| 11,103,388 B2 | 8/2021 | Euliano et al. | |
| 11,369,789 B2 | 6/2022 | Jain et al. | |
| 11,399,721 B2 | 8/2022 | Mahalingam et al. | |
| 11,399,736 B2 | 8/2022 | Myers et al. | |
| 11,432,766 B2 | 9/2022 | Pandya et al. | |
| 2007/0148218 A1 | 6/2007 | Gordon | |
| 2007/0196456 A1 | 8/2007 | Stevens et al. | |
| 2009/0054737 A1 * | 2/2009 | Magar | A61B 5/7405 600/300 |
| 2011/0060280 A1 | 3/2011 | Caffey et al. | |
| 2012/0232431 A1 * | 9/2012 | Hudson | A61B 5/1071 600/595 |
| 2014/0350054 A1 | 11/2014 | Palmer et al. | |
| 2015/0065818 A1 | 3/2015 | Say et al. | |
| 2017/0258362 A1 | 9/2017 | Myers et al. | |
| 2018/0132784 A1 | 5/2018 | Euliano et al. | |
| 2018/0133466 A1 * | 5/2018 | Imran | A61N 1/325 |
| 2018/0182491 A1 | 6/2018 | Belliveau et al. | |
| 2019/0008698 A1 | 1/2019 | Euliano et al. | |
| 2019/0261920 A1 | 8/2019 | Euliano et al. | |
| 2019/0307363 A1 | 10/2019 | Euliano et al. | |
| 2020/0143926 A1 | 5/2020 | Euliano et al. | |
| 2020/0237257 A1 | 7/2020 | Myers et al. | |
| 2020/0258610 A1 * | 8/2020 | Patil | G16H 20/10 |
| 2020/0330011 A1 * | 10/2020 | Honore | A61B 5/1455 |
| 2021/0093248 A1 | 4/2021 | Euliano et al. | |
| 2022/0027698 A1 * | 1/2022 | Volkerink | G06K 19/07345 |
| 2022/0183996 A1 | 6/2022 | Rosing, Sr. et al. | |
| 2022/0273204 A1 | 9/2022 | Kamath et al. | |
| 2024/0212841 A1 | 6/2024 | Euliano et al. | |

* cited by examiner

TRANSDERMAL DRUG DELIVERY SYSTEM AND USES THEREOF

CROSS REFERENCE

This application is a continuation of International Application No. PCT/US2024/31005, filed May 24, 2024, which claims the benefit of U.S. Provisional Application No. 63/504,475, filed May 26, 2023, each of which is hereby incorporated by reference herein in its entirety.

BACKGROUND

Non-compliance with drug treatment is widespread. When patients are given medications by their doctors, nearly half forget to take the drug or do not take it as prescribed, and most of the patients stop the treatment as soon as they are feeling better. According to Centers for Disease Control and Prevention, 33%-69% of hospitalizations are caused by drug non-compliance. The estimated annual cost of drug-related morbidity and mortality resulting from drug non-compliance is over $500 billion in the US alone.

The current methods of monitoring drug compliance include patient questionnaires, patient self-reports, pill counts, rates of prescription refills. These indirect methods at most provide evidence of the drug being dispensed but not ingested. In addition, they are easily influenced by reporting bias. Direct assessment methods include monitoring patient's drug/metabolite levels and clinical response, which can be time-consuming and cost ineffective.

Direct assessment methods with single-use batteries, for example wearable drug delivery and compliance monitoring medical devices, often lack a battery small enough for patient comfort. Battery life is also an issue. Batteries that are sufficiently small for a comfortably wearable drug delivery and monitoring device often do not have batteries that can hold sufficient charge for hours, days, or weeks, or longer in a cost-efficient manner.

SUMMARY

There are needs for an efficient and convenient approach of monitoring drug compliance of patients. Patients can adhere to drug treatment without the need of filling in questionnaires or measuring drug response at the hospital, thereby improving the efficacy of drug treatment. Health care providers and other personnel involved in processes associated with healthcare of the patient can track the patient's drug compliance and provide interventions when necessary.

The present disclosure provides systems and methods that enable patients and health care providers to monitor drug compliance in an effective and efficient manner. The system and methods disclosed herein provide a multi-functional smart patch and uses thereof to treat a patient and to monitor drug compliance of the patient in real time.

The present disclosure provides systems and methods to increase battery life and cost-efficiency for a multi-functional smart patch. The present disclosure provides a battery of a sufficient size and design so as to be comfortable, long-lasting, and cost-effective when worn by the patient as part of a multi-functional smart patch.

One aspect of the present disclosure provides a transdermal drug delivery smart patch comprising a drug-containing layer, a communication interface and one or more sensors configured to detect a status change (or lack thereof) of the smart patch to the smart patch, the status change of the smart patch comprising one or more of removing a packaging from the smart patch and applying the smart patch to skin of the patient. The smart transdermal drug delivery patch also comprises a processor communicatively coupled to the one or more sensors and the communication interface, where the processor is configured to perform operations comprising automatically transiting between a plurality of working conditions based on the status change (or lack thereof) of the smart patch, the plurality of working conditions of the smart patch comprising a hibernation mode, a sleep mode, and a work mode, and transmitting smart patch usage data via the communication interface.

Another aspect of the present disclosure provides a method of treating a patient in need thereof using a transdermal drug delivery smart patch. The method comprises determining a status change (or lack thereof) of the smart patch to the smart patch using one or more sensors associated with the smart patch, the status change of the smart patch comprising one or more of removing a packaging from the smart patch and applying the smart patch to skin of the patient, and automatically transiting between a plurality of working conditions of the smart patch based on the determined status change (or lack thereof) of the smart patch, the plurality of working conditions comprising a hibernation mode, a sleep mode, and a work mode.

Another aspect of the present disclosure provides a method of enhancing drug compliance of a patient in need thereof using a transdermal drug delivery smart patch. The method comprises receiving, from the smart patch via a wireless network, information associated with a plurality of working conditions of the smart patch, the plurality of working conditions comprising a hibernation mode, a sleep mode, and a work mode, generating smart patch usage data based on the plurality of working conditions of the smart patch, wherein the smart patch usage data comprises at least one of a status change (or lack thereof) of the smart patch to the smart patch, a dose of a drug administered to the patient, a timing of the dose, or a frequency of doses, and the status change of the smart patch comprises one or more of removing a packaging from the smart patch and applying the smart patch to skin of the patient, and determining drug compliance of the patient based on the smart patch usage data and a medical record of the patient saved on the wireless network.

Another aspect of the present disclosure provides a transdermal drug delivery system. The system comprises a smart patch and backend application system comprising one or more computer processors that are individually or collectively programmed to perform operations. The smart patch comprises a drug-containing layer, a communication interface, and one or more sensors configured to detect a status change (or lack thereof) of the smart patch to the smart patch. The status change of the smart patch comprises one or more of removing a packaging from the smart patch and applying the smart patch to skin of the patient. The smart patch also comprises a processor communicatively coupled to the one or more sensors and the communication interface, where the processor is configured to perform operations comprising automatically transiting between a plurality of working conditions based on the status change (or lack thereof) of the smart patch, the plurality of working conditions of the smart patch comprising a hibernation mode, a sleep mode, and a work mode, and transmitting smart patch usage data via the communication interface. The performed operations comprise receiving, from the smart patch, information associated with the plurality of working conditions of the smart patch via the wireless network, generating smart patch usage data based on the plurality of working conditions of the smart patch, wherein the smart patch usage data comprises one or more of the status changes (or lack thereof) of the smart patch, a dose of a drug administered to the patient, a timing of the dose, or a frequency of doses, and determining drug compliance of the patient based on the smart patch usage data and the medical record of the patient saved on the wireless network.

Another aspect of the present disclosure provides a system comprising one or more computer processors and computer memory coupled thereto. The computer memory comprises machine executable code that, upon execution by the one or more computer processors, implements any of the methods above or elsewhere herein.

Another aspect of the present disclosure provides a non-transitory computer readable medium comprising machine executable code that, upon execution by one or more computer processors, implements any of the methods above or elsewhere herein.

One aspect of the present disclosure provides a non-transitory computer readable medium comprising machine executable code that, upon execution by one or more computer processors, implements a method of treating a patient in need thereof using a transdermal drug delivery smart patch. The method comprises determining a status change (or lack thereof) of the smart patch to the smart patch using one or more sensors associated with the smart patch, the status change of the smart patch comprising one or more of removing a packaging from the smart patch and applying the smart patch to skin of the patient, and automatically transiting between a plurality of working conditions of the smart patch based on the determined status change (or lack thereof) of the smart patch, the plurality of working conditions comprising a hibernation mode, a sleep mode, and a work mode.

In some embodiments, a method or system provided herein comprises periodic status checks, such as wherein status is not changed (e.g., the package hasn't been opened, the patch hasn't been removed from the patient, the patch hasn't been placed on the patient, etc.). For example, in some embodiments, a smart patch will periodically check the status of the smart patch. In some embodiments, a smart patch wakes up from a sleep mode periodically transmit stored states (e.g., changes and/or lack thereof). In certain embodiments, a smart patch wakes up from a sleep mode periodically check and transmit patch states (e.g., changes and/or lack thereof).

In some embodiments, the TET smart patch can manually receive a signal upon user interaction with one or more pieces of software. In some embodiments, the smart patch can periodically receive a signal multiple times per second, once per second, multiple times per minute, once per minute, one or more times per about two minutes, one or more times per about five minutes, one or more times per about ten minutes, one or more times per about 15 minutes, one or more times per about 30 minutes, one or more times per about one hour, one or more times per about two hours, one or more times per about three hours, one or more times per about four hours, one or more times per about six hours, one or more times per about ten hours, one or more times per about twelve hours, one or more times per about 24 hours, one or more times per about 36 hours, one or more times per about 48 hours, one or more times per about one week, one or more times per about two weeks, one or more times per about one month, one or more times per about two months, one or more times per about three months, one or more times per about six months, one or more times per about twelve months, one or more times per about one year, or one or more times per about more than one year. In some embodiments, the smart patch can periodically check the status of the smart patch multiple times per second, once per second, multiple times per minute, once per minute, one or more times per about two minutes, one or more times per about five minutes, one or more times per about ten minutes, one or more times per about 15 minutes, one or more times per about 30 minutes, one or more times per about one hour, one or more times per about two hours, one or more times per about three hours, one or more times per about four hours, one or more times per about six hours, one or more times per about ten hours, one or more times per about twelve hours, one or more times per about 24 hours, one or more times per about 36 hours, one or more times per about 48 hours, one or more times per about one week, one or more times per about two weeks, one or more times per about one month, one or more times per about two months, one or more times per about three months, one or more times per about six months, one or more times per about twelve months, one or more times per about one year, or one or more times per about more than one year.

In some embodiments, the TET smart patch can manually transmit a signal upon user interaction with one or more pieces of software. In some embodiments, the smart patch can periodically transmit a signal multiple times per second, once per second, multiple times per minute, once per minute, one or more times per about two minutes, one or more times per about five minutes, one or more times per about ten minutes, one or more times per about 15 minutes, one or more times per about 30 minutes, one or more times per about one hour, one or more times per about two hours, one or more times per about three hours, one or more times per about four hours, one or more times per about six hours, one or more times per about ten hours, one or more times per about twelve hours, one or more times per about 24 hours, one or more times per about 36 hours, one or more times per about 48 hours, one or more times per about one week, one or more times per about two weeks, one or more times per about one month, one or more times per about two months, one or more times per about three months, one or more times per about six months, one or more times per about twelve months, one or more times per about one year, or one or more times per about more than one year. In some embodiments, the smart patch can periodically transmit the status of the smart patch multiple times per second, once per second, multiple times per minute, once per minute, one or more times per about two minutes, one or more times per about five minutes, one or more times per about ten minutes, one or more times per about 15 minutes, one or more times per about 30 minutes, one or more times per about one hour, one or more times per about two hours, one or more times per about three hours, one or more times per about four hours, one or more times per about six hours, one or more times per about ten hours, one or more times per about twelve hours, one or more times per about 24 hours, one or more times per about 36 hours, one or more times per about 48 hours, one or more times per about one week, one or more times per about two weeks, one or more times per about one month, one or more times per about two months, one or more times per about three months, one or more times per about six months, one or more times per about twelve months, one or more times per about one year, or one or more times per about more than one year.

Another aspect of the present disclosure provides a non-transitory computer readable medium comprising machine executable code that, upon execution by one or more computer processors, implements a method of enhancing drug compliance of a patient in need thereof using a transdermal drug delivery smart patch. The method comprises receiving, from the smart patch via a wireless network, information associated with a plurality of working conditions of the smart patch, the plurality of working conditions comprising a hibernation mode, a sleep mode, and a work mode, generating smart patch usage data based on the plurality of working conditions of the smart patch, wherein the smart patch usage data comprises at least one of a status change of the smart patch to the smart patch, a dose of a drug administered to the patient, a timing of the dose, or a frequency of doses, and the status change of the smart patch comprises one or more of removing a packaging from the smart patch and applying the smart patch to skin of the patient, and determining drug compliance of the patient based on the smart patch usage data and a medical record of the patient saved on the wireless network.

Another aspect of the present disclosure provides a transdermal drug delivery smart patch, comprising a drug-containing layer; a communication interface; a processor communicatively coupled to the communication interface, wherein the processor is configured to perform operations comprising: (a) receiving a wireless signal or electric current through the communication interface; and (b) releasing a (e.g., predetermined) amount of drug from the drug-containing layer. The processor comprises a system-on-a-chip (SoC). The SoC comprises one or more of a messaging subsystem, a sensor subsystem, a power state subsystem, a communication state subsystem, a communication subsystem, a printable battery, or an event cache subsystem, or any combination thereof. The communication subsystem receives data from a cloud server system using the wireless signal or the electric current. One or more drugs are loaded on the drug-containing layer. The one or more drugs are lipophilic or hydrophilic. One or more placebos are loaded on the drug-containing layer. The drug-containing layer comprises a layer of drug-in-adhesive. The drug-containing layer comprises a plurality of layers of drug-in-adhesive and a membrane positioned therebetween. The drug-containing layer comprises a drug reservoir, an adhesive layer, and a membrane positioned therebetween. The drug-containing layer comprises a drug reservoir and an adhesive ring therearound. The drug-containing layer comprises a drug-containing microneedle array and an adhesive layer. The drug-containing layer comprises one or more excipients that facilitate (i) permeation of the drug through the skin and (ii) drug delivery. One or more excipients comprise one or more chemical enhancers. The wireless signal or the electric current received by the communication interface is associated with releasing the drug.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the present disclosure are utilized, and the accompanying drawings (also "Figure" and "FIG." herein), of which:

DETAILED DESCRIPTION

Figure 1:
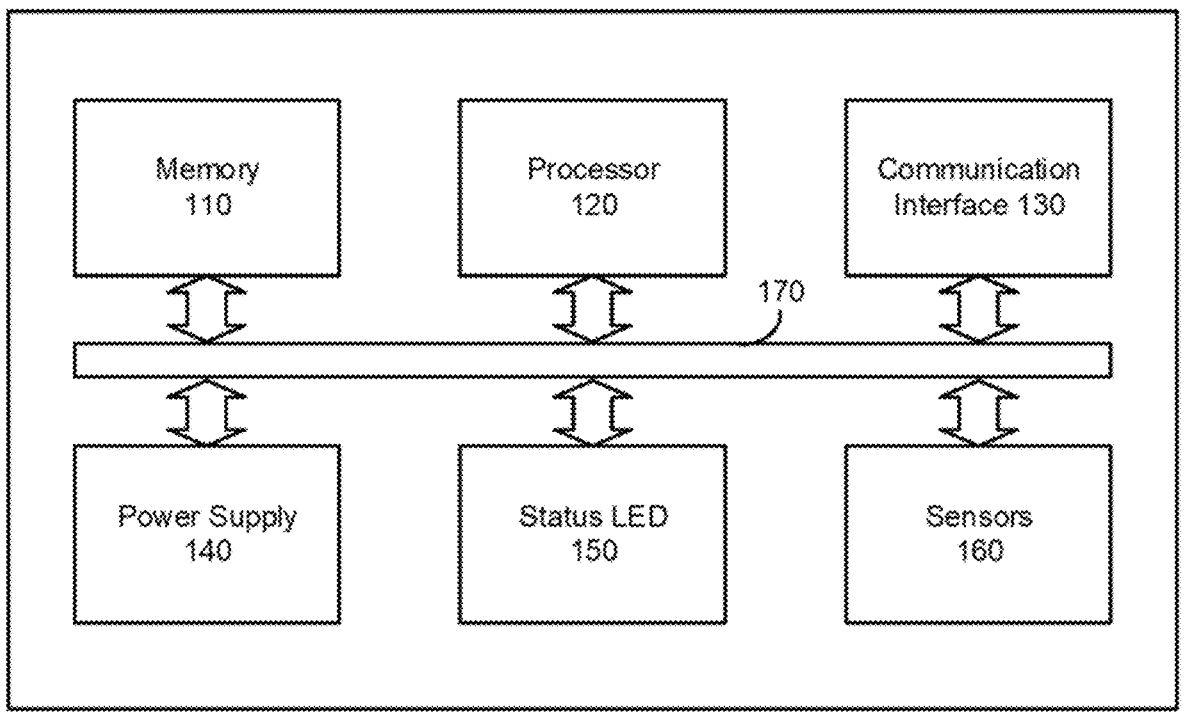
FIG. 1 is a block diagram of a non-limiting example of transdermal drug delivery smart patch, according to some embodiments of the present disclosure.

While various embodiments of the present disclosure have been shown and described herein, it will be obvious to those skilled in the art that such embodiments are provided by way of example only. Numerous variations, changes, and substitutions may occur to those skilled in the art without departing from the present disclosure. It should be understood that various alternatives to the embodiments of the present disclosure described herein may be employed.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The term "and/or" used herein to link one or more species means one of the species or any combinations of the one or more species.

The term "transdermal" refers to a route of administration wherein ingredients are delivered across the skin for systemic distribution. Examples include transdermal patches used for medicine delivery. The drug is administered in the form of a smart patch or ointment that delivers the drug into the circulation for systemic effect. Transdermal administration can be accomplished by applying, pasting, rolling, attaching, pouring, pressing, rubbing, etc., of a transdermal preparation onto a skin surface.

The term "transdermal patch" refers to a matrix or liquid type of delivery device which is used to transdermally deliver doses of a substance from skin to a patient's bloodstream, over a specific application period.

The term "transdermal smart patch," "smart transdermal patch," "smart transdermal smart patch," "smart transdermal drug delivery smart patch," "transdermal drug delivery smart patch," and "smart transdermal drug delivery patch", are used herein interchangeably.

The term "drug" as used herein generally refers to any substance that alters the physiology of a subject. The term "drug" may be used interchangeably herein with the terms "therapeutic agent", "medication", "pharmacologically active agent", "active pharmaceutical ingredients (APIs)" and the like. It will be understood that a "drug" formulation may include more than one therapeutic agent, wherein exemplary combinations of therapeutic agents include a combination of two or more drugs.

The term "reservoir" as used herein refers to any form of mechanism to retain an element, compound, pharmaceutical composition, active agent, and the like, in a liquid state, solid state, gaseous state, mixed state and/or transitional state. Typically, a reservoir serves to retain a biologically active agent (e.g., drug) prior to the discharge of such agent into the biological interface.

The term "adhesive" refers to any non-metallic substance applied to one or both surfaces of two separate items that binds them together and resists their separation. Adhesive, also known as glue, cement, mucilage, or paste. Adhesive may be classified in a variety of ways depending on their chemistries (e.g., epoxies, polyurethanes, polyimides), forms (e.g., paste, liquid, film, pellets, tape), types (e.g., hot melt, reactive hot melt, thermosetting, pressure sensitive, contact, etc.), or load carrying capabilities (structural, semi-structural, or non-structural).

The term "processor" may be used interchangeably with terms such as "microprocessor", "controller", "microcontroller", and the like.

Disclosed is a smart transdermal drug delivery patch comprising a drug-containing layer, a communication interface, one or more sensors configured to detect a status change of the smart patch to the smart patch, and a processor communicatively coupled to the one or more sensors. The status change of the smart patch may comprise removing a packaging from the smart patch, applying the smart patch to the patient skin, and removing the smart patch from the patient skin. The processor may control the smart patch to automatically transit between the plurality of working conditions based on the detected status change of the smart patch, and transmit smart patch usage data via the communication interface.

The smart transdermal drug delivery patch may have different working conditions, for example, a hibernation mode, a sleep mode, and a work mode. The smart patch may be at the hibernation mode as default after being manufactured, or when stored in a packaging (e.g., wrapped). When a patient removes the packaging from the smart patch, the processor may control the smart patch to automatically transit from the hibernation mode to a non-hibernation mode (e.g., sleep mode and work mode).

In some embodiments, the smart patch may comprise a flex circuit in electrical connection with the sensors. The flex circuit may comprise one or more conducting pads. The packaging may comprise a wrapper with one or more of conducting pads and conducting traces positioned on an inner surface of the wrapper. When the wrapper is in contact with the smart patch, the conducting pads and conducting traces on the wrapper and the conducting pads on the flex circuit may form an electrical connection. When the patient removes the wrapper, the connection may be interrupted and detected by the sensors. The processor may control the smart patch to switch working conditions based on this status change of the smart patch. In some embodiments, one or more sensors of a TET smart patch may activate in response to a package surrounding the TET smart patch or attached to the TET smart patch being manipulated or opened. In some embodiments, one or more sensors of the TET smart patch can be activated when a seal of a packaging surrounding the TET smart patch or attached to the TET smart patch is broken. In some embodiments, the TET smart patch can complete an electric circuit with a low-energy electrical current when in the packaging. In some embodiments, manipulating one or more parts of the packaging, like breaking a seal, peeling back a portion of the package, ripping or poking one or more parts of the package, or disconnecting a part of the package, for example, can activate the one or more sensors. The sensors can be, for example, light sensors, electricity sensors, pressure sensors, infrared sensors, sound sensors, ultrasound sensors, gas sensors, capacitive sensors, humidity sensors, touch sensors, temperature sensors, magnetic field sensors, resistive sensors, or any combination thereof.

When the smart patch is at the sleep mode, the processor may control the smart patch to automatically transit from the sleep mode to the work mode, upon further status change of the smart patch, including removing a liner from the smart patch, and applying the smart patch to patient skin. In some embodiments, the packaging may comprise a removable liner in contact with the drug-containing layer. The removable liner may comprise one or more of conducting pads and conducting traces. When the liner is in contact with the drug-containing layer, the conducting pads and conducting traces on the liner and the conducting pads on the flex circuit may form an electrical connection. When the patient removes the liner, the connection may be interrupted and detected by the sensors. The processor may control the smart patch to switch working conditions based on this status change of the smart patch.

In some embodiments, when the patient applies the smart patch to the skin of the patient, the conducting pads on the flex circuit and the skin may form an electrical connection, which can be detected by the sensors. The processor may control the smart patch to switch working conditions based on this status change of the smart patch. The processor may further analyze an electrodermal response between the skin and the conducting pads for clinical diagnostic data collection and monitoring. Similarly, when the patient removes the smart patch from the skin, the electrical connection between the conducting pads on the flex circuit and the skin may be interrupted and detected by the sensors. The processor may control the smart patch to switch working conditions based on this status change of the smart patch, for example, from the work mode to one of the sleep mode and hibernation mode.

In other embodiments, when the wrapper is removed, the smart patch may be switched from the hibernation mode to the work mode. The processor may control the smart patch to remain in the current working condition when the patient performs further actions, including removing the liner and applying the smart patch.

In some embodiments, the smart patch may be at the sleep mode as default during use. The sleep mode requires lower power consumption and extends the use life of the smart patch. The processor may control the smart patch to remain at the sleep mode until a sensing event (e.g., status change of the smart patch to the smart patch) occurs and is detected by the sensors, and/or the smart patch receives a communication signal via the communication interface. For example, the patient may be non-adherent to her medication and remove the smart patch early. When the smart patch is connected to a wireless network, a smart device (e.g., a mobile device, smart watch, smart speakers and displays like Amazon Echo Show) may receive an alert or intervention message from a cloud or other user devices (e.g., health provider devices) in the network requesting the patient for drug compliance.

In some embodiments, the battery may enter a low-power mode. In some embodiments, the battery may enter a low-power mode as a result of communication from the communication subsystem of the TET smart patch. In some embodiments, the battery may enter a low-power mode as a result of a communication from a cloud module. In some embodiments, the battery may enter a low-power mode in response to a signal from one or more sensors. In some embodiments, the battery can enter a low-power mode to preserve battery and extend battery life. In some embodiments, the battery can enter a low-power mode as a result of a signal for a change of the TET smart patch from work mode to sleep or hibernation mode. In some embodiments, the battery may exit a low-power mode. In some embodiments, the battery may exit a low-power mode as a result of communication from the communication subsystem of the TET smart patch. In some embodiments, the battery may exit a low-power mode as a result of a communication from a cloud module. In some embodiments, the battery may exit a low-power mode in response to a signal from one or more sensors. In some embodiments, the battery can exit a low-power mode to preserve battery and extend battery life. In some embodiments, the battery can exit a low-power mode as a result of a signal for a change of the TET smart patch from sleep or hibernation mode to work mode. In some embodiments, the signal for a change of the TET smart patch can be transmitted multiple times per second, once per second, multiple times per minute, once per minute, one or more times per about two minutes, one or more times per about five minutes, one or more times per about ten minutes, one or more times per about 15 minutes, one or more times per about 30 minutes, one or more times per about one hour, one or more times per about two hours, one or more times per about three hours, one or more times per about four hours, one or more times per about six hours, one or more times per about ten hours, one or more times per about twelve hours, one or more times per about 24 hours, one or more times per about 36 hours, one or more times per about 48 hours, one or more times per about one week, one or more times per about two weeks, one or more times per about one month, one or more times per about two months, one or more times per about three months, one or more times per about six months, one or more times per about twelve months, one or more times per about one year, or one or more times per about more than one year.

In other embodiments, the processor may control the smart patch to switch between the sleep mode and the work mode periodically. When the smart patch is switched to the work mode, the processor may transmit smart patch usage data, a current working condition of the smart patch, transitions of working conditions, a state of sensors, a sequence of state changes, date and time stamp of each state change, a unique smart patch identifier via the communication interface.

In some embodiments, after being applied to the patient skin, the smart transdermal drug delivery patch may have a use life of 1-5 hours, 1-10 hours, 1-20 hours, 1-30 hours, 1-40 hours, 1-50 hours, 1-60 hours, 1-70 hours, 1-80 hours, 1-90 hours, 1-100 hours, 1-110 hours, 1-120 hours, 1-130 hours, 1-140 hours, 1-150 hours, 1-160 hours, or 1-170 hours.

In some embodiments, the drug-containing layer may comprise a layer of drug-in-adhesive. In other embodiments, the drug-containing layer may comprise a plurality of layers of drug-in-adhesive and a membrane positioned therebetween. In other embodiments, the drug-containing layer may comprise a drug reservoir, an adhesive layer and a membrane positioned therebetween. In other embodiments, the drug-containing layer may comprise a drug-containing microneedle array and an adhesive layer. The adhesive layer may surround each of the microneedles.

In some embodiments, the drug-containing layer may comprise one or more drugs loaded thereon. In some embodiments, the drug-containing layer may also comprise one or more excipients. In some embodiments, the one or more excipients may comprise one or more chemical enhancers that facilitate the permeation of the drug through the skin and drug delivery.

In some embodiments, the smart patch may comprise one or more status LEDs controlled by the processor that provide visual indications of the current working conditions and transitions between working conditions, and potential malfunction of the smart patch.

In some embodiments, the smart patch may comprise a power supply. In some embodiments, the power supply may be a printed power supply.

In some embodiments, the smart transdermal drug delivery patch processor may comprise a system-on-a-chip (SoC). In some embodiments, the SoC can comprise one or more of a messaging subsystem, a sensor subsystem, a power state subsystem, a communication state subsystem, a communication subsystem, a printable battery, or an event cache subsystem, or any combination thereof.

In some embodiments, the communication subsystem can send data to or from a cloud server system. In some embodiments, the sensor subunit can receive data from the one or more sensors. In some cases, the one or more sensors can detect information concerning the smart patch status data.

The smart patch may comprise memory that stores smart patch usage data comprising one or more of the status changes of the smart patch, a dose of the drug, an overdose of the drug, a missed dose, an aborted dose, a timing of the dose, a frequency of doses, a current working condition of the smart patch, transitions of the working conditions of the smart patch, or any combination thereof. Additionally, the memory may store a unique smart patch identifier, a current state of each of the sensors, a sequence of state changes of the sensors, date and time stamp of each state change, or any combination thereof.

The smart patch may be connected to a wireless network. The network may be a mesh network or an Internet of Things (IoT) network. The smart patch may transmit smart patch usage data to one or more devices in the network via the communication interface. In some embodiments, devices with backend applications in the network may receive patient data comprising clinical data, a geolocation, a physical activity, a motion, demographics associated with the patient. The clinical data may comprise drug prescription, an expected dosage of the drug, an expected timing of administering the drug, an electronic health record (EHR) of the patient, and physiological parameters of the patient.

In some embodiments, devices with backend applications in the network may determine the drug compliance of the patient based on the smart patch usage data and patient data. For example, the smart patch usage data may be compared with the patient's drug prescription, an expected dosage, and/or an expected timing of administering the drug. When there is inconsistency indicating non-compliance, the devices may generate an alert, a reporting message, or an intervention message of the drug compliance, which may be transmitted to other devices in the network.

In some embodiments, the smart patch status data can be generated using a processor contained within the transdermal drug delivery smart patch to average the values of one or more sensor inputs of the smart patch. In some embodiments, drug compliance can be determined by comparing an individual value measured by the one or more sensors of the smart patch to an average value of sensor inputs of the smart patch.

During the use of the smart patch, the patient may wear other devices that collect patient data including physiological parameters, physical activities, and motions, and transmit the data to the network. Upon receiving the data, the devices with backend applications in the network may determine whether the patient has a clinical response to the drug, for example, an adverse drug reaction. The devices may generate messages to the patient device providing guidance of handling medical emergency, and an alert to health provider's devices such that health providers can provide further intervention.

FIG. 1 is a block diagram of a non-limiting example of transdermal drug delivery smart patch, according to some embodiments of the present disclosure. The smart transdermal drug delivery patch 100 comprises memory 110, one or more processors 120, communication interface 130, power supply 140, one or more status LED 150, and one or more sensors 160 that communicate with each other, and with other components, via a bus 170. All of these elements may interface directly or via one or more interfaces or adaptors to the bus 170.

The smart transdermal drug delivery patch 100 comprises one or more processor(s) 120 that carry out functions and control other components in the smart patch. The processor(s) 120 may optionally contain a cache memory unit for temporary local storage of instructions, data, or computer addresses. The processor(s) 120 may be configured to assist in execution of computer readable instructions. The smart patch 100 may provide functionality for other components depicted in FIG. 1 as a result of the processor(s) 120 executing non-transitory, processor-executable instructions embodied in one or more computer-readable storage media, such as memory 110. The computer-readable media may store software that implements particular embodiments, and the processor(s) 120 may execute the software. The memory 110 may read the software from one or more other computer-readable media or from one or more other sources through a suitable interface, such as communication interface 130. The software may cause the processor(s) 120 to carry out one or more processes or one or more steps of one or more processes described or illustrated herein. Carrying out such processes or steps may include defining data structures stored in the memory 110 and modifying the data structures as directed by the software.

The memory 110 may include various components (e.g., machine readable media) including, but not limited to, a random-access memory component (e.g., RAM) (e.g., static RAM (SRAM), dynamic RAM (DRAM), ferroelectric random access memory (FRAM), phase-change random access memory (PRAM), etc.), a read-only memory component (e.g., ROM), or any combination thereof. ROM may act to communicate data and instructions unidirectionally to the processor(s) 120, and RAM may act to communicate data and instructions bidirectionally with the processor(s) 120. ROM and RAM may include any suitable tangible computer-readable media. In one example, a basic input/output system (BIOS), including basic routines that help to transfer information between elements within the smart patch 100, such as during start-up, may be stored in the memory 110.

The smart patch 100 may communicate with a network via the communication interface 130. The smart patch 100 may communicate with other devices in the network via the communication interface. The other devices may include personal devices and enterprise systems, distributed computing systems, cloud storage systems, cloud computing systems, and the like, connected to a network. In some embodiments, the other devices may comprise device(s) associated with the patient, device(s) associated with health providers/caregivers, and device(s) associated with business operators associated with healthcare of the patient, including insurance and pharmacy.

Communications to and from the smart patch 100 may be sent through the communication interface 130. The smart patch 100 may store outgoing communications (e.g., smart patch usage data, unique smart patch identifier, sensor state data) in the form of one or more packets in the memory 110 and communicated to the network from the communication interface 130. In some embodiments, the smart patch usage data may comprise status change of the smart patch, a dose of the drug, an overdose of the drug, a missed dose, an aborted dose, a timing of the dose, a frequency of doses, a current working condition of the smart patch, transitions of the working conditions of the smart patch, a malfunction of the smart patch, or any combination thereof. The processor 120 may transmit smart patch usage data to the network via the communication interface 130.

The communication interface 130 may receive incoming communications in the form of one or more packets from the network or other devices, and the smart patch 100 may store and process the incoming communications in the memory 110 for processing. In some embodiments, users (e.g., health care providers/caregivers) on the network may determine drug compliance of the patient based on the received smart patch usage data. In other embodiments, backend applications in the network may automatically determine, based on the smart patch usage data, drug compliance of the patient. When non-compliance is identified, an alert, a reporting message, or an intervention message of the drug compliance may be generated and transmitted via the network. In some embodiments, incoming communications like alerts and messages may be received on the patient's device connected to the network, thereby notifying the non-compliance. The smart patch 100, connected to the patient's device via a wireless network (e.g., IoT), may receive communications from the patient's device and switch working conditions, for example, from the sleep mode to work mode.

In some embodiments, the smart patch status data can be generated using a processor contained within the transdermal drug delivery smart patch to average the values of one or more sensor inputs of the smart patch. In some embodiments, drug compliance can be determined by comparing an individual value measured by the one or more sensors of the smart patch to an average value of sensor inputs of the smart patch.

The communication interface 130 may include, but not limited to, a network interface. Examples of the network or network segment may include, but not limited to, a distributed computing system, a cloud computing system, a wide area network (WAN) (e.g., the Internet, an enterprise network), a local area network (LAN) (e.g., a network associated with an office, a building, a campus or other relatively small geographic space), a telephone network, a direct connection between two computing devices, a peer-to-peer network, and any combination thereof. The network may employ a wired and/or a wireless mode of communication. The network may be a mesh network. The network may be an IoT network. In general, any network topology may be used.

In some embodiments, the communication may use a protocol selected from the group consisting of, but not limited to, Bluetooth, Wi-Fi, ZigBee, Thread, Z-Wave, LoRa, Near Field Communication (NFC), Broadband, Narrow Band-Internet of Things (NB-IoT), Radio Frequency Identification System (RFID), WLAN, 3G, 4G, and 5G, and future revisions of the aforementioned protocol standards. For example, the smart patch 100 may wirelessly communicate with other devices via Bluetooth Low Energy (BLE).

The power supply 140 may provide power to the smart patch 100 during its use. In some embodiments, the power supply 140 may comprise a printed power supply or a thin-film power supply. The printed power supply may be printed batteries.

The smart patch 100 may comprise an output device, for example, status LED 150, controlled by the processor that provides a visual indication of the working conditions of the smart patch 100. The status LED 150 may comprise one or more LEDs. In some embodiments, the color, numbers, on/off status, blinks with different frequencies, or any combination thereof may be used to indicate the status of the smart patch 100, including whether the smart patch is functioning normally, the current working condition and transitions of working conditions.

The sensors 160 may comprise one or more sensors that are communicatively connected to the processor 120 via the bus 170. The sensors 160 may monitor status change of the smart patch to the smart patch 100. In some embodiments, the sensors 160 may comprise one or more optical sensors. When a patient removes a packaging from the smart patch 100, the optical sensors may detect the incident light change, convert it into electrical signals and transmit to the processor 120. In some embodiments, the optical sensors can transmit the signal multiple times per second, once per second, multiple times per minute, once per minute, one or more times per about two minutes, one or more times per about five minutes, one or more times per about ten minutes, one or more times per about 15 minutes, one or more times per about 30 minutes, one or more times per about one hour, one or more times per about two hours, one or more times per about three hours, one or more times per about four hours, one or more times per about six hours, one or more times per about ten hours, one or more times per about twelve hours, one or more times per about 24 hours, one or more times per about 36 hours, one or more times per about 48 hours, one or more times per about one week, one or more times per about two weeks, one or more times per about one month, one or more times per about two months, one or more times per about three months, one or more times per about six months, one or more times per about twelve months, one or more times per about one year, or one or more times per about more than one year.

Upon receiving the signal representing the status change of the smart patch of removing the packaging, the processor 120 may automatically control the smart patch to transit between working conditions. The sensor state and the state changes which represent the given status change of the smart patch, may be stored in the memory 110.

In other embodiments, the sensors 160 may comprise electronic sensors that detect electronic signal changes caused by status change of the smart patch to the smart patch 100. For example, the sensors 160 may detect the electronic signal changes caused by patient removing a packaging from the smart patch, applying the smart patch to skin, or removing the smart patch from skin. In some embodiments, the sensors can periodically detect the electronic signal multiple times per second, once per second, multiple times per minute, once per minute, one or more times per about two minutes, one or more times per about five minutes, one or more times per about ten minutes, one or more times per about 15 minutes, one or more times per about 30 minutes, one or more times per about one hour, one or more times per about two hours, one or more times per about three hours, one or more times per about four hours, one or more times per about six hours, one or more times per about ten hours, one or more times per about twelve hours, one or more times per about 24 hours, one or more times per about 36 hours, one or more times per about 48 hours, one or more times per about one week, one or more times per about two weeks, one or more times per about one month, one or more times per about two months, one or more times per about three months, one or more times per about six months, one or more times per about twelve months, one or more times per about one year, or one or more times per about more than one year.

The sensors 160 may transmit the electrical signal change to the processors 120, which may in turn control the smart patch to transit between different working conditions based on the given status change of the smart patch. In some embodiments, the sensors can transmit the electrical signal change to the processors multiple times per second, once per second, multiple times per minute, once per minute, one or more times per about two minutes, one or more times per about five minutes, one or more times per about ten minutes, one or more times per about 15 minutes, one or more times per about 30 minutes, one or more times per about one hour, one or more times per about two hours, one or more times per about three hours, one or more times per about four hours, one or more times per about six hours, one or more times per about ten hours, one or more times per about twelve hours, one or more times per about 24 hours, one or more times per about 36 hours, one or more times per about 48 hours, one or more times per about one week, one or more times per about two weeks, one or more times per about one month, one or more times per about two months, one or more times per about three months, one or more times per about six months, one or more times per about twelve months, one or more times per about one year, or one or more times per about more than one year.

The bus 170 connects a wide variety of subsystems. Herein, reference to a bus may encompass one or more digital signal lines serving a common function, where appropriate. The Bus 170 may be any of several types of bus structures including, but not limited to, a memory bus, a memory controller, a peripheral bus, a local bus, and any combination thereof, using any of a variety of bus architectures. In some embodiments, the bus 170 may be an on-chip bus. Some of the non-limiting examples of bus architectures may comprise Advanced Microcontroller Bus Architecture (AMBA) which may include an Advanced High-performance Bus (AHB), an Advanced System Bus (ASB), and an Advanced Peripheral Bus (APB), AMBA Advanced eXtensible Interface (AXI) bus, a WISHBONE bus, an Open Core Protocol (OCP), a CoreConnect bus, MSBUS that comprises a master bus (MBUS) and a slave bus (SBUS), and any combination thereof.

Figure 2:
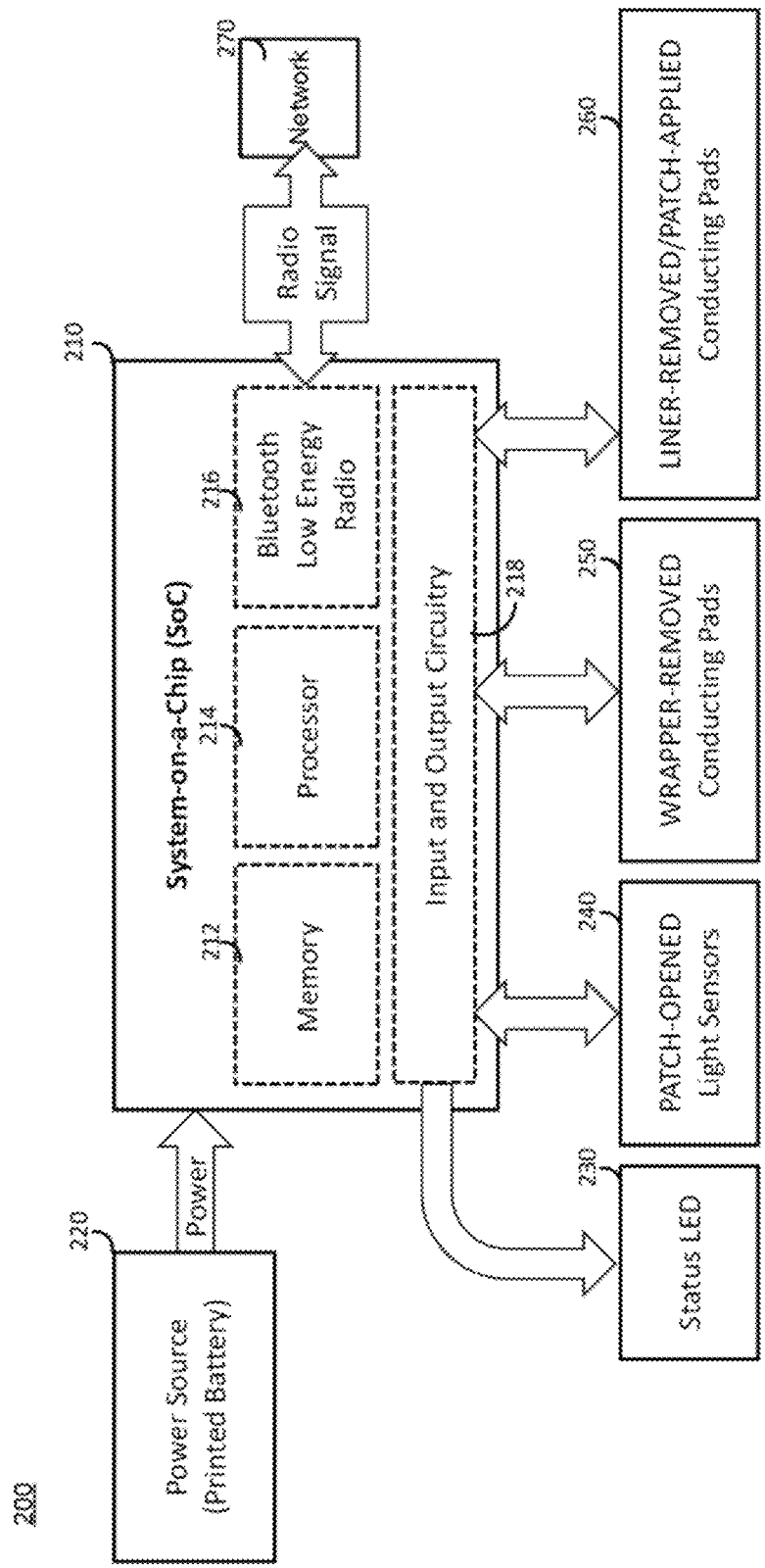
FIG. 2 is a block diagram of a non-limiting example of transdermal drug delivery smart patch, according to some embodiments of the present disclosure.

FIG. 2 is a block diagram of a non-limiting example of smart transdermal drug delivery patch 200. The smart patch 200 comprises a flex circuit 210 comprising memory 212, a processor 214, a Bluetooth Low Energy Radio 216, and an input-and-output circuitry 218. The flex circuit 210 may be a system-on-chip (e.g., integrated circuit). The Bluetooth Low Energy Radio 216 functions as the communication interface (e.g., communication interface 130 in FIG. 1) by transmitting radio signals and communicating with a network 270.

In some embodiments, the Bluetooth Low Energy Radio can transmit radio signals multiple times per second, once per second, multiple times per minute, once per minute, one or more times per about two minutes, one or more times per about five minutes, one or more times per about ten minutes, one or more times per about 15 minutes, one or more times per about 30 minutes, one or more times per about one hour, one or more times per about two hours, one or more times per about three hours, one or more times per about four hours, one or more times per about six hours, one or more times per about ten hours, one or more times per about twelve hours, one or more times per about 24 hours, one or more times per about 36 hours, one or more times per about 48 hours, one or more times per about one week, one or more times per about two weeks, one or more times per about one month, one or more times per about two months, one or more times per about three months, one or more times per about six months, one or more times per about twelve months, one or more times per about one year, or one or more times per about more than one year.

The input-and-output circuitry 218 on the flex circuit is communicatively coupled to status LED 230, optical sensors 240, and other components including the conducting pads 250 and 260 on the packaging (e.g., wrapper and liner). The power supply 220 provides power to the flex circuit 210.

The optical sensors 240, in electrical connection with the input-and-output circuitry 218, may monitor the status change of the smart patch of opening the smart patch 200. The optical sensors 240 may convert the incident light change caused by the status change of the smart patch into an electrical signal, which is detected by the input-and-output circuitry 218. In response, the processor 214 may control the smart patch 200 to transit between working conditions. In some embodiments, the smart patch can transit between working conditions multiple times per second, once per second, multiple times per minute, once per minute, one or more times per about two minutes, one or more times per about five minutes, one or more times per about ten minutes, one or more times per about 15 minutes, one or more times per about 30 minutes, one or more times per about one hour, one or more times per about two hours, one or more times per about three hours, one or more times per about four hours, one or more times per about six hours, one or more times per about ten hours, one or more times per about twelve hours, one or more times per about 24 hours, one or more times per about 36 hours, one or more times per about 48 hours, one or more times per about one week, one or more times per about two weeks, one or more times per about one month, one or more times per about two months, one or more times per about three months, one or more times per about six months, one or more times per about twelve months, one or more times per about one year, or one or more times per about more than one year.

In some embodiments, the packaging (e.g., wrapper, liner) of the smart patch 200 may comprise one or more conducting pads 250 and 260. When the packaging is removed by the patient, the electrical connection between the conducting pads 250/260 and the input-and-output circuitry 218 may be changed. In response, the processor 214 may control the smart patch 200 to transit between working conditions. In some embodiments, the smart patch can transit between working conditions multiple times per second, once per second, multiple times per minute, once per minute, one or more times per about two minutes, one or more times per about five minutes, one or more times per about ten minutes, one or more times per about 15 minutes, one or more times per about 30 minutes, one or more times per about one hour, one or more times per about two hours, one or more times per about three hours, one or more times per about four hours, one or more times per about six hours, one or more times per about ten hours, one or more times per about twelve hours, one or more times per about 24 hours, one or more times per about 36 hours, one or more times per about 48 hours, one or more times per about one week, one or more times per about two weeks, one or more times per about one month, one or more times per about two months, one or more times per about three months, one or more times per about six months, one or more times per about twelve months, one or more times per about one year, or one or more times per about more than one year.

In other embodiments, the flex circuit 210 may comprise one or more conducting pads. When the patient applies the smart patch to her skin, the input-and-output circuitry 218 may detect the change in the electrical connection between the conducting pads of the flex circuit 210 and the skin. Accordingly, the processor 214 may control the smart patch 200 to transit between working conditions based on the signal change in the input-and-output circuitry 218.

Figure 3:
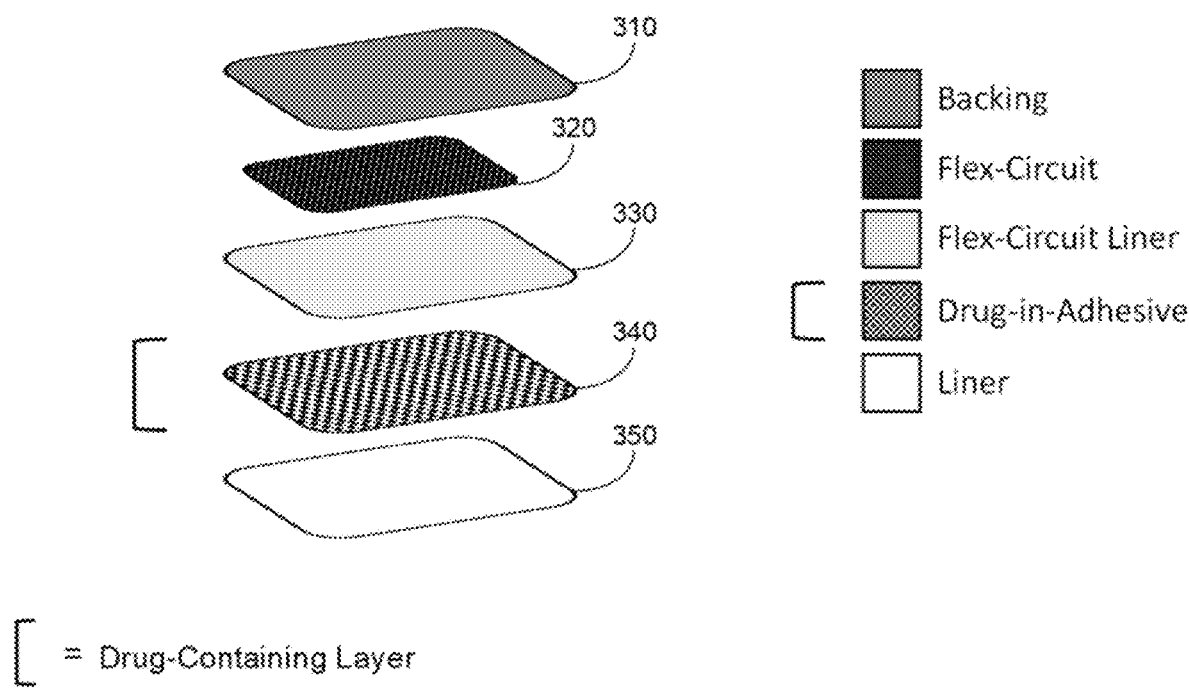
FIG. 3 illustrates the structure of a non-limiting example of smart transdermal drug delivery patch comprising a layer of drug-in-adhesive, according to some embodiments of the present disclosure.

FIG. 3 is a non-limiting example of the structure of a smart transdermal drug delivery patch 300 comprising a layer of drug-in-adhesive. The smart patch 300 comprises a backing layer 310, a flex circuit 320, a flex-circuit liner 330, a drug containing layer 340, and a removable liner 350. When the smart patch is applied, the layers 310, 320, 330, 340 and 350 may be stacked over one another in a direction towards the patient skin.

As an outermost layer of the smart patch 300, the backing layer 310 may be impermeable to external substances and protect drug formulations in the smart patch from leaking. In some embodiments, the backing layer 310 may be stretchable and occlusive, which brings patient comfort and cosmetic appearance when the smart patch is applied.

The flex circuit 320 may be positioned between the outermost backing layer 310 and the flex circuit liner 330. In some embodiments, the flex circuit 320 may be a flexible circuit printed on the liner 330. The liner 330 may be an insulating film made of polyimide or polyester materials. The liner 330 may be configured to protect the drug-containing layer 340 from being in contact with the flex circuit 320. The flex circuit 320 may also comprise one or more of conductive layers, adhesive layers, and dielectric layers.

The drug-containing layer 340 may be a single layer. The drug-containing layer 340 may comprise a single drug-in-adhesive (DIA) layer, where the drug is dissolved or dispersed within adhesive. In some embodiments, the adhesive may comprise silicone, rubber, polyvinyl acetate or polyisobutylene, depending on the skin adhesion properties desired.

In some embodiments, the drug formulations that are suitable for use in the smart transdermal drug delivery patch may comprise drugs with a size amenable to transdermal delivery. For example, the drugs may have a size range of 100-200 Daltons, 100-300 Daltons, 100-500 Daltons, 100-800 Daltons, or 100-1000 Daltons. In other embodiments, depending on the skin permeabilization mechanisms in the smart patch, the drugs may comprise molecules with a size larger than 1000 Daltons.

In some embodiments, the drug formulations that are suitable for use in the smart transdermal drug delivery patch may comprise central nervous system (CNS) agents including antipsychotic agents (e.g., olanzapine), anti-smoking agents, anti-anxiety agents, antidepressants, anti-seizure agents, anti-coagulants, or agents for treating alcohol withdrawal syndrome.

In some embodiments, the antipsychotic agent can comprise olanzapine or a pharmaceutically effective salt thereof. Olanzapine has a structure of

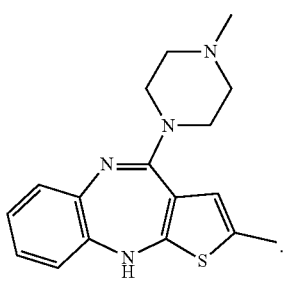 [SMILES: Cc1cc2c(s1)Nc1ccccc1N=C2N1CCN(C)CC1]

In some embodiments, the anti-seizure agent can comprise perampanel or a pharmaceutically effective salt thereof. Perampanel has a structure of

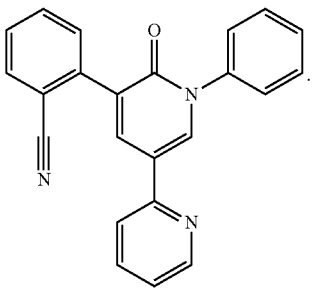 [SMILES: N#Cc1ccccc1-c1cc(-c2ccccn2)cn(-c2ccccc2)c1=O]

In some embodiments, the drug formulations that are suitable for use in the smart transdermal drug delivery patch may comprise an atrial fibrillation agent. In some embodiments, the atrial fibrillation agent can comprise rivaroxaban or a pharmaceutically effective salt thereof. Rivaroxaban has a structure of

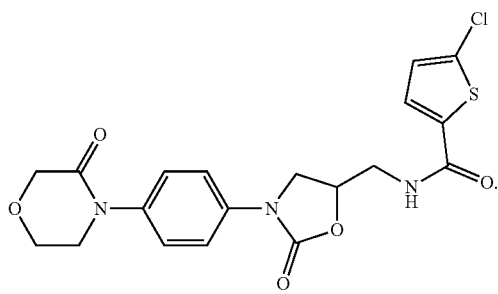 [SMILES: O=C(NCC1CN(c2ccc(N3CCOCC3=O)cc2)C(=O)O1)c1ccc(Cl)s1]

In some embodiments, the drug formulations that are suitable for use in the smart transdermal drug delivery patch may comprise anti-cancer drugs. The transdermal anti-cancer drugs may substitute oral drugs for cancer treatment with various advantages. For example, the transdermal anti-cancer drugs have an improved bioavailability that avoids the limiting first-pass effect by oral formulations in the gastrointestinal system resulting in a reduced concentration of the drugs upon reaching its site of action or the systemic circulation. The controlled release over hours and days ensures the dosage level remains stable, thereby improving the therapeutic effects of the drug. Non-limiting examples of anti-cancer drugs may comprise drugs treating cancers in adults and in children, including myeloma, breast cancer, renal cancer, etc.

In some embodiments, the drug formulations that are suitable for use in the smart transdermal drug delivery patch may comprise antineoplastic agents, non-steroidal anti-inflammatory drugs (NSAIDs), antibiotics, analgesics, anti-inflammatory agents, muscle relaxants, anti-epileptics, anti-ulcerative agents, anti-allergic agents, anti-nausea agents, cardiotonics, anti-arrhythmic agents, vasodilators, anti-hypertensive agents, anti-diabetic agents, anti-hyperlipidemics, anticoagulants, hemolytic agents, antituberculosis agents, hormones, narcotic antagonists, osteoclastic suppressants, osteogenic promoters, angiogenesis suppressors (antianginal), agents for neurodegenerative disease treatment, and various mixtures, salts, prodrugs and co-drugs thereof.

In some embodiments, the drug formulations that are suitable for use in the smart transdermal drug delivery patch may comprise large molecules such as vaccines, oligonucleotides, and peptides. These large molecule drugs may be hydrophilic drugs. For example, a variety of approaches for skin permeabilization may be utilized when applying the smart patch, including novel chemical enhancers, nanocarriers (e.g., solid lipid nanoparticles), ultrasound assisted methods (e.g., sonophoresis), electrically assisted methods (e.g., electroporation and iontophoresis), mechanically assisted methods (e.g., microneedles), thermal approaches (lasers and radio-frequency heating), etc. These approaches may allow a broader class of drugs to be effectively delivered through the skin. These approaches may also allow controlled release of drugs. For example, the smart patch may comprise an iontophoresis mechanism that generates a weak electric current and propels electrically charged drugs across skin into underlying tissues. Alternatively, the smart patch may comprise a sonophoresis mechanism that generates a low-frequency ultrasound wave that may temporarily increase skin permeability and enhances transdermal drug delivery.

In some embodiments, the drug-containing layer 340 may comprise a single drug. Alternatively, the drug-containing layer 340 may comprise two or more drugs. In some embodiments, the drug-containing layer 340 may comprise one or more placebos. During clinical trials, smart patches comprising placebos may be applied to a control group of participants, in comparison with an experimental group of participants to whom drug-containing smart patches are applied.

The drug-containing layer 340 may comprise excipients that may be characterized by functions, for example, solubilizers, penetration/permeation enhancers, retarders, and preservative/stabilizers. Non-limiting examples of excipients may comprise anti-adherent agents, anti-caking agents (e.g., additives such as silica or talc); antioxidants that prevent the oxidation and deterioration of components within the drug-containing layer. Non-limiting examples of antioxidants may comprise ascorbic acid, butylated hydroxyanisole (BHA), and BHT. Other examples of excipients may comprise buffering agents (e.g., sodium bicarbonate and calcium biphosphate) designed to maintain the pH value of the drug formulation, diluents/fillers (e.g., calcium carbonate and lactose), emulsifying agents that enhance the emulsion stability and avoids phase separation (e.g., simethicone emulsion, sodium lauryl sulfate, polysorbate 60), glidants added to drug formation in powder or granule forms to enhance the flowability (e.g., silica and silica derivatives), preservatives that prolongs the shelf life of the smart patch by protecting them from micro-organism deterioration (e.g., benzoic acid and butylparaben).

In some embodiments, the excipients may comprise one or more chemical enhancers. Chemical enhancers may temporarily dissolve stratum corneum and facilitate the transport of drug formulations to controlled depth in tissues. Chemical enhancers may comprise one or more of anionic surfactants, cationic surfactants, zwitterionic surfactants, nonionic surfactants, fatty acids, fatty esters, fatty amines, Azone-like compounds, sodium salts of fatty acids, sulphoxides and similar chemicals, pyrrolidones, essential oil, terpenes and terpenoids.

In some embodiments, the transdermal formulation may comprise an active ingredient in any suitable amount, such as 0.1 mg to 1 g.

As illustrated in FIG. 3, the smart patch 300 further comprises a liner 350. The liner 350 may protect the drug-in-adhesive and need to be removed prior to smart patch application.

Figure 4:
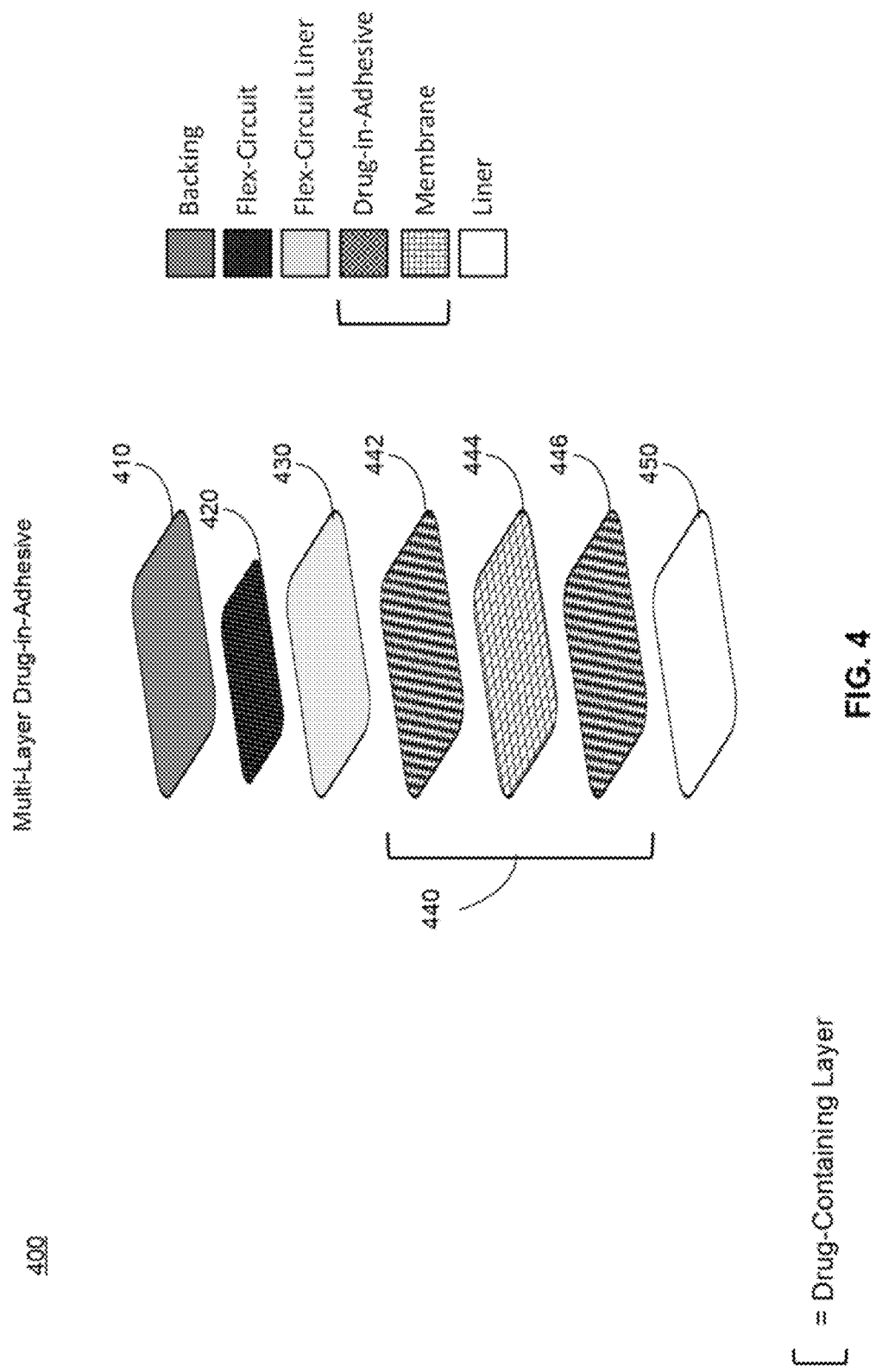
FIG. 4 illustrates the structure of a non-limiting example of smart transdermal drug delivery patch comprising a plurality of layers of drug-in-adhesive, according to some embodiments of the present disclosure.

FIG. 4 is a non-limiting example of the structure of a smart transdermal drug delivery patch 400 comprising a plurality of layers of drug-in-adhesive. The smart patch 400 comprises a backing layer 410, a flex circuit 420, a flex-circuit liner 430, a drug containing layer 440, and a removable liner 450. When the smart patch is applied, the layers 410, 420, 430, 440 and 450 may be overlapped with one another in a direction towards patient skin.

Different from the drug containing layer 340 comprising a single layer of drug-in-adhesive, the drug containing layer 440 comprises multiple layers of drug-in-adhesive. As illustrated, a first layer of drug-in-adhesive 442 is stacked over a second layer of drug-in-adhesive 446, with a membrane 444 positioned therebetween. Multiple layers of drug-in-adhesive may carry a larger amount of drug formulations, such that the use life of the smart patch may be substantially extended. The membrane 444 between the drug-in-adhesive layers 442 and 446 may control the diffusion of drugs for extended release. The membrane 444 may be made of natural or synthetic polymer or synthetic elastomers. The thickness of the membrane 444 may range from about 2 mm to about 7 mm.

Figure 5:
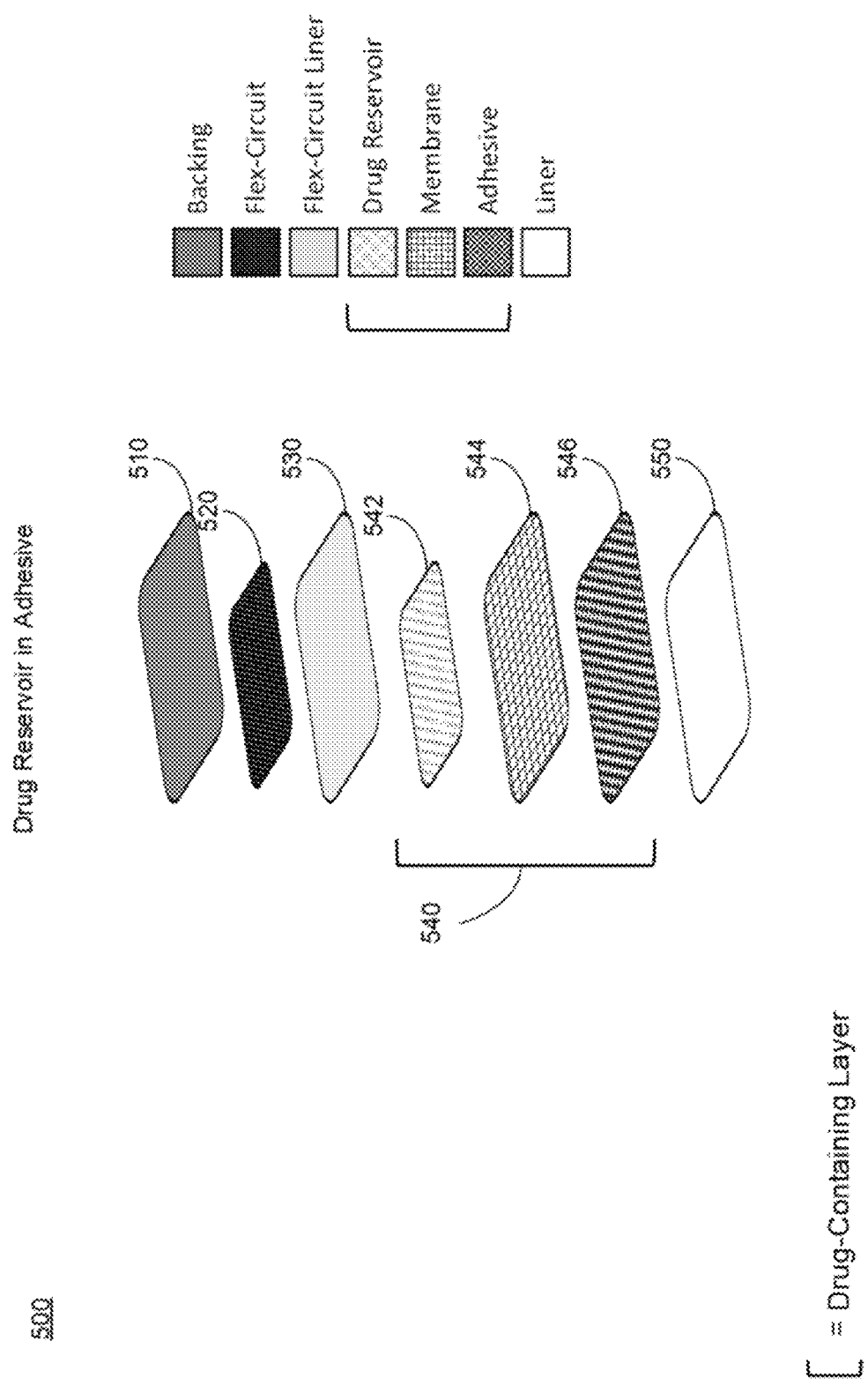
FIG. 5 illustrates the structure of a non-limiting example of smart transdermal drug delivery patch comprising a drug reservoir, according to some embodiments of the present disclosure.

FIG. 5 is a non-limiting example of the structure of a smart transdermal drug delivery patch 500 comprising a drug reservoir. The smart patch 500 comprises a backing layer 510, a flex circuit 520, a flex-circuit liner 530, a drug containing layer 540, and a removable liner 550. When the smart patch is applied, the layers 510, 520, 530, 540 and 550 may be overlapped with one another in a direction towards the patient skin.

The drug-containing layer 540 comprises a drug reservoir 542, a membrane 544, and an adhesive layer 546 overlapped with one another. Unlike drug-in-adhesive layer(s) that contain a mixture of drug and adhesive, here, the drug formulation is stored in the drug reservoir 542 and separate from the adhesive layer 546. The membrane 544 between the drug reservoir 542 and the adhesive layer 546 may control the diffusion of drugs for extended release. When the smart patch 500 is applied to the skin, the drug may slowly diffuse from the reservoir 542 through the rate-controlling membrane 544 and the adhesive 546 to the skin.

Figure 6:
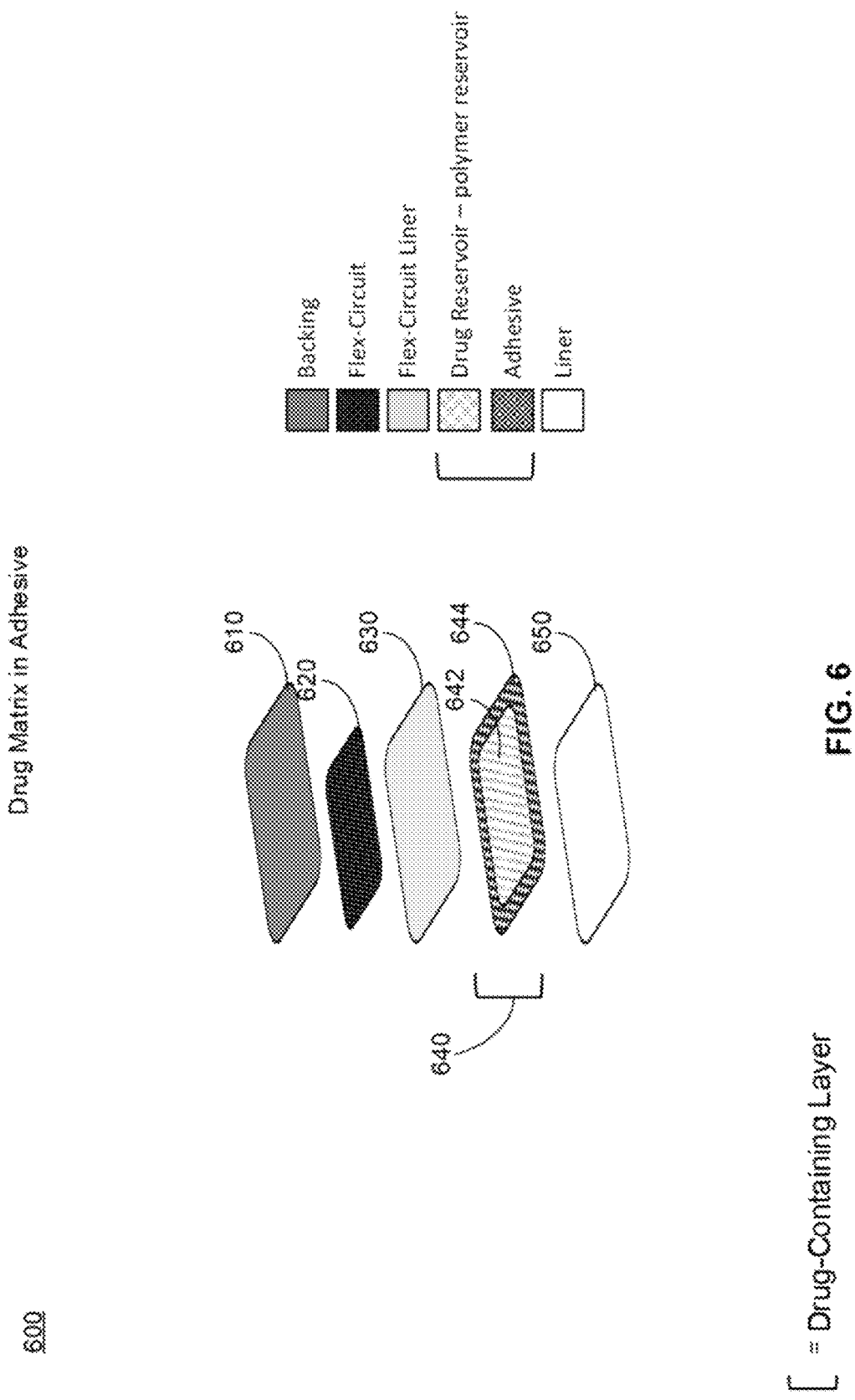
FIG. 6 illustrates the structure of a non-limiting example of smart transdermal drug delivery patch comprising a drug reservoir and an adhesive ring therearound, according to some embodiments of the present disclosure.

FIG. 6 is a non-limiting example of the structure of a smart transdermal drug delivery patch 600 comprising a drug reservoir and an adhesive ring therearound. The smart patch 600 comprises a backing layer 610, a flex circuit 620, a flex-circuit liner 630, a drug containing layer 640 and a removable liner 650. When the smart patch is applied, the layers 610, 620, 630, 640 and 650 may be overlapped with one another in a direction towards patient skin.

The drug-containing layer 640 comprises a drug reservoir 642 surrounded by an adhesive ring 644. In some embodiments, the drug reservoir 642 may comprise a drug-containing polymer matrix in direct contact with the skin. The drug reservoir 642 may include one or more cavities formed by a polymer structure and may include one or more ion exchange membranes (e.g., electroactive polymer membranes), semi-permeable membranes, porous membranes and/or gels that are capable of at least temporarily retaining an element or compound.

When the smart transdermal drug delivery patch comprises a drug reservoir as illustrated in FIGS. 5 and 6, the drugs that are suitable for use may have an expected dosage range to fit the size of the reservoir. For example, for a smart transdermal drug delivery patch with 24-170 hours of use life, a daily dosage range may be less than 50 mg, less than 45 mg, less than 40 mg, less than 35 mg, less than 30 mg, less than 25 mg, or less than 20 mg.

Figure 7:
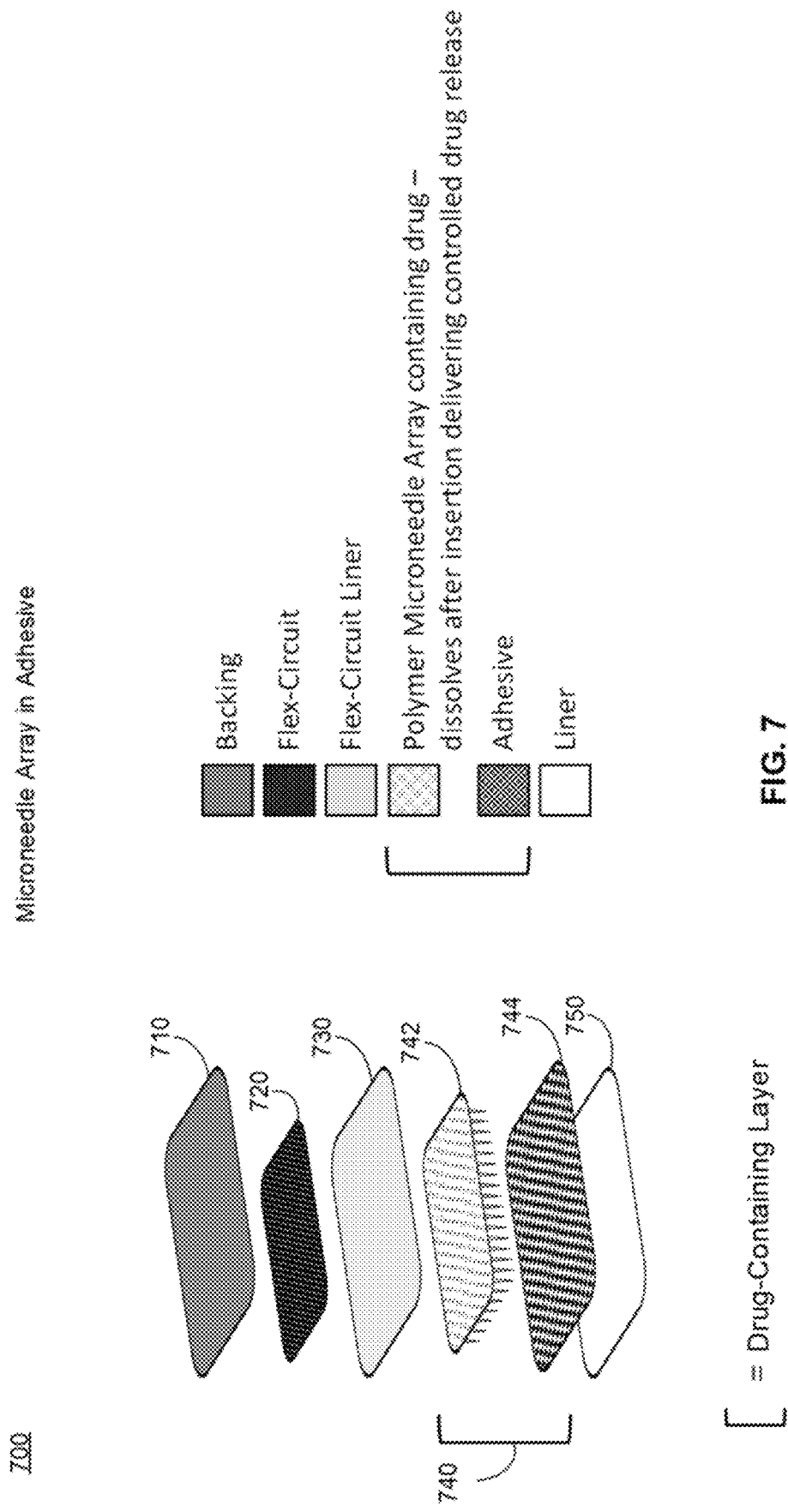
FIG. 7 illustrates the structure of a non-limiting example of smart transdermal drug delivery patch comprising a drug-containing microneedle array, according to some embodiments of the present disclosure.

FIG. 7 is a non-limiting example of the structure of a smart transdermal drug delivery patch 700 comprising a drug-containing microneedle array. The smart patch 700 comprises a backing layer 710, a flex circuit 720, a flex-circuit liner 730, a drug containing layer 740, and a removable liner 750. When the smart patch 700 is applied, the layers 710, 720, 730, 740 and 750 may be overlapped with one another in a direction towards the patient skin.

The drug-containing layer 740 comprises a microneedle array 742, in direct contact with the skin, with an adhesive layer 744. In some embodiments, the adhesive layer 744 may be surrounding the microneedles to adhere to the skin. The microneedles may pierce holes into the skin to increase transport by diffusion or iontophoresis or as drug carriers that release drug into the skin in a controllable manner. The microneedle array may substantially increase skin permeability and efficiency in the transdermal delivery, especially for hydrophilic molecules and macromolecules (e.g., peptides, DNA, RNA). In some embodiments, the microneedles may be made of polymer and dissolvable after pierced into the skin.

In some embodiments, the delivery of the drug from the TET platform is passive delivery. In some embodiments, the passive delivery of the drug from the TET platform begins upon attachment of the TET smart patch to the patient's skin. In some embodiments, the patch is not activated to release the drug by any signaling. In some embodiments' the drug is automatically delivered with no activation required.

Figure 8:
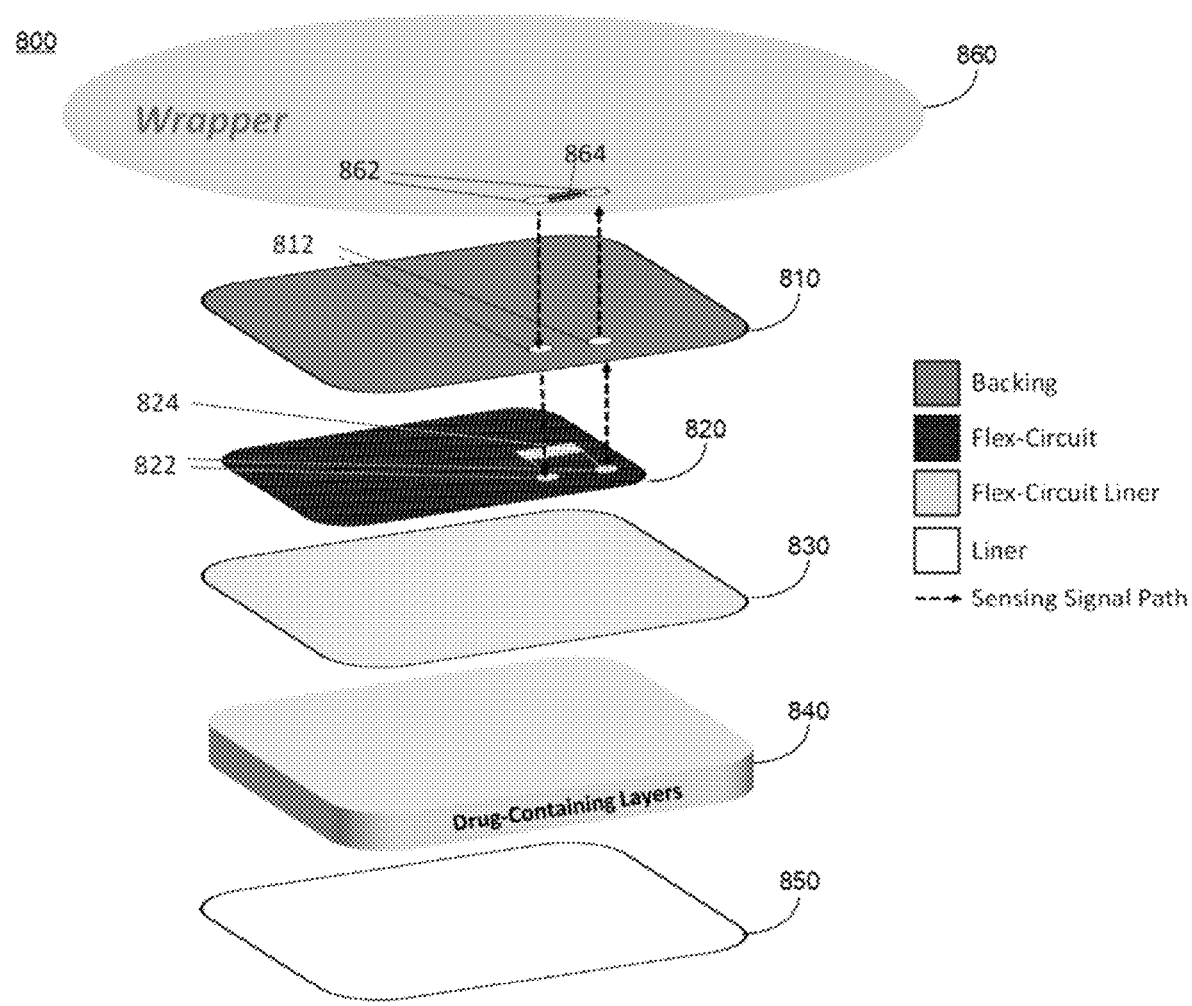
FIG. 8 illustrates the detection of a status change of the smart patch of removing a packaging from a smart transdermal drug delivery patch using one or more sensors, according to some embodiments of the present disclosure.

FIG. 8 illustrates detection of a status change of the smart patch of removing a packaging from a smart transdermal drug delivery patch 800 using one or more sensors. The smart patch 800 comprises a backing layer 810, a flex circuit 820, a flex circuit liner 830, a drug containing layer 840 and a removable liner 850. When the smart patch is applied, the layers 810, 820, 830, 840 and 850 may be overlapped with one another in a direction towards patient skin. The drug-containing layer 840 may be any of the drug-containing layers 340, 440, 540, 640, and 740 as illustrated in FIGS. 3-7. The smart patch 800 is packed by a removable wrapper 860.

As illustrated, the flex circuit 820 comprises one or more conducting pads 822 and sensors 824 (e.g., sensing circuit). The inner surface of the wrapper 860 is in contact with the backing layer 810 and comprises one or more conducting pads 862 and conducting traces 864 that are in electrical connection. One or more pass-through holes 812 are present on the backing layer 810. The positions of the pass-through holes 812 are aligned with the conducting pads 862 on the wrapper 860 and the conducting pads 822 on the flex circuit 820. When the wrapper 860 wraps around the smart patch 800, the conducting pads 862 and 822 are electrically connected via the conducting traces 864, thereby forming a sensing signal path. The flex circuit 820 may apply a voltage to the conducting pads 822, which induces a current measured by the sensors 824. When the patient removes the wrapper 860, the electrical connection is interrupted. The sensors 824 on the flex circuit 820 detects the current decrease caused by the disconnection. In some embodiments, the flex circuit can apply a voltage to the conducting pads constantly, or multiple times per second, once per second, multiple times per minute, once per minute, one or more times per about two minutes, one or more times per about five minutes, one or more times per about ten minutes, one or more times per about 15 minutes, one or more times per about 30 minutes, one or more times per about one hour, one or more times per about two hours, one or more times per about three hours, one or more times per about four hours, one or more times per about six hours, one or more times per about ten hours, one or more times per about twelve hours, one or more times per about 24 hours, one or more times per about 36 hours, one or more times per about 48 hours, one or more times per about one week, one or more times per about two weeks, one or more times per about one month, one or more times per about two months, one or more times per about three months, one or more times per about six months, one or more times per about twelve months, one or more times per about one year, or one or more times per about more than one year.

In response to the status change of the smart patch of removing the wrapper, the processor (e.g., processors 120 and 214 in FIGS. 1 and 2) may control the smart patch to transit between working conditions. In some embodiments, the processor may control the smart patch to transit from the hibernation mode, which is a default mode from manufacture, to a non-hibernation mode (e.g., sleep mode and work mode).

Figure 9:
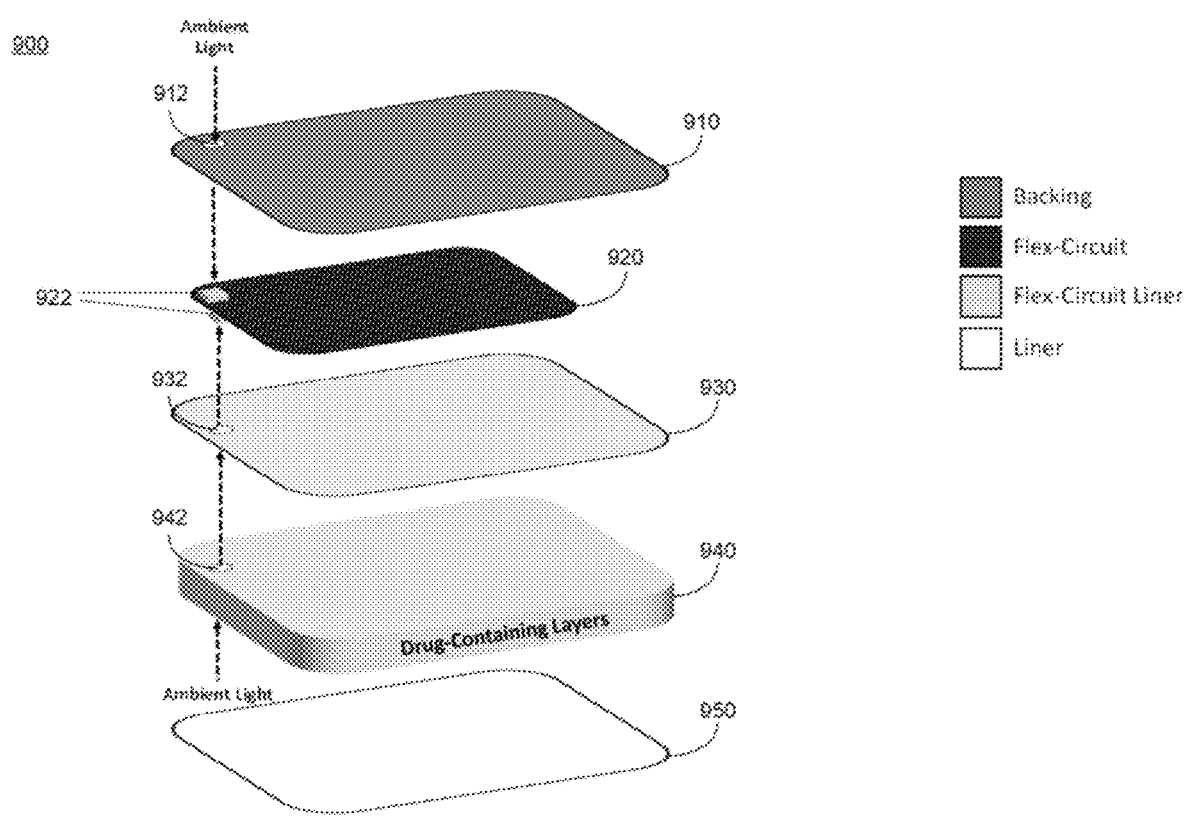
FIG. 9 illustrates the detection of a status change of the smart patch of opening a smart transdermal drug delivery patch using one or more optical sensors, according to some embodiments of the present disclosure.

FIG. 9 illustrates detection of a status change of the smart patch of opening a smart transdermal drug delivery patch 900 using one or more optical sensors. The smart patch 900 comprises a backing layer 910, a flex circuit 920, a flex-circuit liner 930, a drug containing layer 940, and a removable liner 950. When the smart patch is applied, the layers 910, 920, 930, 940 and 950 may be overlapped with one another in a direction towards patient skin. Each of the backing layers 910, flex circuit liner 930, and drug-containing layer 940 comprises one or more transparent windows (or pass-through holes) 912, 932, and 942, respectively. The flex circuit 920 comprises one or more optical sensors 922 aligned with the transparent windows 912, 932, and 942, such that ambient light may pass through from the transparent windows and be detected by the optical sensors 922.

The patient may open the smart patch prior to applying it to the skin by removing the packaging (e.g., wrapper) from the smart patch. The optical sensor 922 may detect ambient light passed through from the transparent window 912 upon the removal of the wrapper. In response to this status change of the smart patch, the processor may control the smart patch to remain the current working condition of the smart patch, for example, at the sleep mode or work mode. Alternatively, if the previous status change of the smart patch of removing the wrapper failed to "wake up" the smart patch, upon the opening of the smart patch, the processor may control the smart patch to transit from the hibernation mode to a non-hibernation mode.

In some embodiments, one or more sensors of a TET smart patch may activate in response to a package surrounding the TET smart patch or attached to the TET smart patch being manipulated or opened. In some embodiments, one or more sensors of the TET smart patch can be activated when a seal of a packaging surrounding the TET smart patch or attached to the TET smart patch is broken. In some embodiments, the TET smart patch can complete an electric circuit with a low-energy electrical current when in the packaging. In some embodiments, manipulating one or more parts of the packaging, like breaking a seal, peeling back a portion of the package, ripping or poking one or more parts of the package, or disconnecting a part of the package, for example, can activate the one or more sensors. The sensors can be, for example, light sensors, electricity sensors, pressure sensors, infrared sensors, sound sensors, ultrasound sensors, gas sensors, capacitive sensors, humidity sensors, touch sensors, temperature sensors, magnetic field sensors, resistive sensors, or any combination thereof.

The patient may further remove the liner 950 that covers the drug-containing layer 940. The optical sensor 922 may detect ambient light passed through the transparent windows 942 and 932 caused by the removal of the liner 950. The processor may control the smart patch to remain the current working condition, for example, at the sleep mode or work mode. Alternatively, if the previous status change of the smart patches failed to trigger the transition of working conditions, the processor may control the smart patch to transit to work mode.

Following the removal of the liner 950, the patient may apply the smart patch to her skin. Ambient light passing through the transparent window 942 may be blocked because the drug-containing layer 940 is in direct contact with the skin. The optical sensor 922 may detect the change in ambient light. The processor in the smart patch may control the working condition of the smart patch 900. For example, if the smart patch was at the sleep mode, when being applied to patient skin, the processor may control the smart patch to transit to the work mode.

In some embodiments, the flex circuit 920 may further comprise one or more optical sensors used as a real time calibrator and differential comparator to ensure reliable detection with variable lighting conditions. The optical sensors may be positioned on the flex circuit 920 and away from the transparent windows 912, 932, and 942, such that the calibration and differential comparison are not impacted by ambient light change caused by status change of the smart patch to the smart patch.

Figure 10:
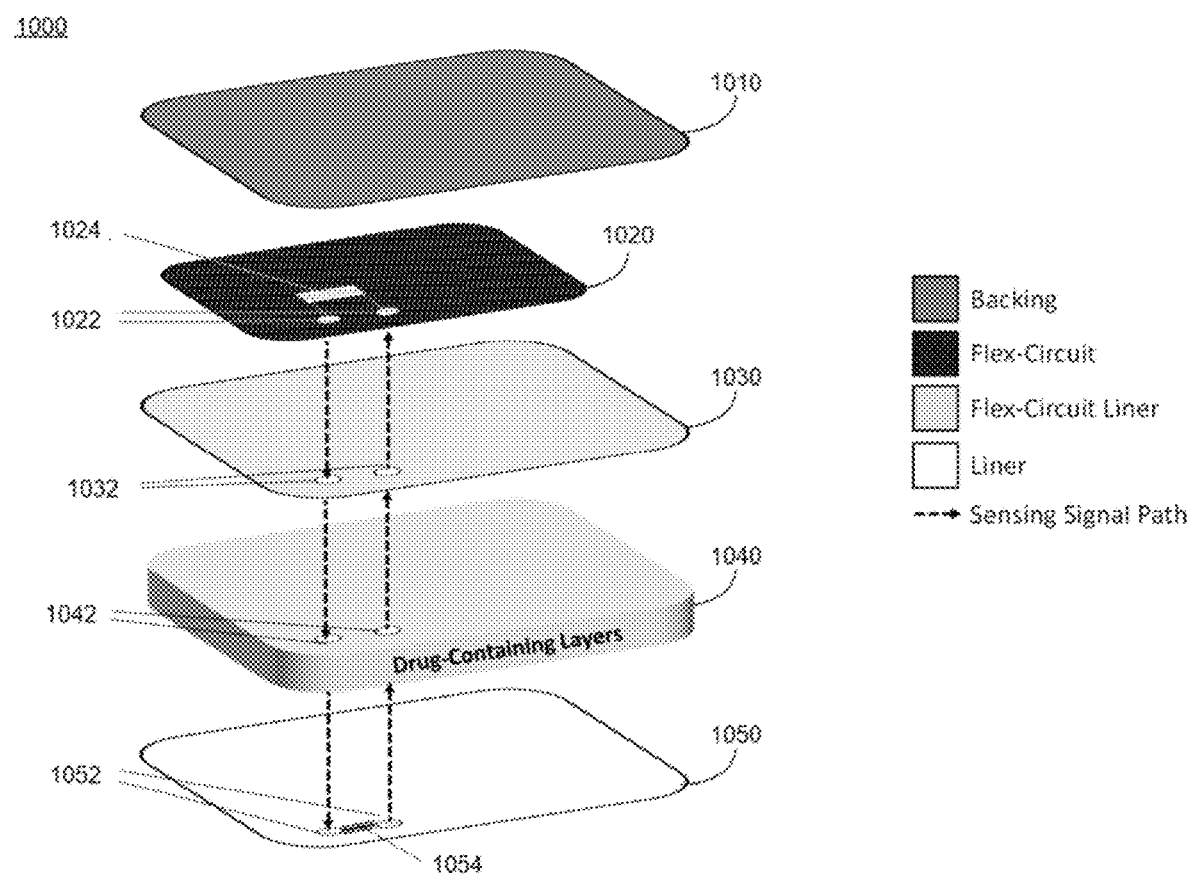
FIG. 10 illustrates the detection of a status change of the smart patch of removing a liner from a smart transdermal drug delivery patch using one or more sensors, according to some embodiments of the present disclosure.

FIG. 10 illustrates detection of a status change of the smart patch of removing a liner from a smart transdermal drug delivery patch 1000 using one or more sensors. The smart patch 1000 comprises a backing layer 1010, a flex circuit 1020, a flex-circuit liner 1030, a drug containing layer 1040, and a removable liner 1050. When the smart patch is applied, the layers 1010, 1020, 1030, 1040 and 1050 may be overlapped with one another in a direction towards patient skin. As illustrated, the flex circuit 1020 comprises one or more of conducting pads 1022 and sensors 1024 (e.g., sensing circuit). The inner surface of the liner 1050 is in direct contact with the drug-containing layer 1040 and comprises one or more of conducting pads 1052 and conducting traces 1054 that are in electrical connection. Pass-through holes 1032 and 1042 are present on the flex circuit liner 1030 and drug-containing layer 1040, respectively. The positions of the pass-through holes 1032 and 1042 are aligned with the conducting pads 1022 on the flex circuit 1020 and conducting pads 1052 on the liner 1050. When the liner 1050 is in direct contact with the drug-containing layer 1040, the conducting pads 1022 and 1052 are electrically connected via the conducting traces 1054, thereby forming a sensing signal path. The flex circuit 1020 may apply a voltage to the conducting pads 1022, which induces a current measured by the sensors 1024. When the patient removes the liner 1050, the electric connection is interrupted. The sensors 1024 on the flex circuit 1020 may detect the current decrease caused by the disconnection. The processor in the smart patch may control the smart patch to maintain the current working condition of the smart patch, for example, at the sleep mode or work mode. In some embodiments, the processor may control the smart patch to transit between working conditions.

Figure 11:
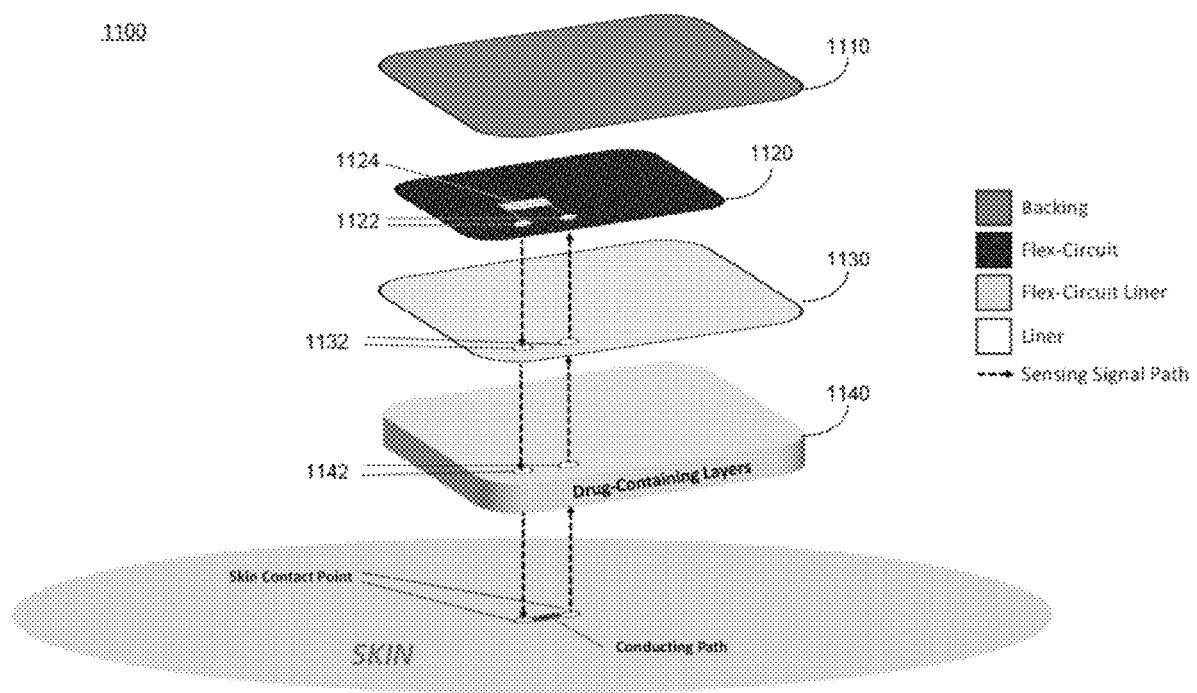
FIG. 11 illustrates the detection of a status change of the smart patch of applying a smart transdermal drug delivery patch to patient skin using one or more sensors, according to some embodiments of the present disclosure.

FIG. 11 illustrates detection of a status change of the smart patch of applying a smart transdermal drug delivery patch 1100 to patient skin using one or more sensors. The smart patch 1100 comprises a backing layer 1110, a flex circuit 1120, a flex-circuit liner 1130, and a drug containing layer 1140. When the smart patch is applied, the layers 1110, 1120, 1130, and 1140 may be overlapped with one another in a direction towards patient skin. In this scenario, both the wrapper (e.g., wrapper 860 in FIG. 8) and the liner (e.g., liner 850, 950, 1050 in FIGS. 8-10, respectively) are removed. The smart patch is ready to be applied to patient skin.

As illustrated, the flex circuit 1120 comprises conducting pads 1122 and sensors 1124 (e.g., sensing circuit). Pass-through holes 1132 and 1142 are present on the flex circuit liner 1130 and drug-containing layer 1140, respectively. The positions of the pass-through holes 1132 and 1142 are aligned with the conducting pads 1122 on the flex circuit 1120. When the smart patch is applied, the conducting pads 1122 are in direct contact with the skin (see skin contact point and conducting path in FIG. 11) through the pass-through holes 1132 and 1142. The conducting pads 1122 and the skin contact points form an electrical connection. When the flex circuit 1120 applies a voltage to the conducting pads 1122, a current may be generated and detected by the sensors 1124. In response, the processor may control the smart patch to transit between working conditions, for example, from sleep mode to work mode. Alternatively, if previous status change of the smart patches already triggered the smart patch to transit to work mode, the processor may maintain the working condition.

After the smart patch is applied, the processor may stay in sleep mode, which is a low-powered and default mode. Upon receiving a sensing event corresponding to a status change of the smart patch detected by the sensors, the processor may control the smart patch to transit from sleep mode to work mode. Alternatively or additionally, upon receiving a communication signal (e.g., an alert or message from other devices in the network) from the communication interface, the processor may control the smart patch to transit from sleep mode to work mode. In some embodiments, the smart patch in sleep mode can minimize power consumption and extend the use life of the smart patch. In some embodiments, the smart patch can receive a communication signal or sensing event multiple times per second, once per second, multiple times per minute, once per minute, one or more times per about two minutes, one or more times per about five minutes, one or more times per about ten minutes, one or more times per about 15 minutes, one or more times per about 30 minutes, one or more times per about one hour, one or more times per about two hours, one or more times per about three hours, one or more times per about four hours, one or more times per about six hours, one or more times per about ten hours, one or more times per about twelve hours, one or more times per about 24 hours, one or more times per about 36 hours, one or more times per about 48 hours, one or more times per about one week, one or more times per about two weeks, one or more times per about one month, one or more times per about two months, one or more times per about three months, one or more times per about six months, one or more times per about twelve months, one or more times per about one year, or one or more times per about more than one year.

In some embodiments, one or more communication signals can control the smart patch mode to improve battery performance. In some embodiments, one or more communication signals from the communication interface of the TET patch can cause the TET patch to exit sleep mode to improve performance at the expense of battery life. In some embodiments, work mode can increase battery power usage and improve performance of the TET patch. In some embodiments, sleep mode can decrease battery power usage and improve battery life of the printable battery of the TET system.

The present disclosure provides various mechanisms for improving the reliability of detecting and identifying status change of the smart patch to the smart patch, and based on the types of status change of the smart patch, controlling the smart patch to transit between working conditions.

In some embodiments, multiple pairs of conducting pads may be present on the flex circuit and packaging (e.g., wrapper and liner), and generate redundant signals that can be detected by the sensors. Moreover, a plurality of pairs of conducting pads on the flex circuit may monitor the electrodermal response of the patient wearing the smart patch. The smart patch may comprise algorithms stored in memory (e.g., System-on-a-Chip (SoC) embedded algorithms) for analyzing these electrodermal responses for clinical data collection and monitoring.

In some embodiments, the processor may determine whether the signals generated from different sensors are consistent and point to the same status change of the smart patch. When signal changes detected by different sensors are inconsistent, the process may generate an alert signal indicating inconsistent status change of the smart patch being identified or malfunction of the smart patch. For example, when the patient removes the wrapper from the smart patch, the electrical connection between the conducting pads 822/862 and conducting trace 864 no longer exists (see, e.g., FIG. 8). The sensors 824 may detect the current decrease, and the processor may identify the status change of the smart patch of removing the wrapper and control the smart patch to transit among working conditions. As the smart patch is exposed or opened, the optical sensor 922 may detect ambient light increase from the pass-through holes 912 in the backing layer (see, e.g., FIG. 9). When the light change is consistent with the electrical signal change, they may point to the same status change of the smart patch of removing the wrapper. The sensors can be, for example, light sensors, electricity sensors, piezoelectric sensors, pressure sensors, infrared sensors, sound sensors, ultrasound sensors, gas sensors, capacitive sensors, humidity sensors, touch sensors, temperature sensors, magnetic field sensors, or any combination thereof.

When the patient removes the liner and exposes the drug-containing layer, the electrical connection between the conducting pads 1022/1052 and conducting trace 1054 on the liner no longer exists (see, e.g., FIG. 10). The sensors 1024 may detect the current decrease, and the processor may identify the status change of the smart patch of removing the liner. The optical sensor 922 may detect ambient light increase from the pass-through holes 942 and 932 in the drug-containing layer and flex circuit liner (see, e.g., FIG. 9). The light change is consistent with the electrical signal change, pointing to the same status change of the smart patch of removing the liner.

When the patient applies the smart patch to her skin, an electrical connection is established between the skin contact points and the conducting pads 1122 on the flex circuit 1120 (see FIG. 11). The sensors 1124 may detect the current increase, and the processor may identify the status change of the smart patch of applying the smart patch. The optical sensor 922 may detect ambient light decrease because ambient light from the pass-through hole 942 on the drug-containing layer 940 is blocked by the skin (see, e.g., FIG. 9). The light change is consistent with the electrical signal change, pointing to the same status change of the smart patch of applying the smart patch.

When the patient removes the smart patch from her skin, the electrical connection between the skin contact points and the conducting pads on the flex circuit no longer exists. The sensors may detect the current decrease, and the processor may identify the status change of the smart patch of removing the smart patch and control the smart patch to transit between working conditions. The optical sensor may detect light increase as ambient light passes from the pass-through holes on the drug-containing layer and flex circuit liner. The light change is consistent with the electrical signal change, pointing to the same status change of the smart patch of removing the smart patch.

In some embodiments, the removal of the smart patch may be unintentional, for example, the smart patch may accidentally fall off the skin. When the patient re-applies the smart patch to her skin within a pre-determined time threshold, the electrical connection is reestablished between the skin contact points and the conducting pads on the flex circuit, and detected by the sensors. In consistency with the status change of the smart patch, the light sensor may detect light change when the smart patch is applied. The processor may control the smart patch to transit from sleep mode to work mode again. In some embodiments, one or more communication signals can control the smart patch mode to improve battery performance. In some embodiments, one or more communication signals from the communication interface of the TET patch can cause the TET patch to exit sleep mode to improve performance at the expense of battery life. In some embodiments, work mode can increase battery power usage and improve performance of the TET patch. In some embodiments, sleep mode can decrease battery power usage and improve battery life of the printable battery of the TET system. Nevertheless, when the duration of the removal exceeds the pre-determined time threshold, it may indicate the patient has either completed the dose or terminated the use of the smart patch. The processor may control the smart patch to transit to the hibernation mode.

The processor may further differentiate status change of the smart patch and ensure each action is accurately and reliably detected. The flex circuit may apply different voltages to the conducting pads and conducting traces on the circuit, thereby generating different magnitudes of current detected by the sensors. For example, the flex circuit may generate a larger current corresponding to the status change of the smart patch of removing the liner from the smart patch than the action of applying the smart patch to the skin. By differentiating status change of the smart patch, the processor may accurately control the working conditions of the smart patch in response to the actions.

Figure 12:
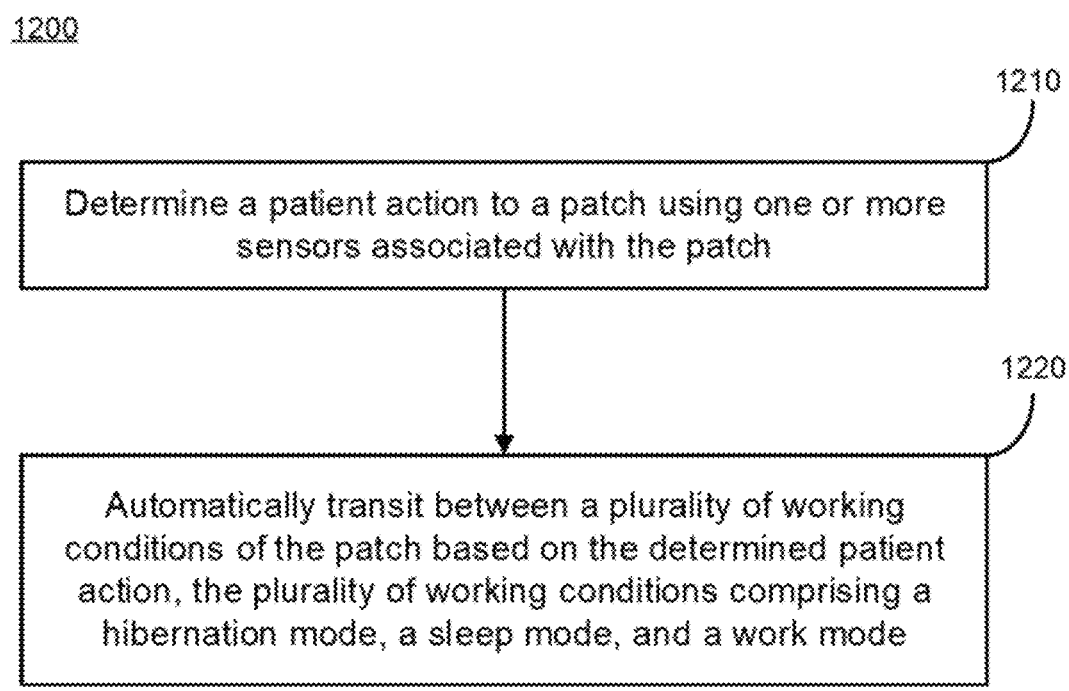
FIG. 12 illustrates a process of treating a patient in need thereof using a transdermal drug delivery smart patch, according to some embodiments of the present disclosure.

FIG. 12 illustrates a process 1200 of treating a patient in need thereof using a transdermal drug delivery smart patch. The process comprises determining a status change of the smart patch to a smart patch using one or more sensors associated with the smart patch (step 1210), and automatically transiting between a plurality of working conditions of the smart patch based on the determined status change of the smart patch (see step 1220). The plurality of working conditions may comprise a hibernation mode, a sleep mode, and a work mode.

Figure 13:
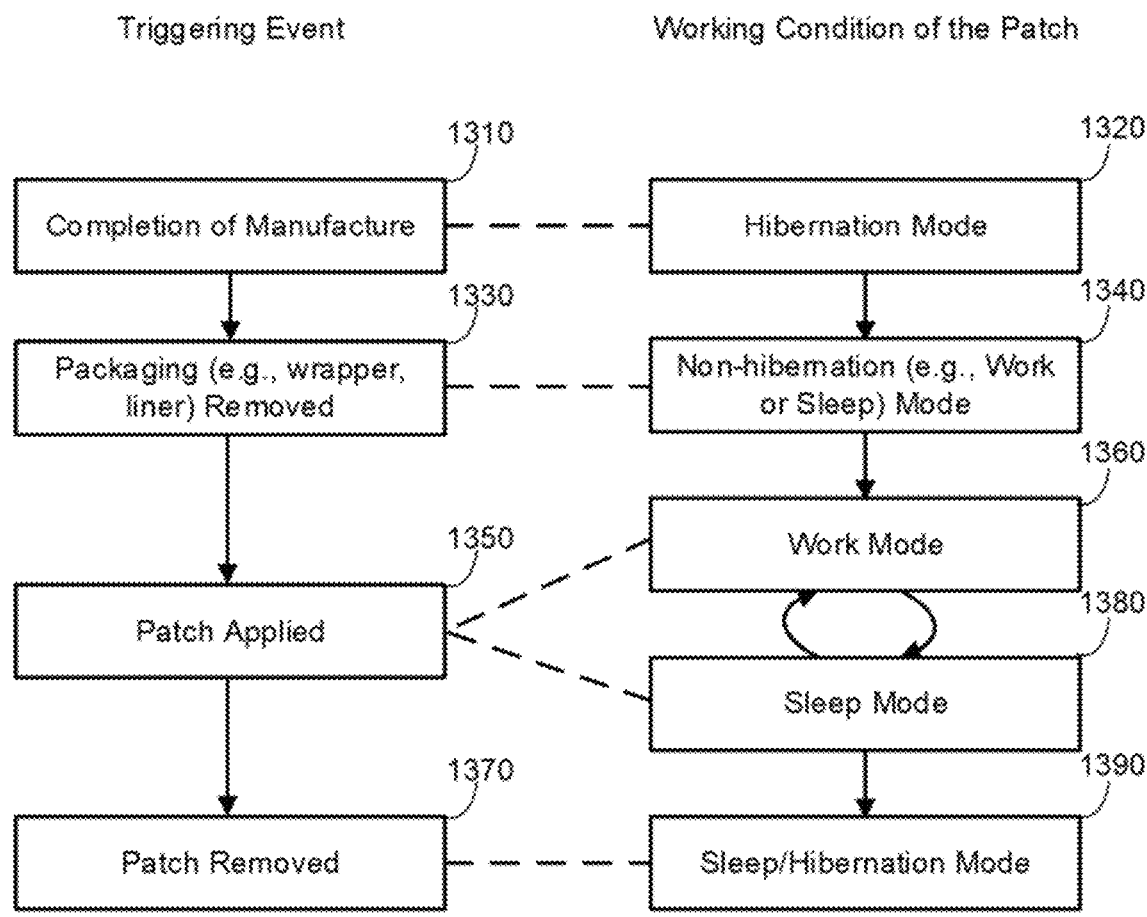
FIG. 13 illustrates correlations between triggering events and corresponding working conditions of a transdermal drug delivery smart patch, according to some embodiments of the present disclosure.

FIG. 13 illustrates correlations between triggering events and corresponding working conditions of a transdermal drug delivery smart patch. Upon completion of manufacture (see 1310), the smart patch is at hibernation mode (see 1320). The power of the smart patch is off. The smart patch does not send out or receive communication signals. Subsequently, a patient receives the smart patch and removes the packaging including the wrapper and liner from the smart patch (see 1330). The sensors within the smart patch detect these status change of the smart patches. Accordingly, the processor transits the smart patch from the hibernation mode to a non-hibernation mode, for example, sleep mode or work mode (see 1340). The patient subsequently applies the smart patch to her skin (see 1350), which is detected by the sensors in the smart patch. During the normal use of the smart patch, the smart patch may remain in sleep mode for energy saving purpose (see 1380). When the sensors detect another status change of the smart patch on the smart patch or receives a communication signal via the communication interface, the processor may control the smart patch to transit from sleep mode to work mode (see 1360). Alternatively, the processor may control the smart patch to switch between the sleep mode and the work mode periodically. When the smart patch is switched to the work mode, the processor may transmit smart patch usage data, a current working condition of the smart patch, transitions of working conditions, a state of sensors, a sequence of state changes, date and time stamp of each state change, a unique smart patch identifier via the communication interface. When the patient removes the smart patch (see 1370), depending on the duration of the removal, the smart patch may stay at the sleep mode or transit to the hibernation mode (see 1390). In some embodiments, one or more communication signals can control the smart patch mode to improve battery performance. In some embodiments, one or more communication signals from the communication interface of the TET patch can cause the TET patch to exit sleep mode to improve performance at the expense of battery life. In some embodiments, work mode can increase battery power usage and improve performance of the TET patch. In some embodiments, sleep mode or hibernation mode can decrease battery power usage and improve battery life of the printable battery of the TET system.

The present disclosure further provides a method of enhancing drug compliance of a patient in need thereof using a transdermal drug delivery smart patch. In some embodiments, enhancing drug compliance can comprise increasing compliance with a medication protocol. In some embodiments, enhancing drug compliance can comprise increasing a probability that a patient will comply with a treatment. In some embodiments, enhancing drug compliance can comprise increasing the percentage of a population that comply with a treatment protocol.

The method may comprise receiving, from the smart patch via a wireless network, information associated with a plurality of working conditions of the smart patch. The method may further comprise generating smart patch usage data based on the plurality of working conditions of the smart patch, wherein the smart patch usage data comprises at least one of a status change of the smart patch to the smart patch, a dose of a drug administered to the patient, a timing of the dose, or a frequency of doses. The status change of the smart patch may comprise one or more of removing a packaging from the smart patch, applying the smart patch to skin of the patient, and removing the smart patch from the skin of the patient.

The present disclosure further provides a method of monitoring drug compliance of a patient in need thereof using a transdermal drug delivery smart patch. In some embodiments, monitoring drug compliance can comprise monitoring compliance of the patient with a medication protocol at a single time point. In some embodiments, monitoring drug compliance can comprise monitoring compliance of the patient with a medication protocol at multiple time points. In some embodiments, monitoring drug compliance can comprise monitoring compliance of more than one patient with a medication protocol at a single time point or at multiple time points. In some embodiments, monitoring drug compliance can comprise aggregating drug compliance data for a population over one time point or multiple time points. The method may comprise receiving, from the smart patch via a wireless network, information associated with a plurality of working conditions of the smart patch. The method may further comprise generating smart patch usage data based on the plurality of working conditions of the smart patch, wherein the smart patch usage data comprises at least one of a status change of the smart patch to the smart patch, a dose of a drug administered to the patient, a timing of the dose, or a frequency of doses. The status change of the smart patch may comprise one or more of removing a packaging from the smart patch, applying the smart patch to skin of the patient, and removing the smart patch from the skin of the patient.

The present disclosure further provides a transdermal drug delivery system comprising a smart transdermal drug delivery patch and a backend application system comprising one or more computer processors that are individually or collectively programmed to perform operations. The smart patch comprises a drug-containing layer, a communication interface, one or more sensors configured to detect a status change of the smart patch to the smart patch, and a processor communicatively coupled to the one or more sensors and the communication interface. The status change of the smart patch comprises one or more of removing a packaging from the smart patch, applying the smart patch to skin of the patient, and removing the smart patch from the skin. The processors in the backend application system are programmed to perform operations comprising receiving, from the smart patch, information associated with the plurality of working conditions of the smart patch via the wireless network, generating smart patch usage data based on the plurality of working conditions of the smart patch, wherein the smart patch usage data comprises one or more of the status change of the smart patches, a dose of a drug administered to the patient, a timing of the dose, or a frequency of doses, and determining drug compliance of the patient based on the smart patch usage data and the medical record of the patient saved on the wireless network.

Figure 14:
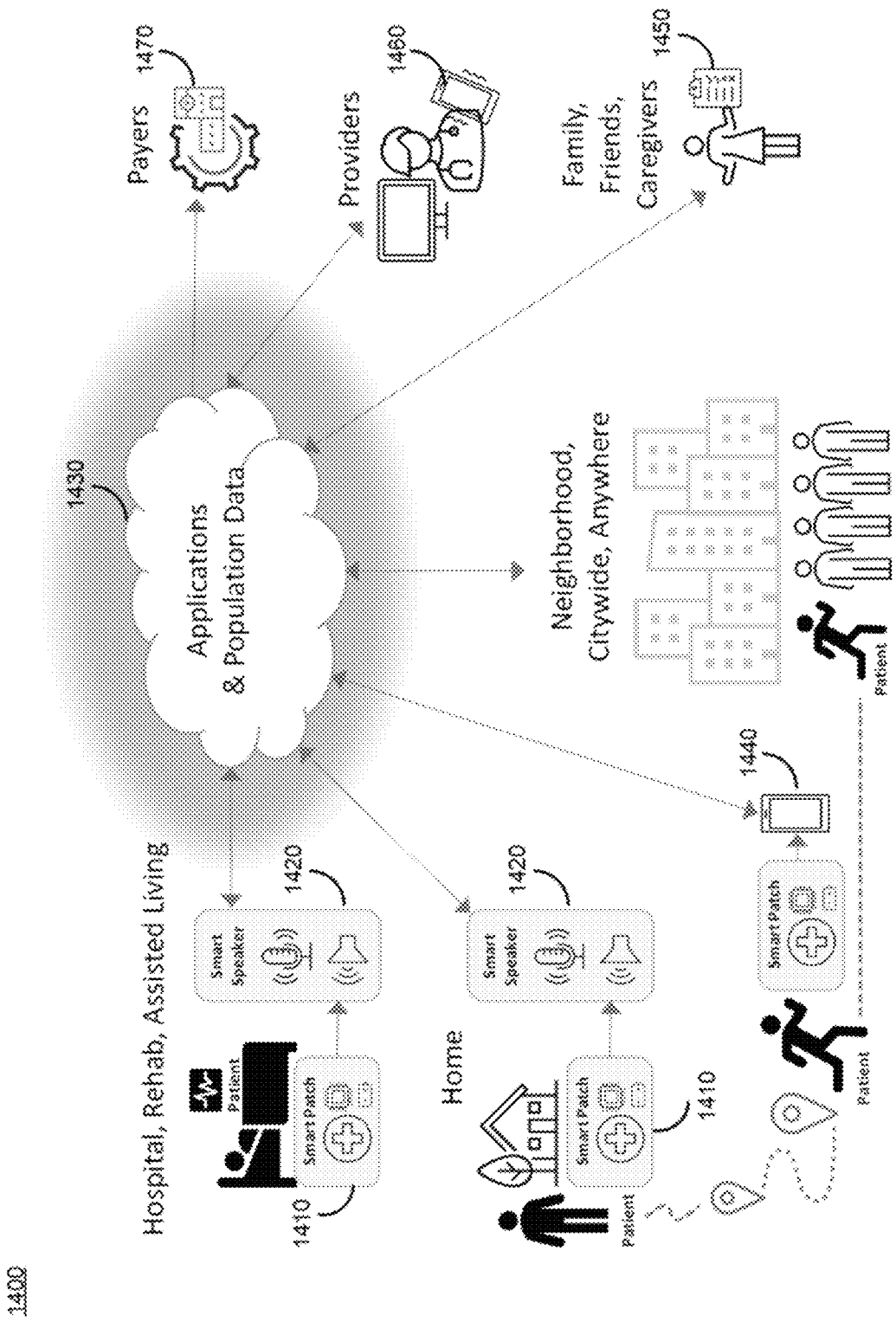
FIG. 14 illustrates a smart transdermal drug delivery patch connected to a wireless network, according to some embodiments of the present disclosure.

FIG. 14 illustrates a smart transdermal drug delivery patch connected to a wireless network. A networked system 1400 comprises one or more smart patches 1410 as described herein, and a plurality of user devices that are connected to a network 1430. The user devices comprise patient devices 1420 and 1440, devices 1450 and 1460 associated with caregivers and health care providers, and devices 1470 associated with business operators (e.g., insurance and pharmacy) associated with the patient healthcare.

In some embodiments, the smart patch 1410 may be connected in a mesh network. In other embodiments, the smart patch 1410 may be connected in an Internet-of-Things (IoT) network. As illustrated, the smart patch 1410 is connected with patient home devices 1420 and mobile devices 1440 via the network. The home devices may comprise personal assistance and home assistance devices including speakers, displays, phones, tablets, phablets, watches, glasses, and other personal and home electronics. The smart patch 1410 may transmit to and receive signals on the IoT network via the communication interface. The smart patch 1410 may transmit smart patch usage data to other devices (e.g., mobile devices 1440) in the network, including but not limited to status change of the smart patch, a dose of the drug, an overdose of the drug, a missed dose, an aborted dose, a timing of the dose, a frequency of doses, a current working condition of the smart patch, transitions of working conditions of the smart patch, a state of the sensors in the smart patch, a sequence of state changes of the sensors, a timing of each state change, a unique smart patch identifier.

The smart patch 1410 may be connected to the network using a communication protocol selected from the group consisting of Bluetooth, Wi-Fi, ZigBee, Thread, Z-Wave, LoRa, Near Field Communication (NFC), Broadband, Narrow Band-Internet of Things (NB-IoT), Radio Frequency Identification System (RFID), WLAN, 3G, 4G, and 5G, and future revisions of the aforementioned protocol standards. In some embodiments, the communication interface of the smart patch may comprise a Bluetooth Low Energy (BLE) radio (e.g., 216 as illustrated in FIG. 2), which communicates with other devices in the network via BLE.

In some embodiments, the smart patch 1410 may be compatible with Amazon Sidewalk, a low-bandwidth and long-range wireless communication protocol that uses BLE for short distance communication and LoRa for longer distance communication. The smart patch 1410 may transmit signals to in-range compatible devices, including mobile devices, trackers (e.g., Apple AirTags, Tile), smart speakers (e.g., Amazon Echo), and home assistance devices (e.g., Amazon Ring). As the patient wearing the smart patch is on the move, her mobile device may transmit geolocation data of the patient/smart patch to the network periodically.

The present disclosure further provides a backend application system comprising one or more computer processors that are individually or collectively programmed to perform operations for enhancing drug compliance of patients who use transdermal drug delivery smart patches. In some embodiments, enhancing drug compliance can comprise increasing compliance with a medication protocol. In some embodiments, enhancing drug compliance can comprise increasing a probability that a patient will comply with a treatment. In some embodiments, enhancing drug compliance can comprise increasing the percentage of a population that comply with a treatment protocol.

The present disclosure further provides a backend application system comprising one or more computer processors that are individually or collectively programmed to perform operations for monitoring drug compliance of patients who use transdermal drug delivery smart patches. In some embodiments, monitoring drug compliance can comprise monitoring compliance of the patient with a medication protocol at a single time point. In some embodiments, monitoring drug compliance can comprise monitoring compliance of the patient with a medication protocol at multiple time points. In some embodiments, monitoring drug compliance can comprise monitoring compliance of more than one patient with a medication protocol at a single time point or at multiple time points. In some embodiments, monitoring drug compliance can comprise aggregating drug compliance data for a population over one time point or multiple time points.

The backend application system and the smart patch may be connected to a wireless network, where the backend application may receive and process smart patch usage data from the smart patch, and determine whether the patient adheres to her drug administration. The backend application system may comprise a cloud computing system. Alternatively, the backend application system may comprise a computing system in other user devices in the network. Patients, health care providers/caregivers, and business operators may access smart patch usage data, and drug compliance information from web application, mobile application, or the like.

The backend application system may receive patient data from the network. The patient data may comprise clinical data, including but not limited to drug prescription, an expected dosage, an expected timing of administering the drug. The clinical data may also comprise an electronic health record (EHR) and demographic information of the patient stored in the network. The backend application system may receive smart patch usage data from the network. In some embodiments, the smart patch usage data may comprise smart patch actions to the smart patch, a current working condition of the smart patch, transitions of working conditions of the smart patch, a state of the sensors in the smart patch, a sequence of state changes and a timing of each state change. Based on the smart patch usage data, the backend application system may determine a timing of a dose (i.e., when the patient applies the smart patch), the duration of the smart patch application, a dose of the drug based on the duration of the smart patch use, any interruption during the smart patch use, a frequency of doses, etc.

In some embodiments, by comparing the patient's smart patch usage data and clinical data, the backend application system may determine the drug compliance of the patient. For example, when the drug prescription and expected dosage of a drug are inconsistent with the smart patch use, the backend application system may determine it is likely that the patient misses a dose, shortens or terminates a dose, overdoses, or otherwise fails to follow a scheduled course of treatment. The backend application system may generate and transmit an alert signal to the patient device (e.g., smart speaker 1420 and mobile device 1440), requesting drug compliance from the patient. In addition, the backend application system may transmit the alert signal to other user devices in the network including caregiver devices 1450, health care provider devices 1460 and business operator devices 1470 for monitoring the patient's drug compliance and medical record keeping.

In some embodiments, the backend application system may monitor the health condition of the patient during the smart patch use and intervene when necessary. When the patient wears an in-network device that measures physiological parameters of the patient, or a device that monitors geolocation, physical activity, and motion of the patient, these devices may transmit data associated with the patient to the network. Based on the received smart patch usage data and patient data, the backend application system may determine the change in the patient's health condition. For example, the patient may have an adverse drug reaction to the drug, which is reflected as a rapid change in her physiological parameters. The patient may suffer a sudden fall during the smart patch use or perform physical activities that are incompatible with the current drug administration, both of which can be monitored by motion sensors. The backend application system may generate and transmit an alert or intervention message to the patient device (e.g., smart speaker 1420 and mobile device 1440), providing suggestions or assistance to the patient. In addition, the backend application system may transmit the alert signal to other user devices in the network, such health care providers may provide urgent care in a timely manner.

In some embodiments, when user devices are connected to the network, the backend application system may provide authorized users access to the patient's record of smart patch use, along with medical record and other associated information. For example, the backend application system may provide smart patch usage data, drug compliance information, notifications (e.g., alerts or intervention messages) to the patient devices, such that the patient can easily monitor her drug administration and compliance on her mobile or web application, with an improved user experience. The backend application system may send smart patch usage data and drug compliance information to caregivers and health providers. Because smart patch usage data accurately reflects drug compliance of the patient and is generated automatically, caregivers and health providers can monitor the drug compliance and health conditions of the patient in real time. The indirect monitoring relying on questionnaires and patient self-reports can be avoided. Furthermore, as the backend application system receives and processes both smart patch usage data from the smart patch and clinical responses (e.g., real time physiological parameters) from other devices in the network, the backend application system may provide a direct assessment of drug compliance. Patients do not need to go to hospitals and clinics to measure drug/metabolite levels for drug adherence assessment.

In some embodiments, notifications can comprise push notifications, text messages, calls, emails, banners, in-app alerts, voice alerts, audio tones, spoken alerts, or other sounds, visual signals, light signals, vibration signals such as vibration of one or more technological devices, electrical current signals across the skin or a device, or physical manipulation of one or more objects.

In some embodiments, notifications can be provided for misuse of the smart patch, misuse of one or more medications, one or more missed medication schedules, application of too many smart patches, application of too few smart patches, application of one or more incorrectly medicated smart patches, application of one or more expired medication smart patches, application of one or more defective smart patches, application of one or more smart patches to an incorrect area of the body, application of one or more smart patches for a time period that is too short, application or one or more smart patches for a time period that is too long, accidental detachment of one or more smart patches from the skin, intentional detachment of one or more smart patches from the skin, incomplete application of one or more smart patches, damage to one or more smart patches, application of one or more smart patches with incorrect dosage of medication, application of one or more smart patches with incomplete or incorrect accompanying validation or security information, or another type of notification.

In some embodiments, notifications can be provided to authorized users. Authorized users can include relatives of the patient, friends of the patient, or care providers of the patient. Care providers of the patient can include medical personnel such as the patient's physician team, at-home care team, nursing team, nursing home staff, or other healthcare worker(s).

In some embodiments, the networked system 1400 may provide data storage functions. The network system 1400 may comprise one or more databases that store information associated with patients, including smart patch usage data, electronic health record (e.g., diagnoses, medicines, tests, allergies, immunizations, and treatment plans), physiological parameters and activities obtained from wearable devices, social history (e.g., alcohol and tobacco use), demographic information, mental health conditions, insurance information, and the like. The backend application system may analyze smart patch usage data in combination with other patient associated data stored in the network and determine the drug compliance of the patient in an efficient and effective manner.

Computer System

As described in some of the aforementioned embodiments, the smart patch and backend application system may comprise a computer system, including one or more processors, memory, and storage that communicate with each other, and with other components, via a bus. The computer system may have any suitable physical form, including but not limited to one or more integrated circuits (ICs), printed circuit boards (PCBs), mobile handheld devices (such as mobile telephones or PDAs), laptop or notebook computers, distributed computer systems, computing grids, or servers.

The computer system includes one or more processor(s) (e.g., central processing units (CPUs), general purpose graphics processing units (GPGPUs), or quantum processing units (QPUs)) that carry out functions. The processor(s) optionally contains a cache memory unit for temporary local storage of instructions, data, or computer addresses. The processor(s) are configured to assist in execution of computer readable instructions. The computer system may provide functionality for the components depicted in FIGS. 1-14 as a result of the processor(s) executing non-transitory, processor-executable instructions embodied in one or more tangible computer-readable storage media. The computer-readable media may store software that implements particular embodiments, and the processor(s) may execute the software. Memory may read the software from one or more other computer-readable media or from one or more other sources through a suitable interface, such as a network interface. The software may cause processor(s) to carry out one or more processes or one or more steps of one or more processes described or illustrated herein. Carrying out such processes or steps may include defining data structures stored in memory and modifying the data structures as directed by the software.

In addition or as an alternative, the computer system may provide functionality as a result of logic hardwired or otherwise embodied in a circuit, which may operate in place of or together with software to execute one or more processes or one or more steps of one or more processes described or illustrated herein. Reference to software in this disclosure may encompass logic, and reference to logic may encompass software. Moreover, reference to a computer-readable medium may encompass a circuit (such as an IC) storing software for execution, a circuit embodying logic for execution, or both, where appropriate. The present disclosure encompasses any suitable combination of hardware, software, or both.

Those of skill in the art will appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by one or more processor(s), or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In accordance with the description herein, suitable computing devices include, by way of non-limiting examples, server computers, desktop computers, laptop computers, notebook computers, netbook computers, netpad computers, handheld computers, Internet appliances, mobile smartphones, and tablet computers. Those of skill in the art will also recognize that select televisions, video players, and digital music players with optional computer network connectivity are suitable for use in the system described herein. Suitable tablet computers, in various embodiments, include those with booklet, slate, and convertible configurations, known to those of skill in the art.

In some embodiments, the computing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD, Linux, Apple Mac OS X Server, Oracle Solaris, Windows Server, and Novell NetWare. Those of skill in the art will recognize that suitable personal computer operating systems include, by way of non-limiting examples, Microsoft Windows, Apple Mac OS X, UNIX, and UNIX-like operating systems such as GNU/Linux. In some embodiments, the operating system is provided by cloud computing.

Non-Transitory Computer Readable Storage Medium

In some embodiments, the platforms, systems, media, and methods disclosed herein include one or more non-transitory computer readable storage media encoded with a program including instructions executable by the operating system of an optionally networked computing device. In further embodiments, a computer readable storage medium is a tangible component of a computing device. In still further embodiments, a computer readable storage medium is optionally removable from a computing device. In some embodiments, a computer readable storage medium includes, by way of non-limiting examples, CD-ROMs, DVDs, flash memory devices, solid state memory, magnetic disk drives, magnetic tape drives, optical disk drives, distributed computing systems including cloud computing systems and services, and the like. In some cases, the program and instructions are permanently, substantially permanently, semi-permanently, or non-transitorily encoded on the media.

Computer Program

In some embodiments, the platforms, systems, media, and methods disclosed herein include at least one computer program, or use of the same. A computer program includes a sequence of instructions, executable by one or more processor(s) of the computing device's CPU, written to perform a specified task. Computer readable instructions may be implemented as program modules, such as functions, objects, Application Programming Interfaces (APIs), computing data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft.NET or Ruby on Rails (RoR). In some embodiments, a web application utilizes one or more database systems including, by way of non-limiting examples, relational, non-relational, object oriented, associative, XML, and document oriented database systems. In further embodiments, suitable relational database systems include, by way of non-limiting examples, Microsoft SQL Server, mySQL, and Oracle. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous JavaScript and XML (AJAX), Flash ActionScript, JavaScript, or Silverlight. In some embodiments, a web application is written to some extent in a server-side coding language such as Active Server Pages (ASP), ColdFusion, Perl, Java, JavaServer Pages (JSP), Hypertext Preprocessor (PHP), Python, Ruby, Tcl, Smalltalk, WebDNA, or Groovy. In some embodiments, a web application is written to some extent in a database query language such as Structured Query Language (SQL). In some embodiments, a web application integrates enterprise server products such as IBM Lotus Domino. In some embodiments, a web application includes a media player element. In various further embodiments, a media player element utilizes one or more of many suitable multimedia technologies including, by way of non-limiting examples, Adobe Flash, HTML 5, Apple QuickTime, Microsoft Silverlight, Java, and Unity.

Mobile Application

In some embodiments, a computer program includes a mobile application provided to a mobile computing device. In some embodiments, the mobile application is provided to a mobile computing device at the time it is manufactured. In other embodiments, the mobile application is provided to a mobile computing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java, JavaScript, Pascal, Object Pascal, Python, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android SDK, BlackBerry SDK, BREW SDK, Palm OS SDK, Symbian SDK, webOS SDK, and Windows Mobile SDK.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java, Lisp, Python, Visual Basic, and VB .NET, or combinations thereof. Compilation is often performed, at least in part, to create an executable program. In some embodiments, a computer program includes one or more executable complied applications.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, a distributed computing resource, a cloud computing resource, or combinations thereof. In further various embodiments, a software module comprises a plurality of files, a plurality of sections of code, a plurality of programming objects, a plurality of programming structures, a plurality of distributed computing resources, a plurality of cloud computing resources, or combinations thereof. In various embodiments, the one or more software modules comprise, by way of non-limiting examples, a web application, a mobile application, a standalone application, and a distributed or cloud computing application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on a distributed computing platform such as a cloud computing platform. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for storage and retrieval of, by way of examples, image, cell state, protocol, and culture condition information. In various embodiments, suitable databases include, by way of non-limiting examples, relational databases, non-relational databases, object-oriented databases, object databases, entity-relationship model databases, associative databases, XML databases, document-oriented databases, and graph databases. Further non-limiting examples include SQL, PostgreSQL, MySQL, Oracle, DB2, Sybase, and MongoDB. In some embodiments, a database is Internet-based. In further embodiments, a database is web-based. In still further embodiments, a database is cloud computing based. In a particular embodiment, a database is a distributed database. In other embodiments, a database is based on one or more local computer storage devices.

Tech-Enabled Therapeutics (TET) Platform Architecture

In some embodiments, the present disclosure provides a tech-enabled therapeutics (TET) platform that can utilize next generation transdermal smart patches to deliver drugs with improved efficacy and tolerability. The TET platform can work with ultra-low power custom microcircuitry embedded in the transdermal smart patch that can track usage, connect to the cloud, and enable immediate interventions by caregivers with real time alerts when a dosage is missed.

This proactive health, wearable solution has massive opportunity to protect quality of life with preventative interventions, while building the first large-scale database with direct measurement of medication dosing patterns. Big data analytics may provide new insights on the effects of dosing patterns on treatment outcomes, impacting pharmaceutical formulations as well as clinical and prescribing practices.

The TET platform may enhance healthcare outcomes through a combination of innovative technology, data integration, and user-centric applications. The operation of the TET platform may depend on the interaction between smart transdermal smart patches, a cloud-based infrastructure (or a cloud platform), and client application platforms (or user applications).

In some embodiments, a TET smart patch may comprise or operatively couple to one or more sensors. In some embodiments, a TET smart patch may comprise or operatively couple to one or more sensors and one or more signaling modules. In some embodiments, a TET smart patch may comprise or operatively couple to one or more sensors and a Bluetooth Low Energy (BLE) module. The one or more sensors may detect a characteristic of the TET smart patch. The one or more sensors may detect a status or state of the TET smart patch. In some embodiments, the state of the smart patch can comprise whether the smart patch has been unpackaged, applied, and/or remains in place.

In some embodiments, one or more sensors of a TET smart patch may activate in response to a package surrounding the TET smart patch or attached to the TET smart patch being manipulated or opened. In some embodiments, one or more sensors of the TET smart patch can be activated when a seal of a packaging surrounding the TET smart patch or attached to the TET smart patch is broken. In some embodiments, the TET smart patch can complete an electric circuit with a low-energy electrical current when in the packaging. In some embodiments, manipulating one or more parts of the packaging, like breaking a seal, peeling back a portion of the package, ripping or poking one or more parts of the package, or disconnecting a part of the package, for example, can activate the one or more sensors. The sensors can be, for example, light sensors, electricity sensors, pressure sensors, infrared sensors, sound sensors, ultrasound sensors, gas sensors, capacitive sensors, humidity sensors, touch sensors, temperature sensors, magnetic field sensors, resistive sensors, or any combination thereof.

In some embodiments, the smart patch may communicate data that is related to the state of the smart patch, to the cloud platform. In some embodiments, the data may be communicated to the cloud platform directly via a community network. In some embodiments, the data may be communicated using the BLE module. In some embodiments, the data may be communicated to the cloud platform indirectly through a paired smartphone application.

In some embodiments, the TET patch may comprise a processor. In some embodiments, the processor can perform analytics or calculations on data from one or more sensors of the TET patch. In some embodiments, the processor can perform statistical analysis on data from one or more sensors of the TET patch. In some cases, the statistical analysis can include finding averages of one or more data points from the one or more sensors of the TET patch. In some embodiments, the processor can aggregate data from the one or more sensors. In some embodiments, the processor can compare one or more individual pieces of data from the one or more sensors to an average or other statistical value of an aggregation of data from the one or more sensors.

In some embodiments, the processor of the TET patch may not contain any personally identifying health information. In some embodiments, the TET patch may not be labeled or otherwise contain any identifying information of the patient. In some embodiments, the TET patch can de-identify data from the one or more sensors.

In some embodiments, the cloud platform may link the smart patch data with prescription information for each patient, providing a complete view of the patient's adherence pattern in real time. In some embodiments, prescription information may include medication identifying information, medication dosage, medication timing, or medication interactions, or any combination thereof.

In some embodiments, additional prescription information may be gathered through connections to provider systems. In some embodiments, additional prescription information may be gathered through connections to pharmacy systems. In some embodiments, additional prescription information may be gathered through connections to provider and pharmacy systems, e.g., using standard industry protocols. In some embodiments, the smart patch data, the prescription information, or the additional prescription information, or any combination thereof can be integrated into the cloud platform, ensuring that full medication regimens are up-to-date and personalized for each patient.

In some embodiments, the smart patch data, the prescription information, and the additional prescription information may undergo data processing. In some embodiments, the smart patch data, the prescription information, and the additional prescription information may undergo cleansing, standardization, or encryption, or any combination thereof. In some embodiments, the smart patch data, the prescription information, and the additional prescription information may undergo data processing in the cloud platform. In some embodiments, the smart patch data, the prescription information, and the additional prescription information may be managed to facilitate data processing, storage, or analytics, or any combination thereof.

In some embodiments, the user applications may comprise smartphone applications and/or Amazon Echo applications. In some embodiments, the user applications may provide information concerning the smart patch data, or the prescription information to one or more persons other than the patient. In some embodiments, the user applications may provide patients and their care circles (e.g., family members, caregivers, pharmacy, physician, etc.) with access to smart patch status/state and replacement schedules. In some embodiments, the user applications may offer interactive features such as medication reminders, communication tools, or real-time updates on adherence across the patient's entire medication regimen, or any combination thereof.

In some embodiments, the TET platform may utilize an analytics engine (FIG. 15) to aggregate collected data. In some embodiments, the analytics engine of the TET platform may analyze prescription and/or medication schedule data. In some embodiments, the analytics engine of the TET platform may generate insights into patient behavior at a personal and/or community level. In some embodiments, the insights may allow real-time intervention for each individual level before a missed dose becomes problematic.

In some embodiments, the TET platform can send notifications to the patients or persons other than the patient. In some embodiments, the TET platform can send reporting notifications to the patient or persons other than the patient. In some embodiments, the TET platform may comprise reporting tools that can provide patients, caregivers, and healthcare providers with information. The information can include detailed adherence reports, facilitating continuous care improvements and accurate measures for cost-of-care models.

In some embodiments, notifications can comprise push notifications, text messages, calls, emails, banners, in-app alerts, voice alerts, audio tones, spoken alerts, or other sounds, visual signals, light signals, vibration signals such as vibration of one or more technological devices, electrical current signals across the skin or a device, or physical manipulation of one or more objects.

In some embodiments, notifications can be provided for misuse of the smart patch, misuse of one or more medications, one or more missed medication schedules, application of too many smart patches, application of too few smart patches, application of one or more incorrectly medicated smart patches, application of one or more expired medication smart patches, application of one or more defective smart patches, application of one or more smart patches to an incorrect area of the body, application of one or more smart patches for a time period that is too short, application or one or more smart patches for a time period that is too long, accidental detachment of one or more smart patches from the skin, intentional detachment of one or more smart patches from the skin, incomplete application of one or more smart patches, damage to one or more smart patches, application of one or more smart patches with incorrect dosage of medication, application of one or more smart patches with incomplete or incorrect accompanying validation or security information, or another type of notification.

In some embodiments, notifications can be provided to authorized users. Authorized users can include relatives of the patient, friends of the patient, or care providers of the patient. Care providers of the patient can include medical personnel such as the patient's physician team, at-home care team, nursing team, nursing home staff, or other healthcare worker(s).

In some embodiments of the TET platform, all operations can be compliant with HIPAA and other relevant regulations. Patient data can be encrypted throughout its lifecycle, with decryption keys managed securely to maintain confidentiality.

In some embodiments, the TET platform can aggregate data of one or more patients from each patient's TET system. In some cases, the TET platform can aggregate and de-identify data. In some cases, the TET platform can aggregate previously de-identified data. In some embodiments, the TET platform can process aggregated data to determine one or more population-level trends or data points. In some embodiments, the one or more population-level trends or data points can concern population-level data in areas such as, for example, medication lateness, missed doses, or smart patch removal rates in various populations. In some embodiments, the one or more population-level trends or data points can concern population-level data in areas such as, for example, epidemiological data derived from medication or other patient data collected by the TET platform.

In some embodiments, the TET platform can be integrated with one or more biometric applications or biometric devices. In some embodiments, TET platform data can be analyzed together with data from one or more biometric applications or biometric devices. In some embodiments, aggregated data gathered by the TET platform can be integrated with aggregated data from one or more biometric applications or biometric devices.

In some embodiments, the device layer of the TET platform does not store or contain any personally identifiable information. In some embodiments, the device layer of the TET platform does not output any personally identifiable information. In some embodiments, the device layer of the TET platform does not process any personally identifiable information. In some embodiments, the cloud platform does not receive any personally identifiable information from the device layer. In some embodiments, the sidewalk network does not receive any personally identifiable information from the TET patch of the device layer. In some embodiments, the IoT Core of the cloud platform does not receive or process any personally identifiable information from the device layer.

In some embodiments, the TET platform architecture may be scalable, ensuring it can adapt to evolving healthcare needs and technological advancements. In some embodiments, data access and integration may be metadata driven.

Figure 15:
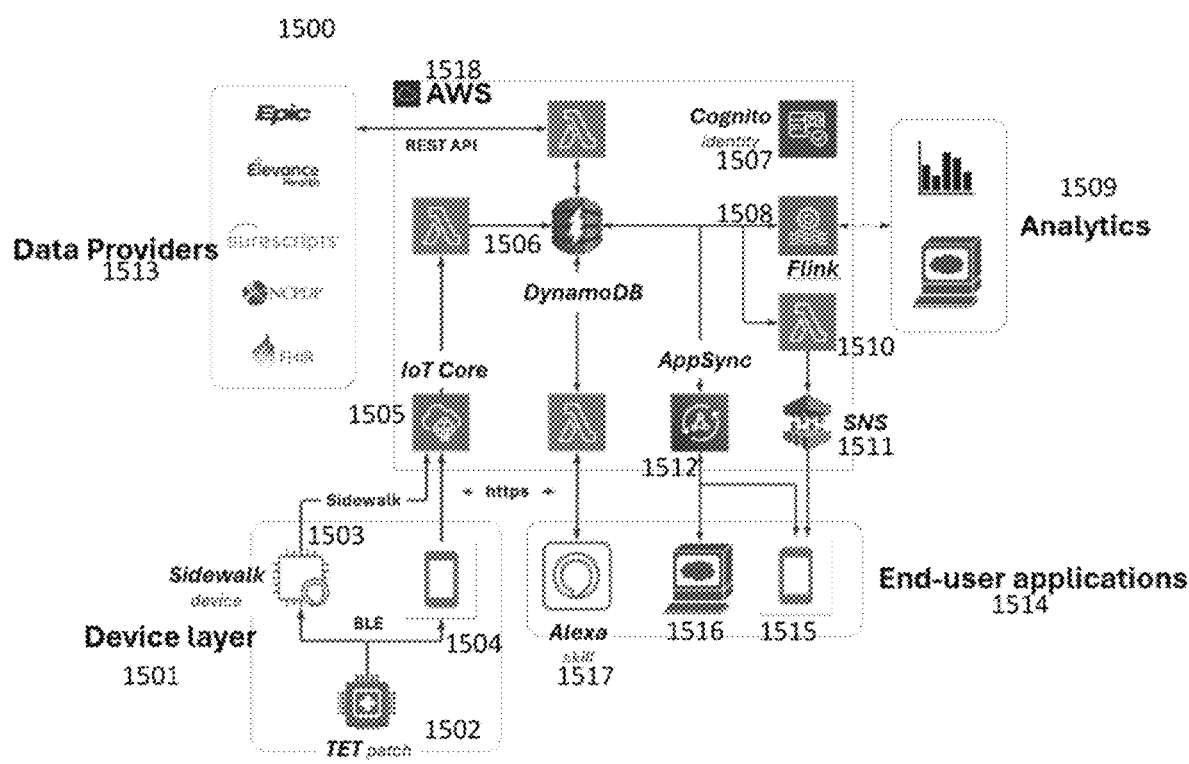
FIG. 15 illustrates a non-limiting diagram of an exemplary internet connectivity system between a device layer, end user applications, and cloud-based connectivity systems.

As shown in FIG. 15, the TET platform may comprise multiple technologies or modules to facilitate smart patch monitoring (1500). The TET platform may comprise a device layer/module (1501). In some embodiments, the device layer may comprise the transdermal smart patch (TET smart patch) (1502) having an embedded System-on-a-Chip (SoC). In some embodiments, the SoC can be integrated with one or more sensors to monitor the smart patch status. In some embodiments, the TET smart patch may further comprise a battery. In some embodiments, the battery can be an integrated thin-film flexible printable battery. In some embodiments, the battery may supply power to the SoC.

In some embodiments, the battery may enter a low-power mode. In some embodiments, the battery may enter a low-power mode as a result of communication from the communication subsystem of the TET smart patch. In some embodiments, the battery may enter a low-power mode as a result of a communication from a cloud module. In some embodiments, the battery may enter a low-power mode in response to a signal from one or more sensors. In some embodiments, the battery can enter a low-power mode to preserve battery and extend battery life. In some embodiments, the battery can enter a low-power mode as a result of a signal for a change of the TET smart patch from work mode to sleep or hibernation mode. In some embodiments, the battery may exit a low-power mode. In some embodiments, the battery may exit a low-power mode as a result of communication from the communication subsystem of the TET smart patch. In some embodiments, the battery may exit a low-power mode as a result of a communication from a cloud module. In some embodiments, the battery may exit a low-power mode in response to a signal from one or more sensors. In some embodiments, the battery can exit a low-power mode to preserve battery and extend battery life. In some embodiments, the battery can exit a low-power mode as a result of a signal for a change of the TET smart patch from sleep or hibernation mode to work mode.

In some embodiments, the SoC may comprise a microprocessor. In some embodiments, the microprocessor may have programming responsible for sensor data collection, storage, or communication, or any combination thereof. In some embodiments, the chip can be made from a device from Silicon Laboratories (SiLabs) or Nordic Semiconductor (Nordic). In some embodiments, the TET smart patch may communicate to a network. In some embodiments, communication to and from the smart patch may take place using the Bluetooth Low Energy (BLE) radio protocol. In some embodiments, the TET smart patch may communicate using NFC, WiFi, cellular data, 4G cellular data, 5G cellular data, radio such as wireless LAN, near-field communication, satellite communication, IEEE, RFID, or a combination thereof.

In some embodiments, the TET chip may further comprise a connection mechanism to a community network (FIG. 15). In some embodiments, the community network may allow signaling between one or more devices in an area, e.g., Amazon Sidewalk community network (Sidewalk) (1503). In some embodiments, the TET chip may use a cascading set of connection options that use the patient's or other nearby mobile phone. In some embodiments, messages from each communication path may be securely moved into different queues in the cloud environment (1518). In some embodiments, the data may aggregate. In some embodiments, the aggregated data can be separated from downstream environments. In some embodiments, additional communication channels can be added.

In some embodiments, the TET platform may further comprise a cloud module (1518). The cloud module (1518) may further comprise one or more AWS cloud services. In some embodiments, the AWS cloud services may comprise managed services. In some embodiments, managed services may comprise, for example, AWS IoT Core (1505), Lambda (1510), DynamoDB (1506), Flink (1508), or other AWS cloud services. In some embodiments, the AWS cloud module (1518) may perform data processing and storage. In some cases, the data processing and storage may be performed in a HIPAA-compliant manner. In some embodiments, the cloud services may be portable. In some embodiments, data may be input to the AWS IoT Core (1505). In some embodiments, raw data may be moved and/or stored in the cloud module (1518). In some embodiments, AWS Lambda (1510) functions may move raw data to a DynamoDB object store (1506). In some cases, this movement of raw data may trigger one or more additional status updates to downstream systems. In some cases, the one or more additional status updates may be output from the cloud module (1518) and input to data providers, an end-user application, or an analytics module (FIG. 15). In some cases, the one or more additional status outputs may be received as inputs by one or more downstream applications within the cloud module. In some embodiments, the one or more downstream applications within the cloud module may comprise AWS AppSync (1512) or AWS Simple Notification Service (SNS) (1511), or both. In some embodiments, AWS AppSync (1512) may facilitate data updates in real time to user applications with open sessions. In some embodiments, the data updates may facilitate interaction by the user with a GUI. In some embodiments, AWS SNS (1511) may receive and process alert and notification messages in response to various planned and detected events. In some embodiments, the user may interact with the alert and notification messages on a GUI. In some cases, the planned and detected events can comprise a medication schedule management event, a medication regimen completion event, a medication change event, or a communication event, or any combination thereof. In some embodiments, the AWS cloud services module (1518) may further comprise AWS Cognito (1507). In some embodiments, AWS Cognito (1507) may manage user account details. In some cases, AWS Cognito (1507) may process user login and authentication. In some cases, AWS Cognito (1507) may store security information. In some cases, AWS Cognito (1507) may process user login and authentication and may store security information. In some embodiments, the application code may be updated to cause the AWS cloud module (1518) to perform functions comprising enforcing updated data security measures.

In some embodiments, notifications can comprise push notifications, text messages, calls, emails, banners, in-app alerts, voice alerts, audio tones, spoken alerts, or other sounds, visual signals, light signals, vibration signals such as vibration of one or more technological devices, electrical current signals across the skin or a device, or physical manipulation of one or more objects.

In some embodiments, notifications can be provided for misuse of the smart patch, misuse of one or more medications, one or more missed medication schedules, application of too many smart patches, application of too few smart patches, application of one or more incorrectly medicated smart patches, application of one or more expired medication smart patches, application of one or more defective smart patches, application of one or more smart patches to an incorrect area of the body, application of one or more smart patches for a time period that is too short, application or one or more smart patches for a time period that is too long, accidental detachment of one or more smart patches from the skin, intentional detachment of one or more smart patches from the skin, incomplete application of one or more smart patches, damage to one or more smart patches, application of one or more smart patches with incorrect dosage of medication, application of one or more smart patches with incomplete or incorrect accompanying validation or security information, or another type of notification.

In some embodiments, notifications can be provided to authorized users. Authorized users can include relatives of the patient, friends of the patient, or care providers of the patient. Care providers of the patient can include medical personnel such as the patient's physician team, at-home care team, nursing team, nursing home staff, or other healthcare worker(s).

In some embodiments, the cloud module (1518) may output data to one or more end-user applications (1514). The cloud module may output the data to one or more end-user applications using one or more data exchange applications, for example AppSync (1512). The one or more data exchange applications receive input comprising data from the cloud module (1518), and process the data for output to one or more end-user applications (1514). The one or more end-user applications (1514) can comprise, for example, one or more software applications. In some embodiments, the one or more data exchange applications receive input comprising relevant user data. In some embodiments, the relevant user data is processed by the data exchange applications into a data form suitable for output through authenticated connections. In some embodiments, the one or more data exchange applications may be configured to automatically output updates and/or notifications to the one or more end-user applications (1514) as changes are made on the server. In some cases, these output updates and/or notifications may comprise receive real-time status updates within the one or more end-user applications (1514). In some embodiments, the output updates and/or notifications to the one or more end-user applications (1514) can comprise, for example, whether a TET smart patch is online or offline, whether a medication schedule has not been completed, whether one or more medications have not been indicated as taken, whether one or more medications have been indicated as taken late, or whether a medication routine has been completed, or any combination thereof. In some embodiments, the user can interact with a notification and/or output update using a GUI.

In some embodiments, notifications can comprise push notifications, text messages, calls, emails, banners, in-app alerts, voice alerts, audio tones, spoken alerts, or other sounds, visual signals, light signals, vibration signals such as vibration of one or more technological devices, electrical current signals across the skin or a device, or physical manipulation of one or more objects.

In some embodiments, notifications can be provided for misuse of the smart patch, misuse of one or more medications, one or more missed medication schedules, application of too many smart patches, application of too few smart patches, application of one or more incorrectly medicated smart patches, application of one or more expired medication smart patches, application of one or more defective smart patches, application of one or more smart patches to an incorrect area of the body, application of one or more smart patches for a time period that is too short, application or one or more smart patches for a time period that is too long, accidental detachment of one or more smart patches from the skin, intentional detachment of one or more smart patches from the skin, incomplete application of one or more smart patches, damage to one or more smart patches, application of one or more smart patches with incorrect dosage of medication, application of one or more smart patches with incomplete or incorrect accompanying validation or security information, or another type of notification.

In some embodiments, notifications can be provided to authorized users. Authorized users can include relatives of the patient, friends of the patient, or care providers of the patient. Care providers of the patient can include medical personnel such as the patient's physician team, at-home care team, nursing team, nursing home staff, or other healthcare worker(s).

In some embodiments, the one or more data exchange applications may further comprise a query construction and object retrieval module. For example, AppSync (1512) uses a GraphQL-based service that manages query construction and object retrieval. In some embodiments, the query construction and object retrieval module may authenticate access and package data for transport to the one or more end user applications. In some embodiments, the query construction and object retrieval module can allow uniform access to a central database by internal cloud users and external application users.

In some embodiments, one or more data exchange applications, for example, AppSync (1512), may deliver data to client applications as it exists in a central database. In some cases, the data can be delivered without applying additional data processing. In some cases, the data delivery can comprise delivering encrypted data values without decryption. In some cases, one or more data exchange applications may perform decryption using an end-user application (1514) or a cloud-based Lambda function (1510). In some embodiments, the user can interact with the data being delivered using a GUI displaying the data being delivered.

In some embodiments, a cloud module may further comprise a serverless computing service, for example AWS Lambda (1510). In some cases, the serverless computer service may be used for running backend processes without requiring provisioning or managing servers. In some embodiments, the serverless computing service may process incoming IoT data, handle event detection, manage notification delivery, or trigger data ingestion routines across the environment, or any combination thereof. In some cases, serverless computing service algorithms, such as Lambda (1510), may be written in Python or TypeScript. and In some cases, serverless computing service algorithms, such as Lambda (1510), can be executed by various functional ids. In some cases, the ids can mimic internal operational users. In some cases, the ids can have roles and privileges granting access to only those resources necessary for specific executions. For example, an id running a Lambda function that moves messages from the IoT Core (1505) to Dynamo DB (1506) may not have the same privileges as an id that sends a notification or alert.

In some embodiments, the cloud module may further comprise an identity module, for example AWS Cognito (1507). In some embodiments, the identity module can process user login and authentication data. In some embodiments, the identity module can create accounts, reset passwords, or manage two factor authentication, or any combination thereof. In some embodiments, the identity module can further process biometric sign-ins. In some cases, the biometric sign-ins can comprise, for example, fingerprint sign-ins, voice recognition sign-ins, facial recognition sign-ins like FaceID, or any combination thereof. In some embodiments, the identity module can integrate with third-party identity providers like Google, Amazon, and Apple. In some cases, the identity module can store additional information outside of the application-level data model. In some cases, this storage can allow separation between application logic and authentication management. In some embodiments, the identity module can store security-related keys and/or device-provided tokens to authorize certain operations. In some cases, the operations can be notifications or alerts. In some cases, the operations can be displayed on a GUI.

In some embodiments, the cloud module may further comprise a notification module, for example an AWS Simple Notification Service (SNS) (1511). In some embodiments, the notification module can manage the delivery of push notifications to users on different kinds of devices. In some embodiments, the push notifications can be alerts, text messages, images, sounds, vibrations, or any combination thereof. In some cases, the push notifications may be triggered by a serverless computer service, such as one or more Lambda functions (1510). In some cases, the notification module can track device status and/or generate reminder queues.

In some embodiments, the cloud module may further comprise an analytics module (1509), for example Amazon Flink (1508), Apache Flink, or AWS Kinesis Data Analytics. In some embodiments, the analytics module can perform enterprise-scale stream processing of real time and/or batch data. In some embodiments, the analytics module (1509) may be used for bulk data processes. In some cases, the bulk data processes can operate on entire datasets. In some cases, the datasets can be third-party reference data. In some embodiments, the analytics module (1509) can operate on datasets from metadata. In some cases, the metadata can be from various import sources, targets, formats, or mapping rules, or any combination thereof. In some embodiments, the analytics module (1509) can generate bulk data extracts and/or stage database areas for downstream reporting products. In some embodiments, the analytics module (1509) can operate on one or more integration points.

In some embodiments, the TET platform may further comprise end-user applications (1514). In some embodiments, end-user applications (1514) may allow users to interact with the TET platform through software or devices, for example mobile applications (1515) or Alexa Echo (1517) devices. In some embodiments, the software and devices (1516) produce interactions and reminders related to smart patch status and/or medication routines. In some embodiments, a mobile device may provide a number of additional services unavailable through Alexa Echo (1517).

In some embodiments, the end-user applications (1514) may comprise mobile or stationary device applications. In some cases, the applications can display patient data. In some cases, patient data can comprise smart patch status, receiving reminders about medication schedules, or facilitating communication within a patients circle of care, or any combination thereof. In some embodiments, mobile applications may be built in the Ionic development framework using Typescript. In some embodiments, the mobile applications may comprise a primary user interface layer and a secondary layer. In some embodiments, the secondary layer may provide additional services, e.g., location and BLE communication. In some embodiments, the end-user applications may comprise an Amazon Echo ecosystem. In some embodiments, the end-user applications may provide voice-ready access to smart patch and medication information, reminders, notifications, or critical alerts, or any combination thereof. In some embodiments, the end-user applications may require cloud connectivity. In some embodiments, when the end-user applications are offline, the end-user applications may provide limited information (e.g., the last known smart patch status). In some embodiments, application data may be updated in real-time. In some embodiments, the patient and a non-patient person can see the updates. In some embodiments, all users in the same care circle can see status changes simultaneously. In some embodiments, reminders and alerts may be directly generated by the application running on a user's mobile device, e.g., a phone. In some embodiments, reminders and alerts may not be directly generated by the application running on a user's mobile device, e.g., a phone. In some embodiments, reminders and alerts may be sourced from the cloud.

In some embodiments, the TET platform may further comprise one or more data providers (1513). In some embodiments, connections to external systems may gather up-to-date information about patient information. In some cases, patient information can comprise patient data, such as a patient's prescription details, patient prescription scheduling, patient contacts, a smart patch's status, or a smart patch's packaging details, or any combination thereof. In some embodiments, the platform may use standard data interchange mechanisms.

In some embodiments, the platform can use a modular system to support a variety of transport (e.g., REST) and data (e.g., FHIR) protocols. In some embodiments, data may be imported into and transported through a series of "layers" of the data providers to manage collection, data quality and standardization, and curation for downstream systems.

TET Smart Patch and IoT Connectivity

Figure 16:
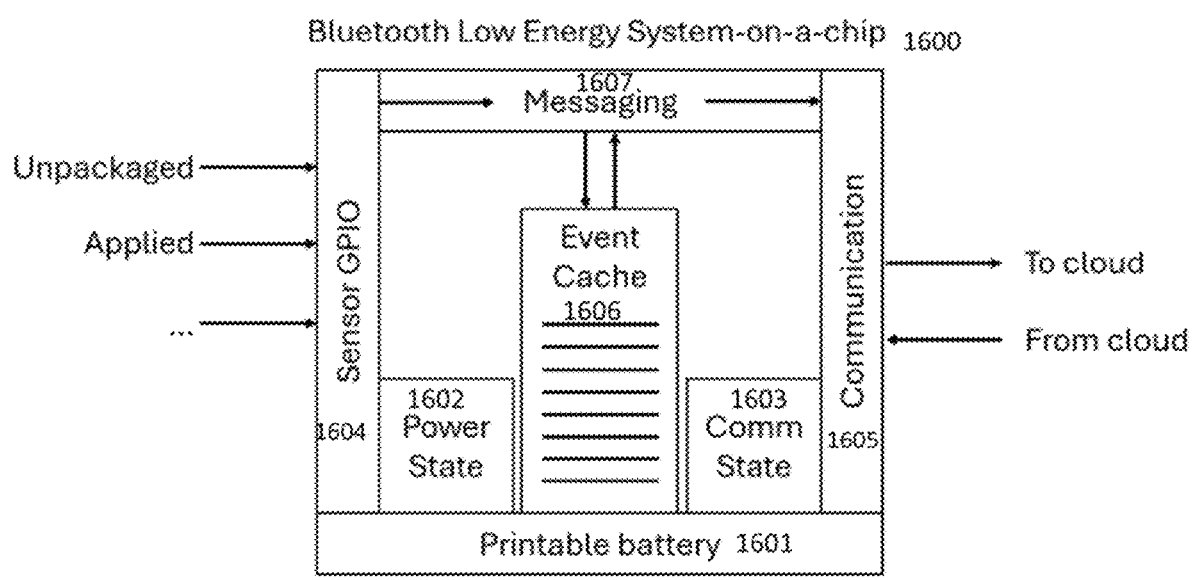
FIG. 16 illustrates a non-limiting diagram of an exemplary technology stack of a low energy system-on-a-chip with Bluetooth connectivity capability.

FIG. 16 shows a high-level view of the TET smart patch system-on-a-chip (SoC) (1600). In some embodiments, the SoC (1600) may integrate with a signaling ecosystem, for example an NFC system such as a Bluetooth ecosystem, for example a low-power Bluetooth systems, WiFi ecosystem, cellular ecosystem, 4G cellular system, 5G cellular system, LAN ecosystem, or any combination thereof. In some embodiments, the signaling ecosystem can be supported by one or more software elements in a cloud and in an end-user application. In some embodiments, the Bluetooth ecosystem may be supported by both Amazon Sidewalk and a Phone application.

In some embodiments, the software developed to run on the chip may be configured to interface with external sensors, manage device state, and communicate state messages with a master controller. In some cases, the master controller can be a local controller. In some cases, the master controller can be a local Bluetooth master controller. In some cases, the controller can be, for example, a Sidewalk Gateway or smartphone with Bluetooth enabled.

In some embodiments, SoC actions may be managed by an application running in the application framework of the device. In some embodiments, SoC may provide an operating system to manage data retrieval, compute tasks, onboard queues, scheduling, object generation, or SQL generation, or any combination thereof.

In some embodiments, the SoC may be configured with the TET Smart patch application code. In some embodiments, the SoC may be configured with a collection of information unique to each individual chip. In some cases, the unique information may include a BLE Device Address, e.g., a unique 48-bit id, or a set of identifying keys, or both.

In some cases, the set of identifying keys may be used during the provisioning and communication process.

In some embodiments, the SoC may comprise a power state (1602). In some embodiments, after initial configuration, the SoC (1600) may be put into a very low power state, or hibernation power state (1602), to preserve power until it is ready to be used. In some embodiments, the device may be essentially turned off during this time. In some embodiments, information stored at this time may be in a form of non-volatile RAM (NVRAM).

In some embodiments, the SoC may remain in its hibernation power state (1602) until the patient is ready to apply the transdermal smart patch. In some embodiments, when the smart patch is removed from its packaging, a sensor on the smart patch may detect the removal. In some cases, detection of removal can trigger the power state (1602) to transition from a hibernation power state to a communication power state. In some cases, this transition can be waking the smart patch from a hibernation power state. In some embodiments, the SoC may enter a communication power state (1603) using the communication subsystem (1605). In some embodiments, in a communication power state (1603), the SoC may begin to actively seek a connection to the cloud. In some embodiments, the SoC may comprise one or more sensors. In some cases, the one or more sensors can be configured to determine whether the smart patch is out of the packaging, applied, or removed from application.

In some embodiments, the SoC can further receive information from one or more sensors (FIG. 16). In some embodiments, the SoC has one or more subsystems to process data from the one or more sensors (1604). In some embodiments, a Sensor GPIO subsystem (1604) can read data from the sensors to determine when to activate the device. In some embodiments, after activation by the GPIO subsystem (1604), a second subsystem can configure the SoC to alternate between sensor monitoring, transmit/receive cycles, and a low power sleep state.

In some embodiments, the sleep power state (1602) can provide power to volatile RAM to hold dynamic information for transmission to the cloud. In some cases, the overall power demands of the system can be a function of message transmission interval, transmission power, or CPU processing speeds, or any combination thereof.

In some embodiments, sensor information may be retrieved by code that reads a series of ports (1604). In some cases, the ports can be General Purpose Input/Output (GPIO) ports. In some embodiments, one or more sensors can be connected to one or more ports. In some embodiments, the system may comprise at least two, at least three, at least four, or more than four ports.

In some embodiments, the SoC may comprise a messaging subsystem (1607). In some embodiments, the messaging subsystem (1607) may perform assembly of message payloads. In some embodiments, the messaging subsystem (1607) may perform persistence functions for messages locally. In some cases, the persistence functions remain until delivery to the cloud has been confirmed by the communication subsystem (1607).

In some embodiments, a message may comprise the following details: device identifier, device uptime, device battery level, sensor status (e.g., attached, applied, etc.), or device uptime at time of last status change, or any combination thereof.

In some embodiments, when a connection is active, an attempt may be made to deliver the message using the communication subsystem. In some cases, if delivery succeeds, the message may be discarded. In some cases, if there is no active connection, or the transmission fails for any reason, or both, the message may be stored in a recovery event queue (FIG. 16) to be replayed during some later attempt.

In some embodiments, the SoC may further comprise an event cache (1606). In some embodiments, the event cache (1606) may further comprise a recovery event queue. In some cases, the recovery event queue can store messages that record each status change. In some embodiments, as a message is added to the recovery queue, the status can be checked by the SoC. In some cases, if the sensor status has not changed, then the earlier message can be replaced with the newer message by the communication subsystem (1605). In other cases, if the status has changed, the new message can be appended to the recovery event queue.

In some embodiments, the SoC may further comprise a Sidewalk network to provide a connection-oriented protocol directly to the AWS IoT platform. In some cases, the Sidewalk network of the SoC may enable a device to connect to the cloud without interacting with a user's phone. In some cases, this connection can bypass the activation and configuration processes.

In some embodiments, the Sidewalk connection may be activated at device startup. In some cases, the Sidewalk connection may be activated if a suitable gateway is within range. In some embodiments, the connection may remain active as long as any gateway is available.

In some embodiments, the TET smart patch may use a local connection, for example a Sidewalk connection. In some embodiments, the TET smart patch may periodically check for a local connection, such as a Sidewalk connection. In some embodiments, if another communication mode has been activated because Sidewalk was out of range for some time, the TET smart patch may periodically check for a Sidewalk connection automatically.

In some embodiments, if a Sidewalk connection is unavailable, the smart patch may begin advertising its presence via signaling. In some cases, the signaling can occur over NFC, WiFi, Bluetooth, cellular data, 4G cellular data, 5G cellular data, LAN, or another signaling method. In some cases, the signaling can occur over BLE for a phone-based connection. In some embodiments, if a suitable phone application is found, the smart patch and phone may use security keys on the phone and on the device to jointly. In some cases, this joint security key use may authenticate that the device and phone application belong to the same user. In some cases, the connection may fail if the devices cannot mutually identify each other.

In some embodiment, if a phone connection cannot be established, the TET smart patch may fall back to advertising an encrypted payload. In some embodiments, the encrypted payload can be recognizable by the phone application running on any phone in the area. In some cases, one or more phones can smart patch messages to the cloud while being unable to read their payload.

In some embodiments, in the advertising signaling mode, the SoC may confirm that the message is received by the cloud when a connection is reestablished. In some embodiments, once a connection has been reestablished, the events in the recovery event queue may be replayed to the cloud. In some cases, the events in the recovery event queue of the SoC may be identified and processed as if they were original messages and communication resumes.

In some embodiments, the SoC may comprise a beacon mode. In some cases, beacon mode can comprise phone applications forwarding information across signaling connections, such as BLE signaling. In some cases, phone applications can form new connections even when they are running in the background, e.g., when they are not the main application on the screen.

In some embodiments, the application may start manually when a user receives a notification. In some embodiments, the application may start manually when the user opens the device intentionally. In some embodiments, if a phone gets restarted, the application may not be running in the background. In some cases, if a phone gets restarted, the application may start running in the background only when the user receives a notification or opens the device intentionally. In some embodiments, the TET smart patch can remain in an unconnected state after an automatic update or other restart.

In some embodiments, the smart patch can act as an iBeacon. In some embodiments, an iBeacon can be registered with a phone. In some embodiments, when an iBeacon is registered with a phone, the phone may wake a specific application when the phone comes within range.

In some embodiments, if a TET smart patch determines that it has not had a connection for some time, it may periodically revert to this iBeacon mode. In some embodiments, if the phone detects the iBeacon, it may start the application. In some embodiments, if the phone detects the iBeacon, a normal connection can be established. In some embodiments, the SoC can ensure connection security with the communication subsystem (FIG. 16). In some embodiments, each message can be transmitted securely from the device to the cloud. In some embodiments, the SoC can ensure that smart patch status data is accurate through the communication and sensor subsystems. In some embodiments, the SOC can prevent incorrect or garbled data injected into the system through the sensor GPIO and communication subsystems.

In some embodiments, the local connection module, for example Amazon Sidewalk, encrypts and validates all connections. In some embodiments, the protocol can be essentially set up like an SSL-based private network tunnel implemented over a BLE network. In some embodiments, message encryption and decryption may be handled entirely by the protocol stack, with all content arriving at a pre-configured endpoint.

Figure 17:
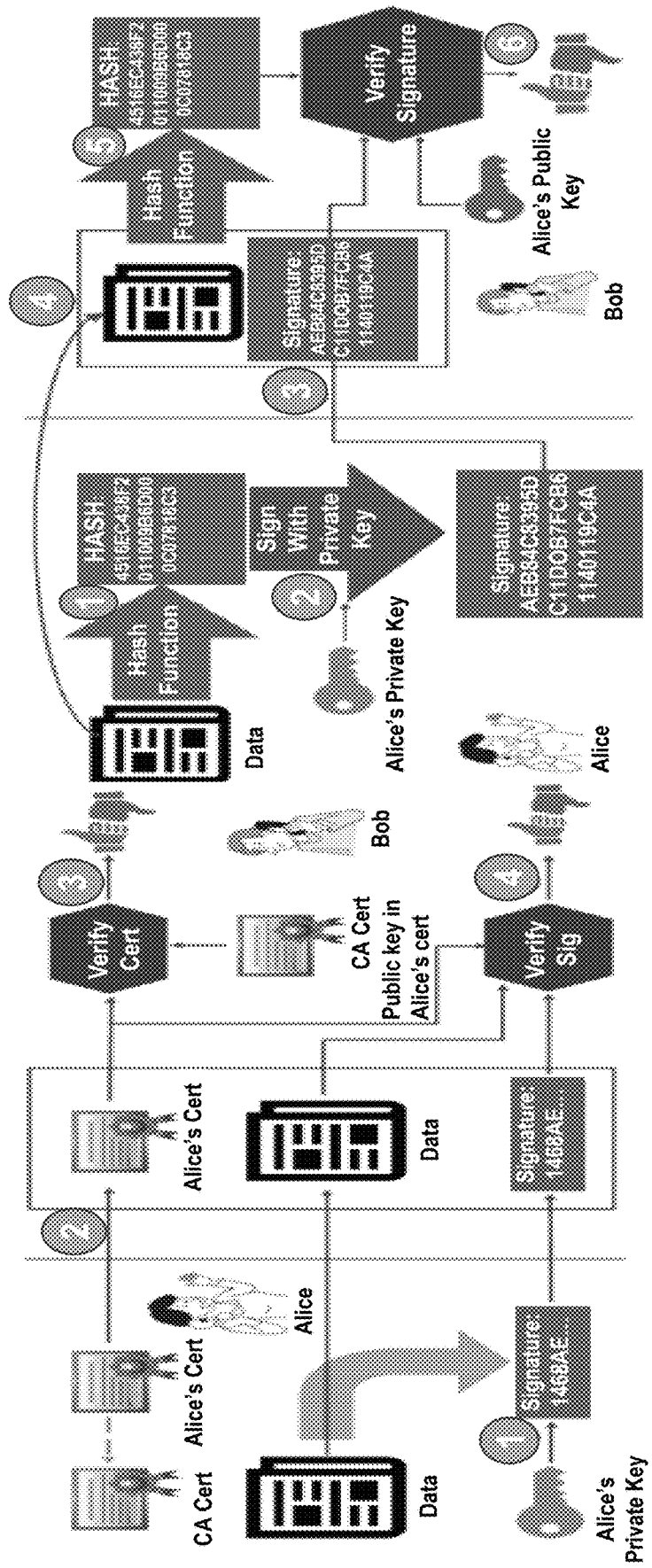
FIG. 17 illustrates a non-limiting diagram of an exemplary internet connectivity and authentication system between one or more devices of one or more users and encryption-based data authentication schemes.

In some embodiments, mobile phone connection security may be handled in the application layers on the SoC and on the phone (FIG. 17). In some cases, the system can comprise application-level security (FIG. 17).

In some embodiments, a standard BLE connection can be established. In some embodiments, each end of the application can authenticate the other based on the use of pre-signed trusted certificates as depicted in FIG. 17. In some embodiments, the device certificate may be installed during manufacturing. In some embodiments, the phone application can be delivered to the phone after a successful login. In some embodiments, once the two endpoints have been authenticated, the devices can agree to a shared key that is used to encrypt all messages for the current session (FIG. 17). In some embodiments, if either device fails to recognize the identity of the other, the session can be terminated.

In some embodiments, when advertising, messages can be encrypted and signed using the pre-installed device certificates. In some cases, encrypted messages can later be decrypted in the cloud. In some embodiments, mobile phones that forward these messages can be rendered unable to read their content. In some embodiments, encrypted advertising messages may be exclusively forwarded to the cloud by devices that support ADV_EXT_IND and related protocol data units.

In some embodiments, a user's private key can be processed into a custom signature using user data (FIG. 17). In some embodiments, the user data can be used to generate one or more authentication certifications. In some embodiments, a signature and certification can be combined to verify certification or verify signature. In some embodiments, the verifications can each result in a binary approval or disapproval of the authentication. In some embodiments, an approval can result in transfer of data from a patient to another user. In some embodiments, a disapproval can result in prevention of data transfer between users. In some cases, one or more hash functions can be used to convert user data into encrypted data. In some cases, the one or more hash functions can be combined with a user's private key for authentication processing. In some embodiments, a public key can be used to decrypt encrypted signatures, resulting in data transfer.

In some embodiments, the implementation of the cloud platform can be modularized. In some embodiments, changes can be made to core components without requiring major rewrites across the environment.

In some cases, one or more messages from one or more TET smart patches may first land in an MQTT endpoint. In some cases, the MQTT endpoint can be configured and managed through the AWS IoT Core service. In some cases, each message source may be individually authenticated. In some cases, the authentication can take place using pre-installed device keys or through the phone user's account, or both.

In some embodiments, each path may target a separate queue. In some cases, each path may result in path variations being handled in isolation. In some embodiments, existing message paths can be scaled independently. In some embodiments, new message paths can be added. In some embodiments, each path can be updated without affecting other paths.

In some embodiments, messages landing in any queue may be forwarded to a central database, such as DynamoDB, by serverless computing service algorithms, such as an AWS Lambda function. In some cases, advertising messages may be decrypted during this process. In some embodiments, each message entering a central database, such as DynamoDB, can be handled similarly regardless of its source.

In some embodiments, data storage for both messages and application data may be provided by a central database, for example DynamoDB. In some embodiments, the central database can be a NoSQL object store. In some embodiments, the central database can comprise scalable storage and access speed.

In some embodiments, each message uploaded to an IoT Core may be forwarded to a landing table in a central database, such as DynamoDB. In some embodiments, messages may be monitored in real time for status updates. In some cases, each status change can be recorded as a device_event. In some embodiments, if the status is unchanged, the "updatedAt" timestamp for the latest device_event can be updated. In some embodiments, the device_event table can only record changes, not raw events, which may be discarded after some time.

In some embodiments, each status change may also trigger an update in the device table. In some cases, the device table contains the latest status for the smart patch. In some cases, this table may be monitored to deliver immediate updates when a smart patch is attached or detached.

In some cases, records might arrive out-of-order if advertising messages were forwarded while the smart patch was offline. In some cases, a new device_event may be created to track the history of the device. In some cases, the latest status updates may trigger changes in the device table. In some cases, the advertising events may have already served to keep the device information updated.

Data Model

In some embodiments, the data model can comprise one or more subject areas. In some cases, the data model can comprise four subject areas: electronics, members, integrations, and operations.

Figure 18:
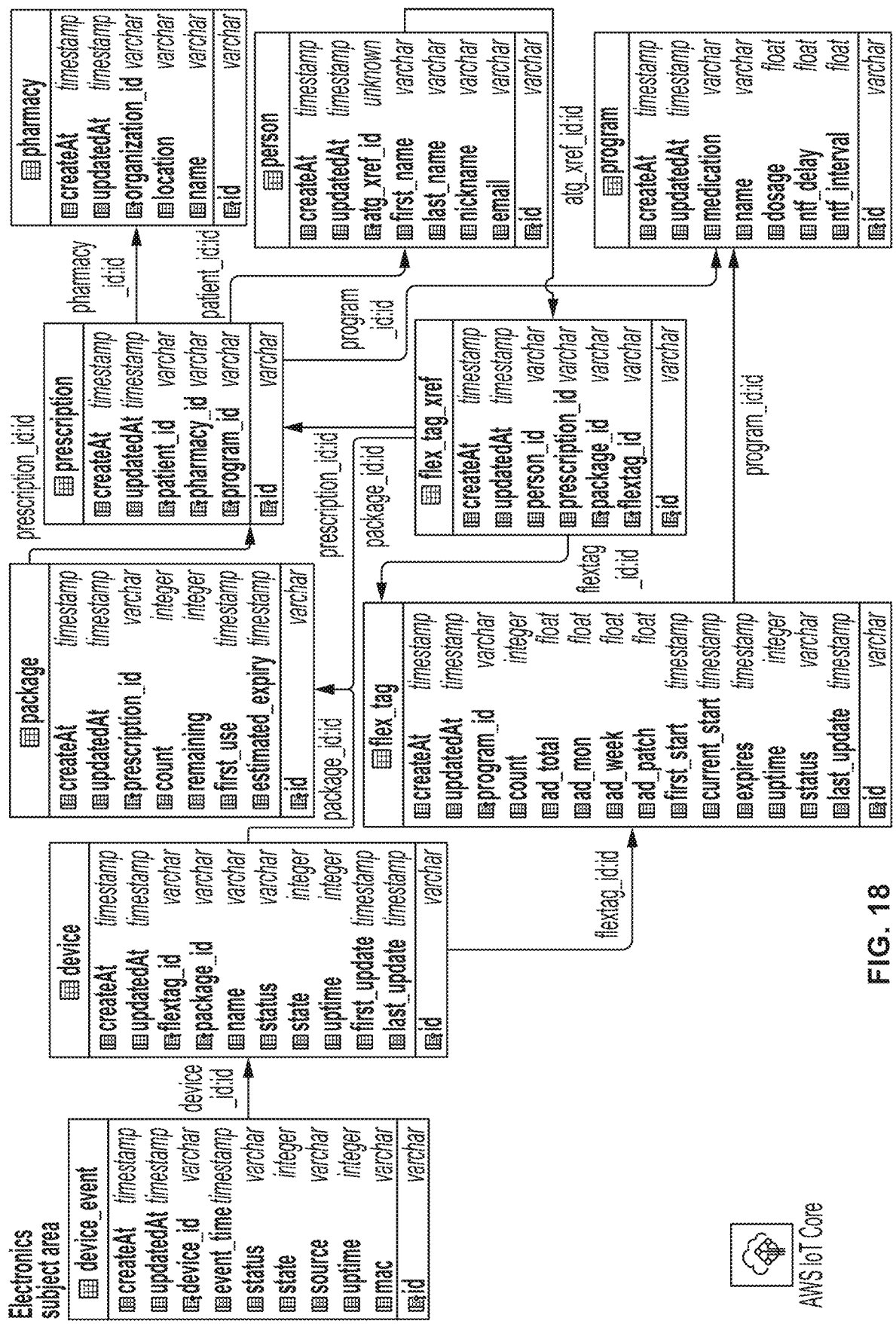
FIG. 18 illustrates a non-limiting diagram of an exemplary connectivity configuration for electronics databases.

In some embodiments, as shown in FIG. 18, the electronics subject area may comprise a plurality of modules that can track device details and messages. In some embodiments, each of the plurality of modules can comprise one or more databases, one or more algorithms, or one or more matrices, or any combinations thereof (FIG. 18).

In some embodiments, data rates may be on the order of 1 GB per patient per year. In some embodiments, raw messages may be stored for three days. In some embodiments, total data volumes may level off for each patient at closer to 10 MB per patient, or 1 TB for 100,000 active patients.

In some embodiments, the plurality of modules may comprise the current status details for each TET smart patch as accessed by user applications. In some embodiments, patch manufacturing information may allow links to each TET smart patch and patient, enabling notification and monitoring.

In some embodiments, notifications can comprise push notifications, text messages, calls, emails, banners, in-app alerts, voice alerts, audio tones, spoken alerts, or other sounds, visual signals, light signals, vibration signals such as vibration of one or more technological devices, electrical current signals across the skin or a device, or physical manipulation of one or more objects.

In some embodiments, notifications can be provided for misuse of the smart patch, misuse of one or more medications, one or more missed medication schedules, application of too many smart patches, application of too few smart patches, application of one or more incorrectly medicated smart patches, application of one or more expired medication smart patches, application of one or more defective smart patches, application of one or more smart patches to an incorrect area of the body, application of one or more smart patches for a time period that is too short, application or one or more smart patches for a time period that is too long, accidental detachment of one or more smart patches from the skin, intentional detachment of one or more smart patches from the skin, incomplete application of one or more smart patches, damage to one or more smart patches, application of one or more smart patches with incorrect dosage of medication, application of one or more smart patches with incomplete or incorrect accompanying validation or security information, or another type of notification.

In some embodiments, notifications can be provided to authorized users. Authorized users can include relatives of the patient, friends of the patient, or care providers of the patient. Care providers of the patient can include medical personnel such as the patient's physician team, at-home care team, nursing team, nursing home staff, or other healthcare worker(s).

Figure 19:
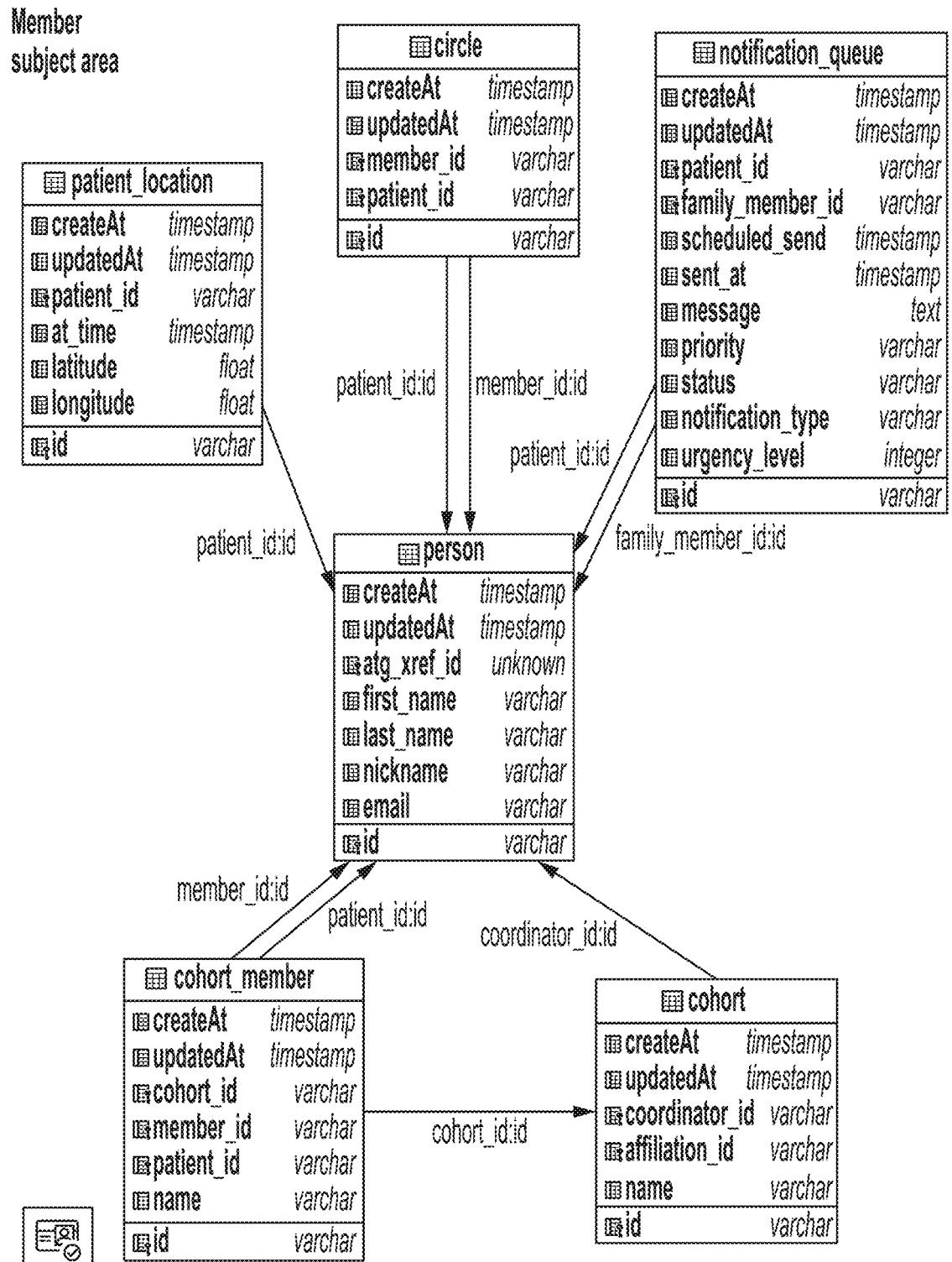
FIG. 19 illustrates a non-limiting diagram of an exemplary connectivity configuration for members databases.

As shown in FIG. 19, in some embodiments the members subject area may comprise a plurality of modules. In some embodiments, the plurality of modules may be linked with one or more authentication modules, for example the AWS Cognito service. In some embodiments, the data fields may be encrypted in place to protect personal health information. In some embodiments, the data fields may be encrypted and decrypted using customer-specific keys shared with the user application and internal cloud systems. In some embodiments, the members subject area may comprise a plurality of databases, algorithms, datasets, matrices, or any combination thereof.

Figure 20:
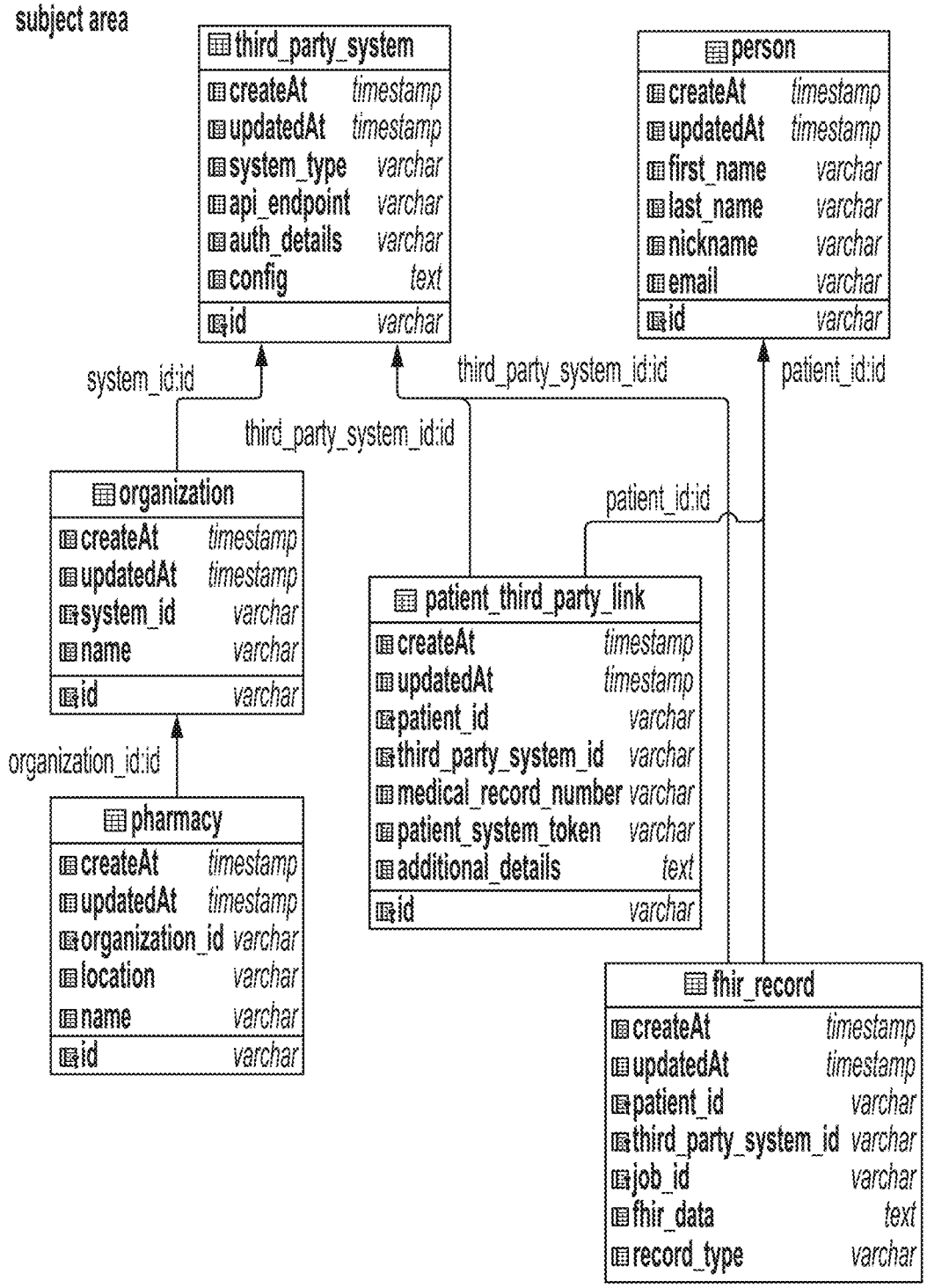
FIG. 20 illustrates a non-limiting diagram of an exemplary connectivity configuration for integrations databases.

As shown in FIG. 20, the integrations subject area may comprise a plurality of modules to connect metadata to external data providers (e.g., Epic). In some embodiments, the metadata may be used to manage system level access to third party system APIs and user-specific account access details needed to present information like prescription details to users. In some embodiments, the integrations subject area may comprise a plurality of databases, algorithms, datasets, matrices, or any combination thereof.

Figure 21:
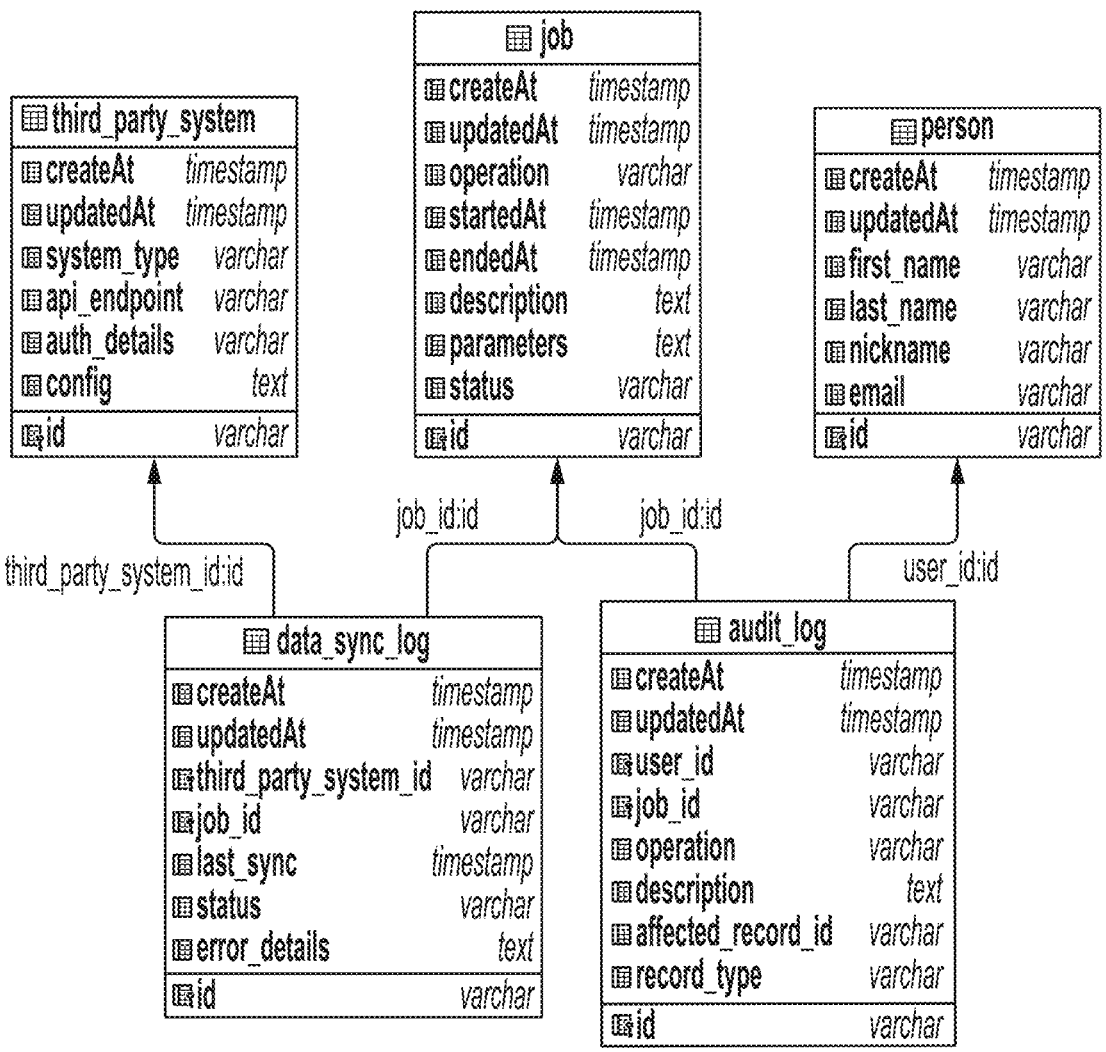
FIG. 21 illustrates a non-limiting diagram of an exemplary connectivity configuration for operations databases.
Figure 22:
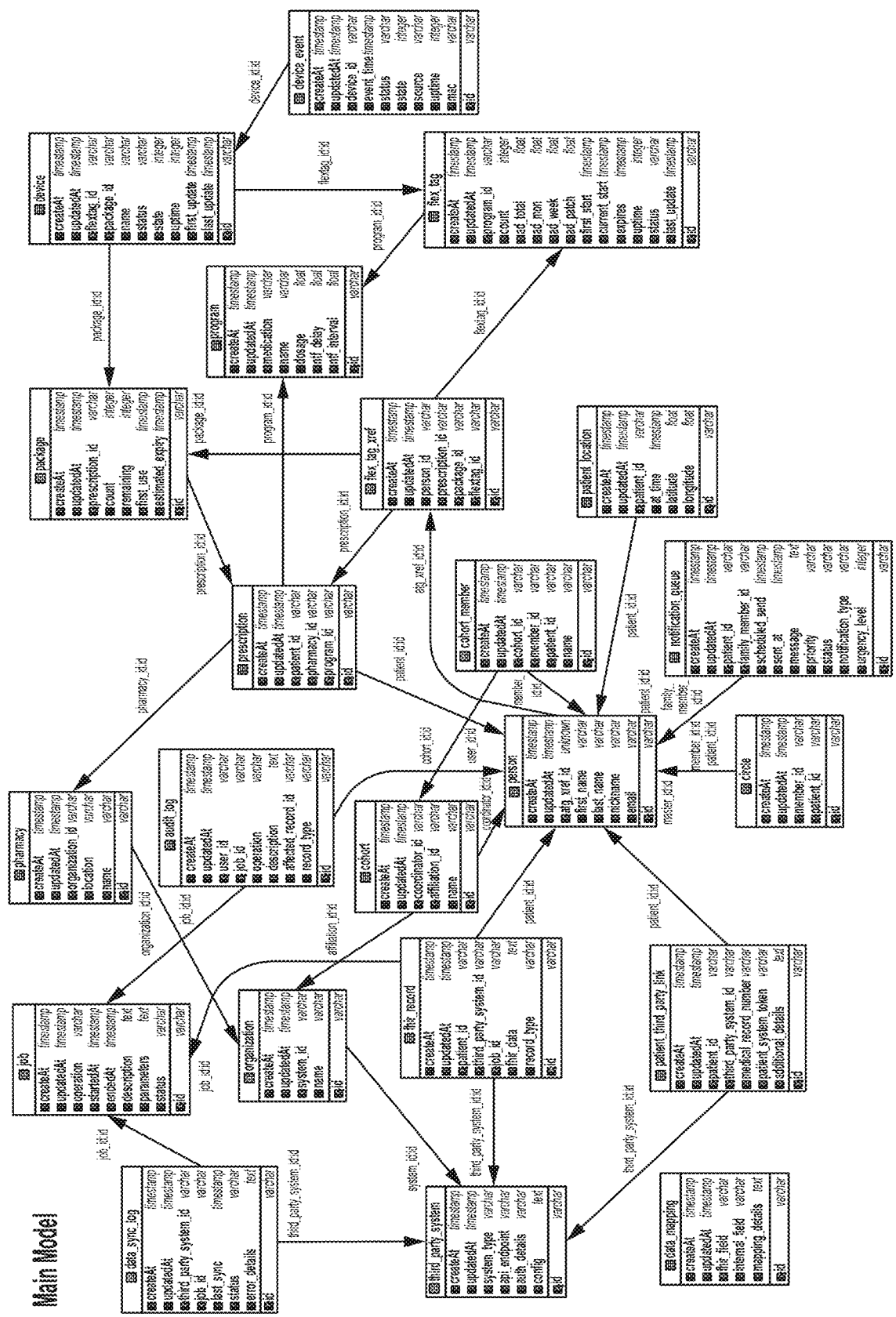
FIG. 22 illustrates a non-limiting diagram of an exemplary connectivity configuration for various databases.

As shown in FIG. 21, in some embodiments, the operations subject area may comprise a plurality of modules that can track application-level operations like job execution schedules, job logging, and administrative edits to patient records. In some embodiments, the plurality of modules can work in concert with one or more authentication databases, for example AWS Cloudwatch and Cloudtrail, which may provide detailed lower-level information. In some embodiments, the operations subject area may comprise a plurality of databases, algorithms, datasets, matrices, or any combination thereof.

In some embodiments, the main model subject area may comprise some combination of one or more subject areas, such as the operations subject area, integrations subject area, member subject area, electronics subject area, or any combination thereof.

In some embodiments, mobile platforms may not accept notifications without user permission. In some embodiments, when a user grants permission to the application, a permission token may be generated and stored with user details. In some embodiments, the SNS may retrieve this token when delivering the message.

In some embodiments, the TET platform may serve as a reminder manager for a patient's TET smart patch and medication routines. In some embodiments, information about the medication regiment can be shared with a person other than the user, such as with a trusted circle of family members and friends. In some embodiments, the TET platform may track smart patch status. In some embodiments, the TET platform may send increasingly urgent alerts to all members of a patient's circle if a smart patch change is missed. In some embodiments, the TET platform may comprise pharmacy prescription information for the smart patch.

In some embodiments, the application may use a pill-box carousel metaphor to present a patient's smart patch and medication routine status. In some cases, the carousel metaphor may comprise a setup with columns of the carousel representing different days and each row representing a time of day when a collection of pills should be taken. In some embodiments, the TET smart patch may be represented as a ribbon across the top row, indicating that its use is automatic and extends across many days.

In some embodiments, the carousel can use color, iconography, or words, or any combination thereof to indicate the current status. In some embodiments, touch screen or voice interfaces can facilitate interactions concerning details of each routine. In some embodiments, each screen may provide easy access to communication tools and alert details.

In some embodiments, both mobile applications and devices such as Amazon Echo can synchronize with the same AWS cloud backend. In some embodiments, medication schedules, smart patch status, or circle member interactions can be updated to be current across all devices.

In some cases, the mobile application may be written in TypeScript using the Ionic Framework structure.

In some cases, data for the mobile application may be retrieved from the cloud. In some cases, the data may be retrieved for example using GraphQL through AppSync. In some embodiments, data elements retrieved from the cloud may be mapped to visual elements on the screen using standard model or view patterns based on style sheets and the Typescript template model. In some embodiments, the user may interact with the data elements using a GUI.

In some embodiments, data updates may be pushed to the phone from the cloud automatically. In some cases, the updates may enable all users to see the same information at the same time.

In some embodiments, the mobile application may provide a service layer that operates in the background while the application is off screen. In some embodiments, this layer may manage BLE connectivity using native features implemented in a device-dependent way (e.g., with Swift on iOS devices).

In some embodiments, connections between the service layer and the user interface layer may be minimized. In some embodiments, the mobile application may display the latest information from a connected smart patch without an internet connection. In some embodiments, the mobile application may comprise a BLE Connection, BLE Advertisement Forwarding, Beacon discovery, or location updates, or any combination thereof. In some embodiments, the mobile application may comprise a separate simple scheduling service that allows developer configuration of certain update intervals.

In some embodiments, voice or touch commands may trigger interactions directly with the cloud. In some cases, these interactions may trigger Lambda functions running in the cloud that pull information back to the user's device.

In some embodiments, all devices can receive alerts when an urgent condition is detected. In some embodiments, all devices can receive alerts for scheduled reminders. In some embodiments, the system may utilize push notifications to alert users of medication times, smart patch application reminders, or any required actions. In some embodiments, the system may present users with urgent alerts designed to override device settings for immediate attention. In some embodiments, interacting with a notification may cause the application to open to a relevant display. In some embodiments, circle members can reach out directly to the patient from the app, using standard phone video calling, text messaging, recorded voice notes, or the Alexa application.

Figure 23:
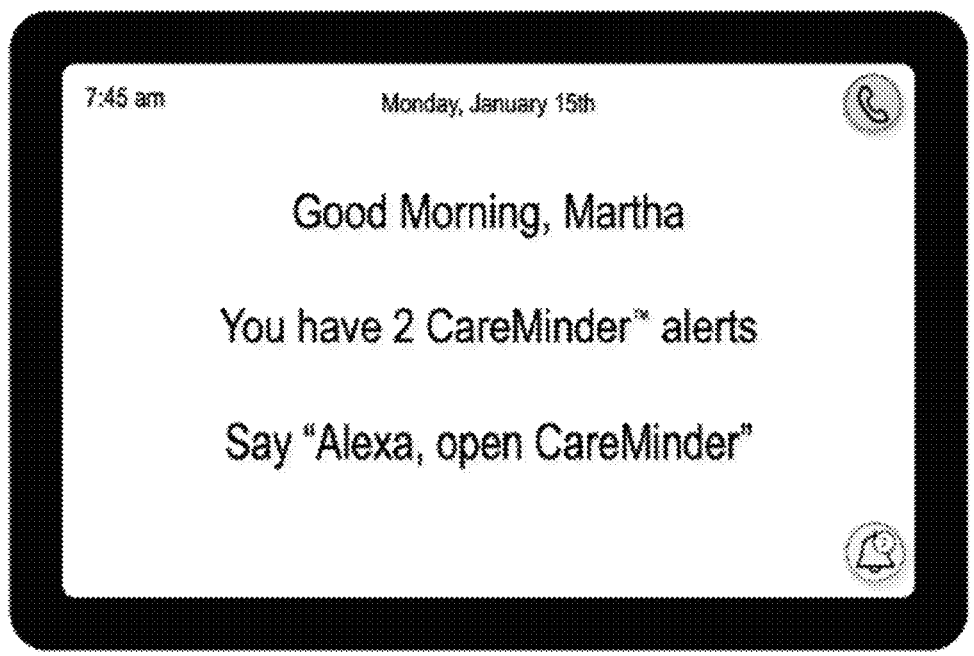
FIG. 23 illustrates a non-limiting example of a graphic user interface (GUI), in this case, a GUI providing an introductory notification to a user.

FIG. 23 shows a graphic user interface (GUI) as an exemplary user interface e.g., a home screen of the TET platform. In some embodiments, the GUI may show a notification, e.g., a morning notification from CareMinder. As used herein, CareMinder generically refers to any software-based application allowing a user to interface with a TET platform. In some embodiments, CareMinder comprises a graphic user interface (GUI) that can facilitate interactions of one or more users with a TET platform. In some embodiments, CareMinder can interface with one or more interpersonal contact applications to communicate with one or more people in the patient's care circle. In some embodiments, the GUI may display a settings call menu icon as shown in FIG. 23, for example. In some embodiments, the GUI may display a notification indicator in the as shown, for example, in FIG. 23. In some embodiments, the indicator can show the presence of one or more notices, for example in FIG. 23 displaying two notices. In some embodiments, the user (e.g., Martha) can activate the system by touch activation, voice activation, tapping activation, or any combination thereof, for example the user can tap the screen or say "Alexa, open CareMinder" to activate the system.

Figure 24:
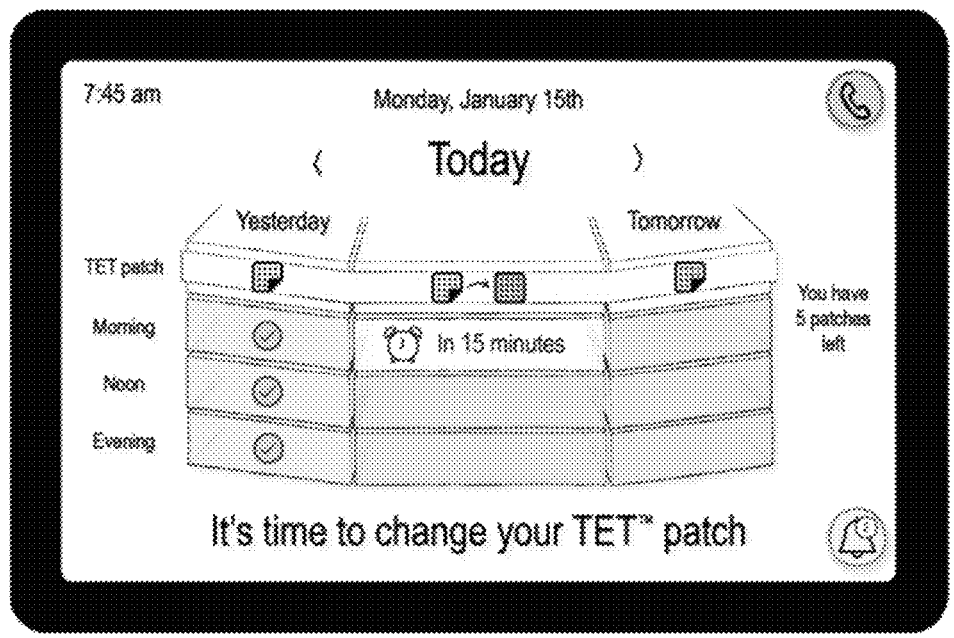
FIG. 24 illustrates a non-limiting example of a GUI, in this case, a GUI providing a routine manager and reminder manager.

FIG. 24 shows an exemplary user interface (a screen) of the TET platform. In some embodiments, the GUI can show pre-configured timeslots (routines) during the day. In some embodiments, the GUI can show a snapshot of one or more days relative to the current day, for example, yesterday, today, and tomorrow with various indications. In some embodiments, the GUI can display across the top of the screen an unbroken ribbon, which can represent the active TET smart patch. In some embodiments, when the ribbon is in yellow, it can indicate it is time to replace the smart patch. In some embodiments, the GUI can show completed routines at one or more times of the day, for example the morning, noon, and evening routines. In some embodiments, in the middle of the screen, the GUI can show, for example, the morning routine is in a certain amount of time, for example 15 minutes. In some embodiments, the GUI can also show the number of remaining smart patches. In some embodiments, a user can tap the screen in the center area to see the details of the routines. In some embodiments, the system can be voiced enabled. In some embodiments, instead of tapping the screen, the user can command the system to act.

Figure 25:
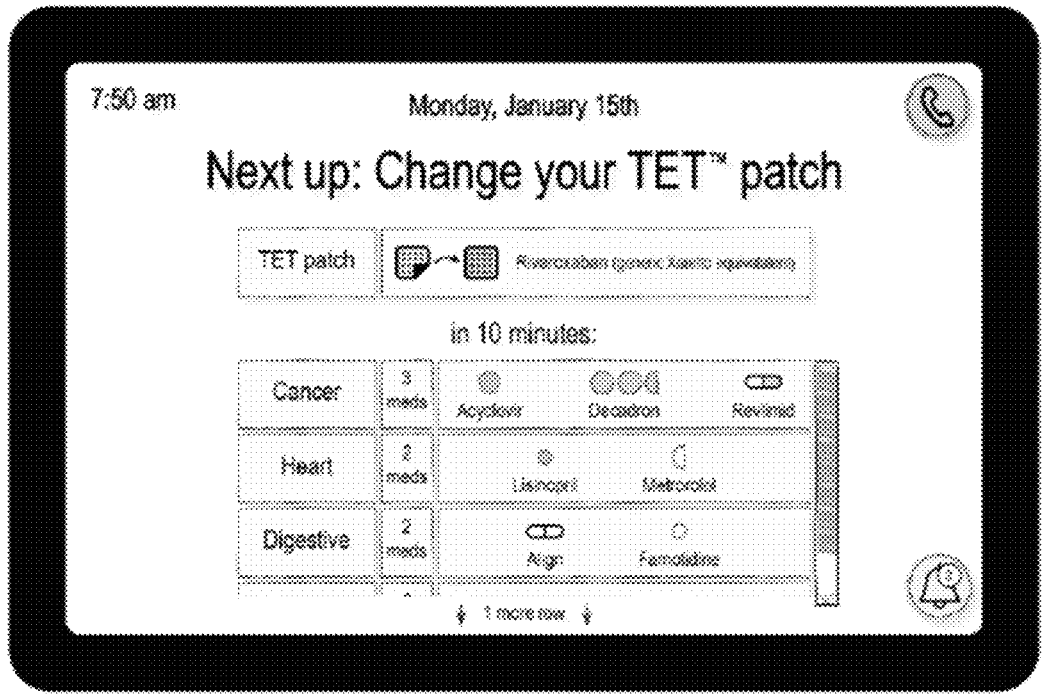
FIG. 25 illustrates a non-limiting example of a GUI, in this case, a GUI providing a routine manager.

In some embodiments, FIG. 25 shows an exemplary GUI with a plurality of routines. In some embodiments, the GUI can comprise a plurality of columns and rows, like a compartment in a pill box. In some embodiments, the system can store a plurality of routines a day. In some embodiments, the system can track which medication, and how much, is required for each time slot. In some embodiments, graphics can represent realistic shapes and colors for each pill. In FIG. 25, for example, since it is time for the user to change her rivaroxaban smart patch, this is highlighted first. In FIG. 25, for example, the top of the screen shows "next up: change your TET smart patch". In some embodiments, on the GUI, future details are visible and can scroll vertically if needed. In some embodiments, the GUI can show other routines for other medications, e.g., type of medication, doses each day, medication time, etc. In some embodiments, when the user opens the TET smart patch and applies it, the Cloud can be notified. In some embodiments, when the Cloud is notified, the application can be updated. In some embodiments, the GUI can automatically change without any interaction.

Figure 26:
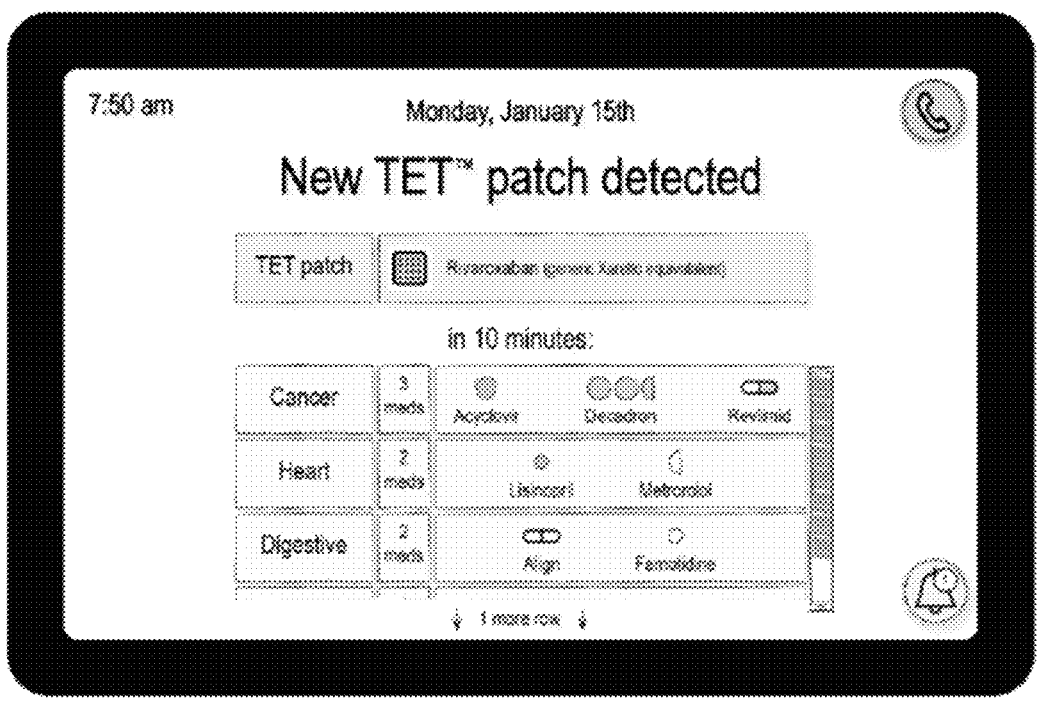
FIG. 26 illustrates a non-limiting example of a GUI, in this case, a GUI providing a notification of a new Tech-Enabled Therapeutics (TET) smart patch detection and a routine manager.

FIG. 26 shows an exemplary updated GUI when a smart patch is detected. In FIG. 26, for example, the smart patch status indicates new TET smart patch is detected. In some embodiments, the color for the smart patch routine may change, e.g., from yellow to green. In FIG. 26, for example, the next routine is highlighted in yellow, and the icon in the lower right indicates one more reminder. In some embodiments, the details can change dynamically as the user goes through different routines during the day. In FIG. 26, for example, the screen shows the user's other routines for this Monday morning, both medication to take and the number of pills for each. In some embodiments, the user can complete the regimen and say, "Alexa, I took my medicine" to change the status for each of the routine.

Figure 27:
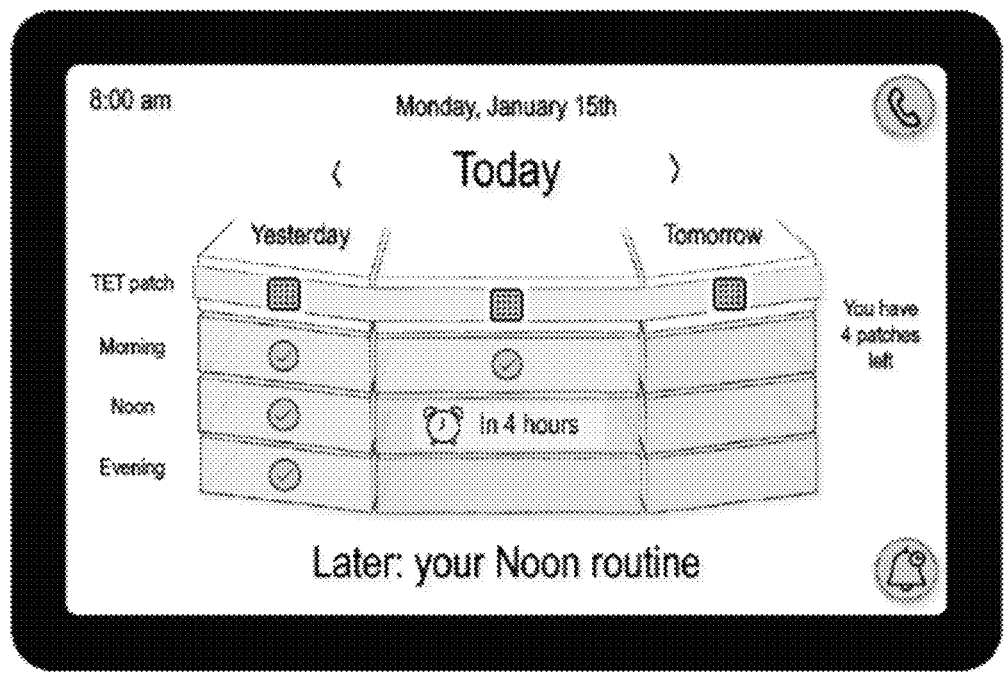
FIG. 27 illustrates a non-limiting example of a GUI, in this case, a GUI providing a completed routine in a routine manager.
Figure 28:
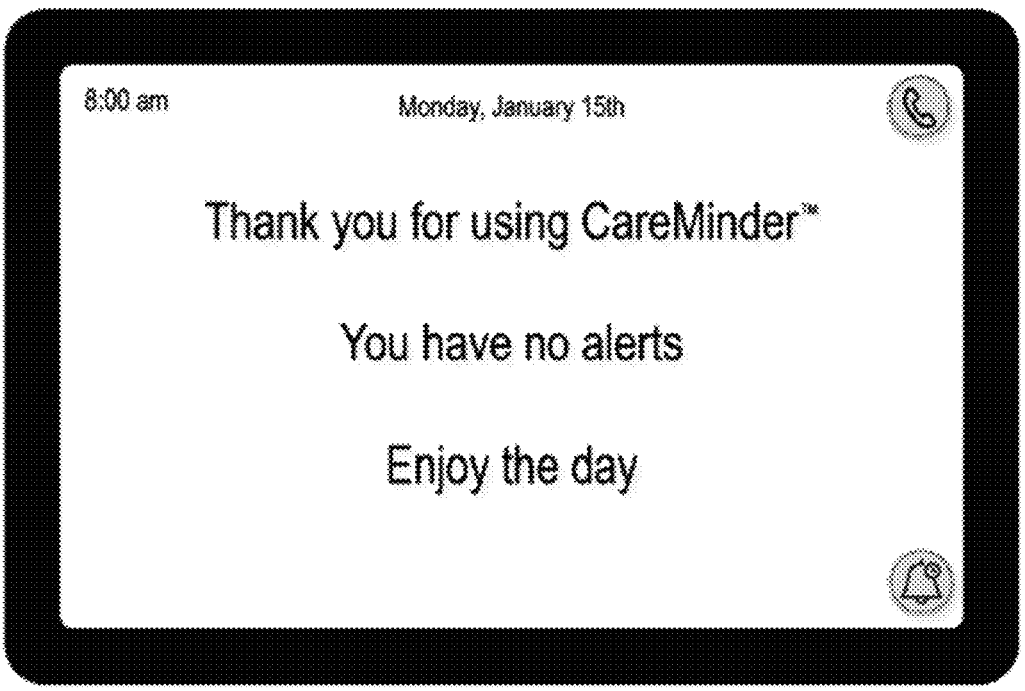
FIG. 28 illustrates a non-limiting example of a GUI, in this case, a GUI providing a notification to the user of no alerts.

FIG. 27 shows an exemplary updated GUI when the morning routine is completed. In FIG. 27, for example, Martha has replaced her smart patch, which now shows a green status across the ribbon. In FIG. 27, for example, she has completed her morning routine, as the green check icons indicate. In FIG. 27, the pill box notes the time until the next routine. In FIG. 27 and FIG. 28, for example, there are no active reminders, so that reminder icon shows green. In FIG. 27 and FIG. 28, for example, Martha can say "Alexa, close CareMinder" to put the system to sleep mode when no medications remain to be taken. As shown in FIG. 28, for example, the screen shows no alerts.

Figure 29:
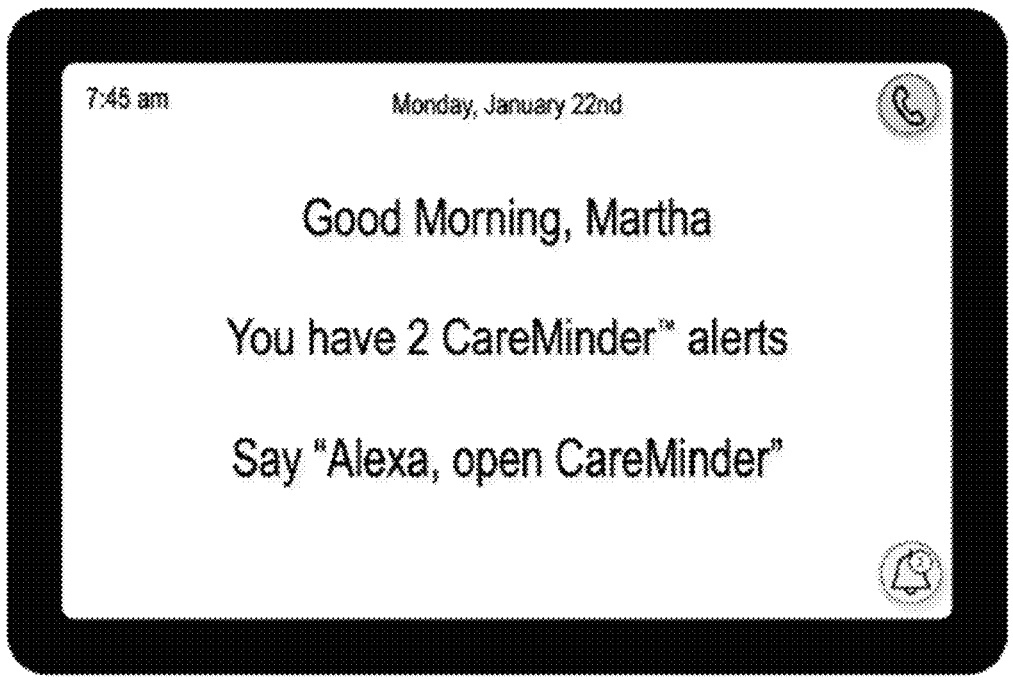
FIG. 29 illustrates a non-limiting example of a GUI, in this case, a GUI providing an introductory notification to a user, and a notification of the presence of one or more alerts to the user.

FIG. 29, for example, shows another exemplary GUI e.g., a home screen of the TET platform. In some embodiments, the GUI may show a notification, e.g., a morning notification from CareMinder as shown in FIG. 29. In some embodiments, the GUI may display settings call menu icon in the upper right and a notification indicator in the lower right. In FIG. 29, for example, the indicator shows there are two notices. In some embodiments, the user (e.g., Martha as shown in FIG. 29) can activate the system by voice command or touch command, for example, the user can tap the screen or say "Alexa, open CareMinder" to activate the system.

Figure 30:
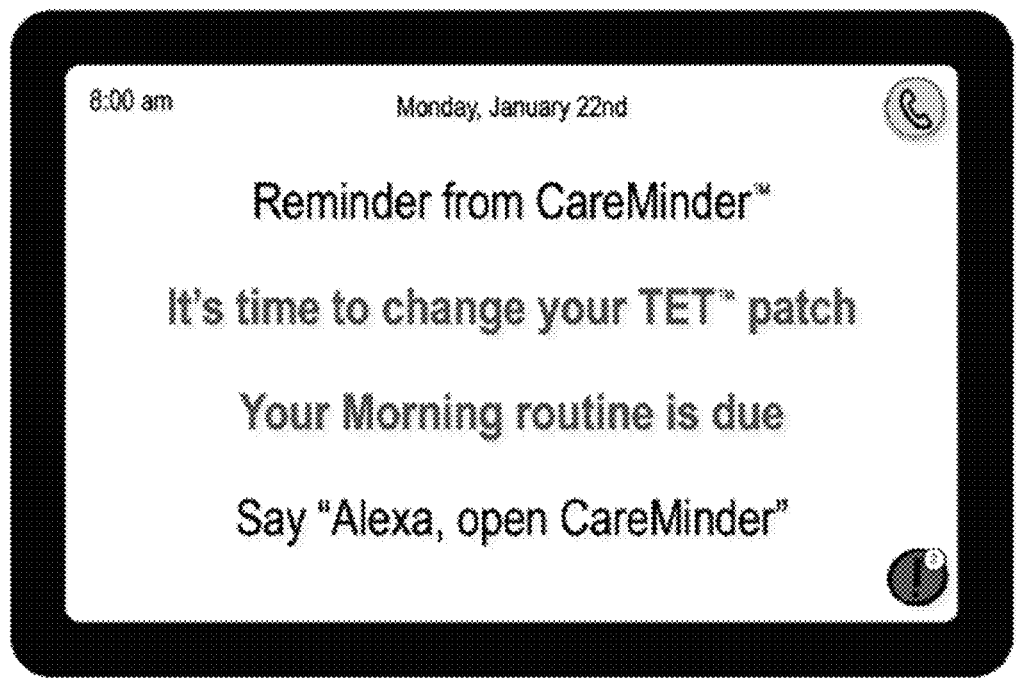
FIG. 30 illustrates a non-limiting example of a GUI, in this case, a GUI providing a reminder to the user that a routine is due and a change of TET smart patch is due.

FIG. 30 shows another exemplary GUI e.g., a home screen of the TET platform if the morning routine is due. In FIG. 30, for example, the notification icon turned red and the screen shows "Reminder from CareMinder. It's time to change your TET smart patch. Your morning routine is due". As shown in FIG. 30, for example, the user (e.g., Martha) can tap the screen or say "Alexa, open CareMinder" to activate the system. In some embodiments, if the user is not ready, they can ask the system to send a reminder later, e.g., say "Alexa, remind me in 15 minutes."

Figure 31:
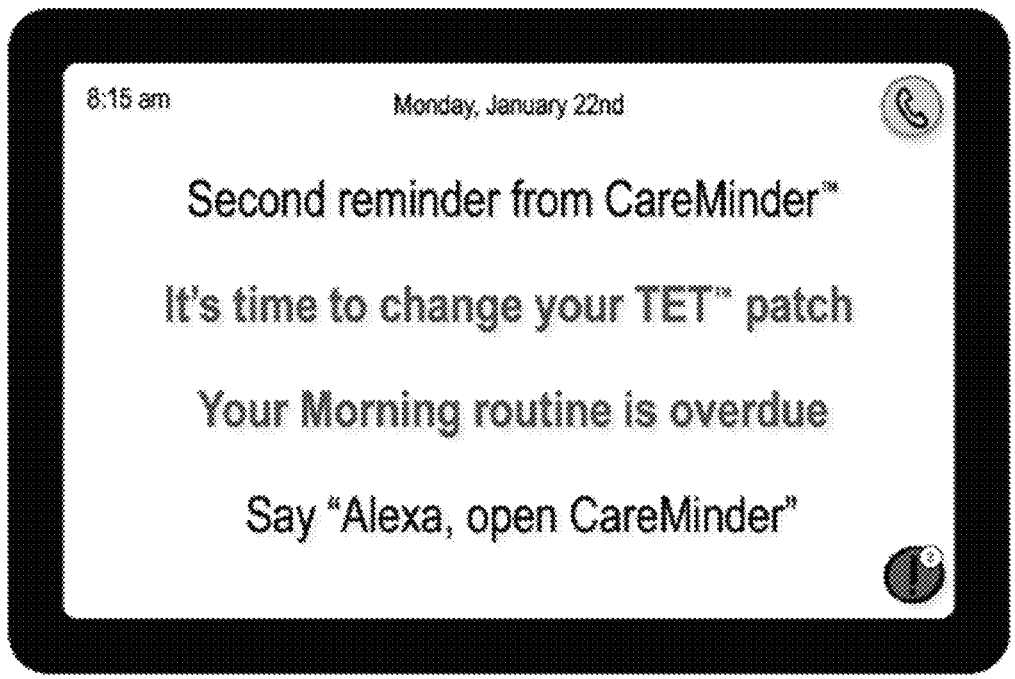
FIG. 31 illustrates a non-limiting example of a GUI, in this case, a GUI providing a second reminder to the user that a routine is due and a change of TET smart patch is due.

FIG. 31 shows another exemplary user interface e.g., a home screen of the TET platform if the morning routine is overdue. As in FIG. 31, for example, the notification icon is red and the screen shows "Second reminder from CareMinder. It's time to change your TET smart patch. Your morning routine is overdue". In some embodiments, a circle member can receive a notification on his/her device indicating the user has not checked in. In some embodiments, the user (e.g., Martha as shown in FIG. 31) can tap the screen or say "Alexa, open CareMinder" to activate the system.

Figure 32:
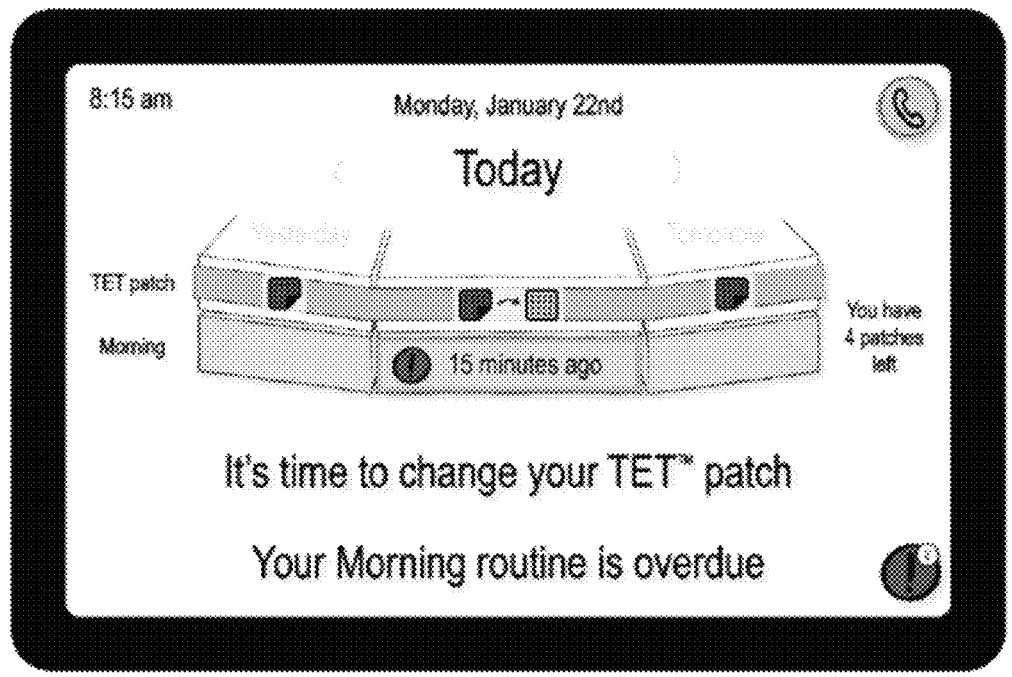
FIG. 32 illustrates a non-limiting example of a GUI, in this case, a GUI providing a routine manager having one or more overdue routine elements.

FIG. 32 shows an exemplary GUI when there is an action overdue. In FIG. 32, for example, the TET smart patch ribbon is duplicated for emphasis, and the Morning routine is highlighted in red. In some embodiments, icons like the checkmarks seen on other days can be removed, and most navigation can be disabled to highlight the current need.

Figure 33:
FIG. 33 illustrates a non-limiting example of a GUI, in this case, a GUI providing a notification alert to a designated person other than the user of one or more overdue routine elements.
Figure 34:
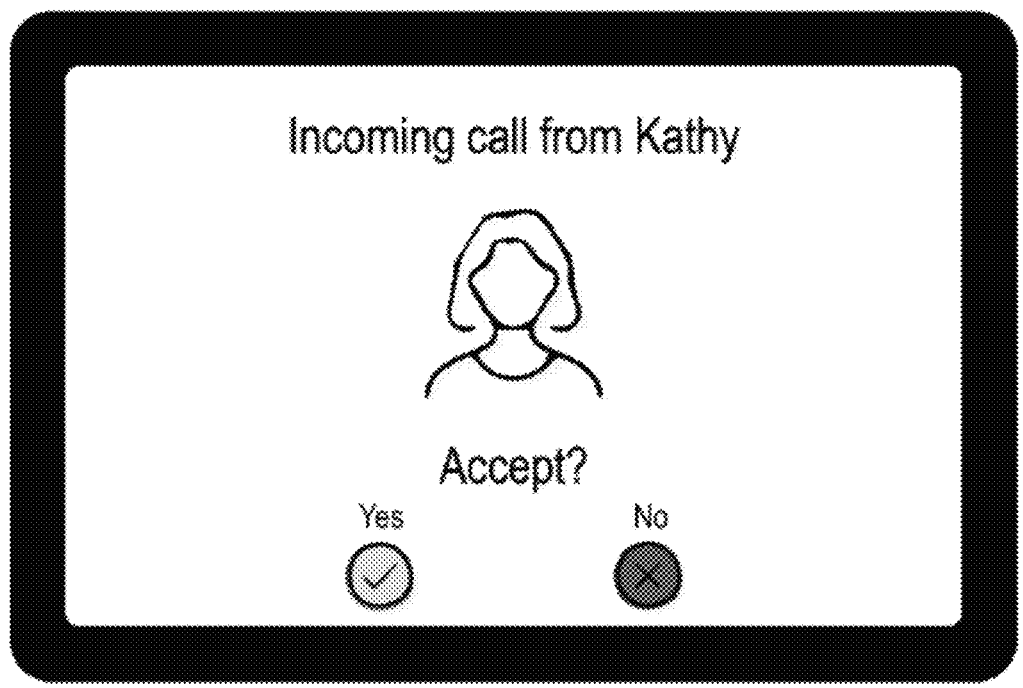
FIG. 34 illustrates a non-limiting example of a GUI, in this case, a GUI providing a notification of a call from a person other than the user.

FIG. 33 shows an exemplary screen of a circle member (e.g., Kathy, Martha's daughter). In some embodiments, the circle member's screen can show one or more alerts that the user is off schedule for the critical dose medications. In FIG. 33, for example, when Kathy selects the notification, the CareMinder phone application launches, showing the same details seen on Martha's screen. In FIG. 33, for example, because Martha has enabled Kathy to see her location, Kathy can tell that her mother is at home. In FIG. 33, for example, because the applications share information through the cloud, Kathy has access to the same information at the same time that Martha can see it. As shown in FIG. 34, for example, Kathy can contact her mother to make sure everything is ok.

Figure 35:
FIG. 35 illustrates a non-limiting example of a GUI, in this case, a GUI providing a notification to a person other than the user that a new TET smart patch has been detected.

In some embodiments, an edge device can receive contact data from one or more people in the patient's care circle. For example, a device such as an Echo can receive video or voice calls. In some embodiments, some circumstances can allow a "drop in" call where approved user or circle member can directly open a connection as shown in FIG. 34. FIG. 34 shows, for example, that Martha receives a video call from Kathy while she is looking at the CareMinder screen. In some embodiments, as shown in FIG. 35, if the user replaces the smart patch, the circle member can receive a notice that the new smart patch is detected. In some embodiments, if the user has not completed a morning routine, the system can send an alert to a member of the patient's care circle that the patient's morning routine is overdue. In some cases, the name of the patient can be customized. As shown in FIG. 35, since the user has not completed the morning routine yet, the circle member's screen shows "mom's morning routine is overdue". In some embodiments, if the user replaces the smart patch and completes the routine, the circle member can get a notice that the new smart patch is active and the routine is complete.

Figure 36:
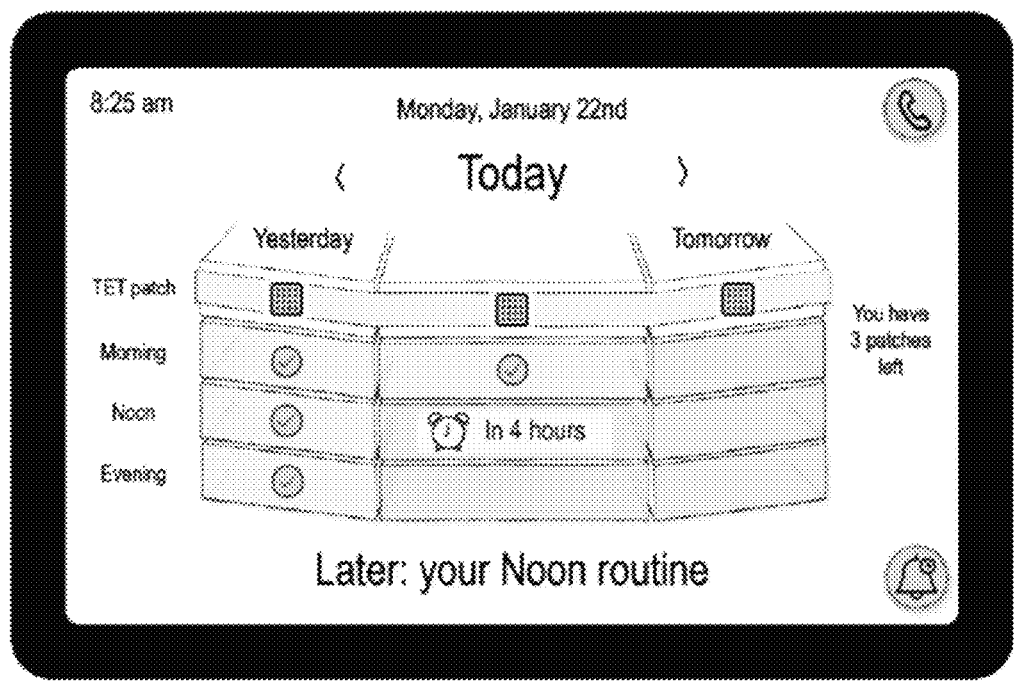
FIG. 36 illustrates a non-limiting example of a GUI, in this case, a GUI providing a routine manager having all routine elements completed.

FIG. 36 shows an exemplary screen after the morning routine is complete. As shown in FIG. 36 for example, Martha has replaced her smart patch, which now shows a green status across the ribbon. In FIG. 36 for example, she has completed her morning routine, as the green check icons indicate. In FIG. 36, for example, the pill box can note the time until the next routine. In some embodiments, where there are no active reminders, so the reminder icon can appear green. In FIG. 36, for example, Martha can say "Alexa, close CareMinder" to put the system to sleep mode.

Figure 37:
FIG. 37 illustrates a non-limiting example of a GUI, in this case, a GUI providing a notification to a person other than the user that one or more routine elements are completed.

FIG. 37 shows exemplary GUI displays of the circle member after the user's morning routine is complete. In FIG. 37, for example, the GUI shows the new TET smart patch is detected and the morning routine is done. Additionally, in FIG. 37, for example, the next GUI display shows the next routine is in 4 hours.

In some embodiments, a transdermal drug delivery smart patch can comprise a drug-containing layer; a communication interface; a processor communicatively coupled to the communication interface, wherein the processor can be configured to perform operations comprising: (a) receiving a wireless signal or electric current through the communication interface; and (b) releasing a (e.g., predetermined) amount of drug from the drug-containing layer. In some embodiments, the processor can comprise a system-on-a-chip (SoC). In some embodiments, the SoC can comprise one or more of a messaging subsystem, a sensor subsystem, a power state subsystem, a communication state subsystem, a communication subsystem, a printable battery, or an event cache subsystem, or any combination thereof.

In some embodiments, the printable battery may enter a low-power mode. In some embodiments, the printable battery may enter a low-power mode as a result of communication from the communication subsystem of the TET smart patch. In some embodiments, the printable battery may enter a low-power mode as a result of a communication from a cloud module. In some embodiments, the printable battery may enter a low-power mode in response to a signal from one or more sensors. In some embodiments, the printable battery can enter a low-power mode to preserve battery and extend battery life. In some embodiments, the printable battery can enter a low-power mode as a result of a signal for a change of the TET smart patch from work mode to sleep or hibernation mode. In some embodiments, the printable battery may exit a low-power mode. In some embodiments, the printable battery may exit a low-power mode as a result of communication from the communication subsystem of the TET smart patch. In some embodiments, the printable battery may exit a low-power mode as a result of a communication from a cloud module. In some embodiments, the printable battery may exit a low-power mode in response to a signal from one or more sensors. In some embodiments, the printable battery can exit a low-power mode to preserve battery and extend battery life. In some embodiments, the printable battery can exit a low-power mode as a result of a signal for a change of the TET smart patch from sleep or hibernation mode to work mode.

In some embodiments, the communication subsystem can receive data from a cloud server system using the wireless signal or the electric current. In some embodiments, one or more drugs can be loaded on the drug-containing layer. In some embodiments one or more drugs can be lipophilic or hydrophilic. In some embodiments, one or more placebos can be loaded on the drug-containing layer. In some embodiments, the drug-containing layer can comprise a layer of drug-in-adhesive. In some embodiments, the drug-containing layer can comprise a plurality of layers of drug-in-adhesive and a membrane positioned therebetween. In some embodiments, the drug-containing layer can comprise a drug reservoir, an adhesive layer, and a membrane positioned therebetween. In some embodiments, the drug-containing layer can comprise a drug reservoir and an adhesive ring therearound. In some embodiments, the drug-containing layer can comprise a drug-containing microneedle array and an adhesive layer. In some embodiments, the drug-containing layer can comprise one or more excipients that facilitate (i) permeation of the drug through the skin and (ii) drug delivery. In some embodiments, one or more excipients can comprise one or more chemical enhancers. In some embodiments, the wireless signal or the electric current received by the communication interface can be associated with releasing the drug.

Computing Systems

Figure 38:
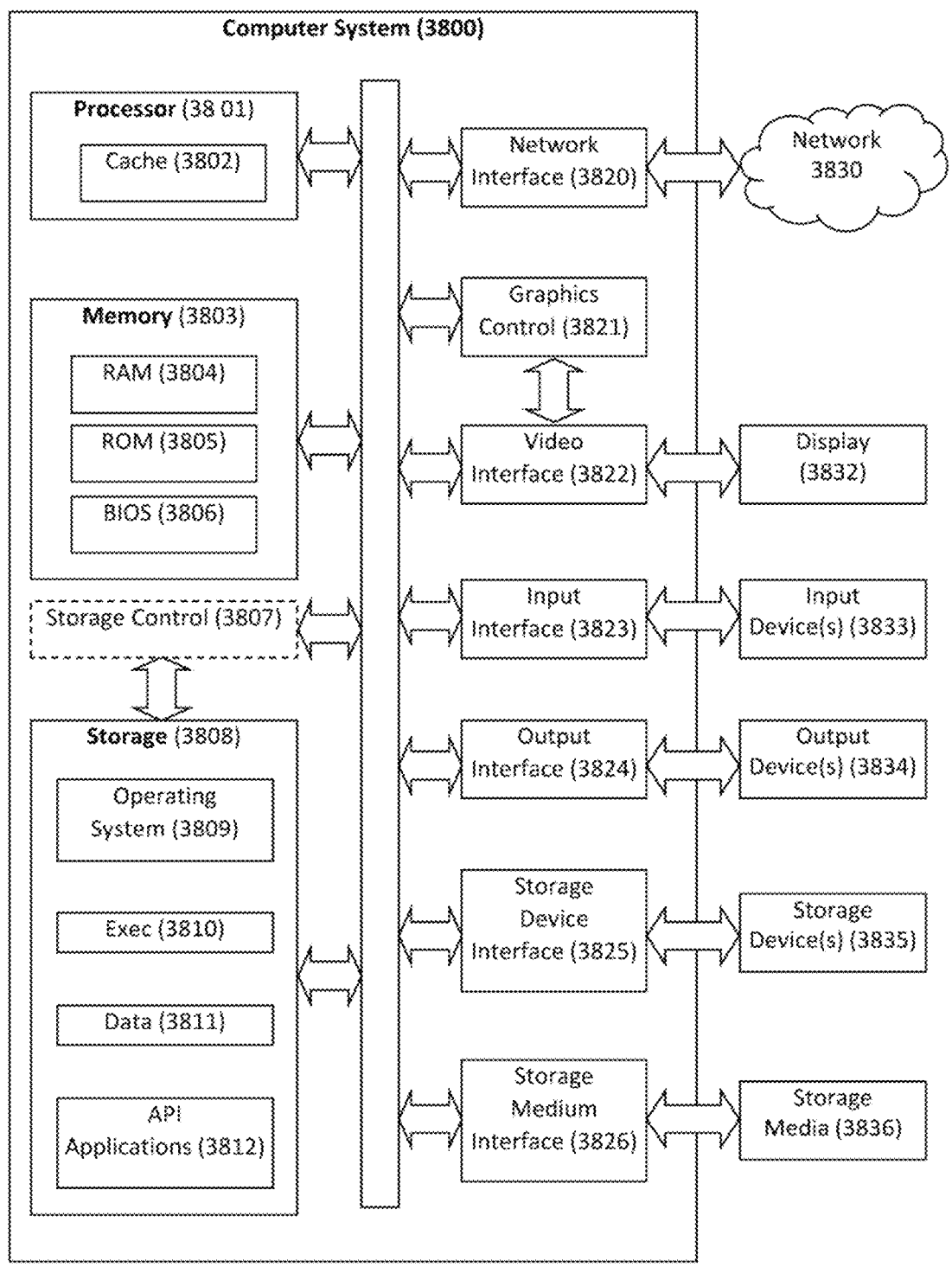
FIG. 38 shows a non-limiting example of a computing device; in this case, a device with one or more processors, memory, storage, and a network interface, per one or more embodiments herein.

Referring to FIG. 38, a block diagram is shown depicting an exemplary machine that includes a computer system 3800 (e.g., a processing or computing system) within which a set of instructions can execute for causing a device to perform or execute any one or more of the aspects and/or methodologies for static code scheduling of the present disclosure. The components in FIG. 38 are examples only and do not limit the scope of use or functionality of any hardware, software, embedded logic component, or a combination of two or more such components implementing particular embodiments.

Computer system 3800 may include one or more processors 38038, a memory 3803, and a storage 3808 that communicate with each other, and with other components, via a bus 3840. The bus 3840 may also link a display 3832, one or more input devices 3833 (which may, for example, include a keypad, a keyboard, a mouse, a stylus, etc.), one or more output devices 3834, one or more storage devices 3835, and various tangible storage media 3836. All of these elements may interface directly or via one or more interfaces or adaptors to the bus 3840. For instance, the various tangible storage media 3836 can interface with the bus 3840 via storage medium interface 3826. Computer system 3800 may have any suitable physical form, including but not limited to one or more integrated circuits (ICs), printed circuit boards (PCBs), mobile handheld devices (such as mobile telephones or PDAs), laptop or notebook computers, distributed computer systems, computing grids, or servers.

Computer system 3800 includes one or more processor(s) 38038 (e.g., central processing units (CPUs) or general purpose graphics processing units (GPGPUs)) that carry out functions. Processor(s) 38038 optionally contains a cache memory unit 3802 for temporary local storage of instructions, data, or computer addresses. Processor(s) 38038 are configured to assist in execution of computer readable instructions. Computer system 3800 may provide functionality for the components depicted in FIG. 38 as a result of the processor(s) 38038 executing non-transitory, processor-executable instructions embodied in one or more tangible computer-readable storage media, such as memory 3803, storage 3808, storage devices 3835, and/or storage medium 3836. The computer-readable media may store software that implements particular embodiments, and processor(s) 38038 may execute the software. Memory 3803 may read the software from one or more other computer-readable media (such as mass storage device(s) 3835, 3836) or from one or more other sources through a suitable interface, such as network interface 3820. The software may cause processor(s) 38038 to carry out one or more processes or one or more steps of one or more processes described or illustrated herein. Carrying out such processes or steps may include defining data structures stored in memory 3803 and modifying the data structures as directed by the software.

The memory 3803 may include various components (e.g., machine readable media) including, but not limited to, a random access memory component (e.g., RAM 3804) (e.g., static RAM (SRAM), dynamic RAM (DRAM), ferroelectric random access memory (FRAM), phase-change random access memory (PRAM), etc.), a read-only memory component (e.g., ROM 3805), and any combinations thereof. ROM 3805 may act to communicate data and instructions unidirectionally to processor(s) 38038, and RAM 3804 may act to communicate data and instructions bidirectionally with processor(s) 38038. ROM 3805 and RAM 3804 may include any suitable tangible computer-readable media described below. In one example, a basic input/output system 3806 (BIOS), including basic routines that help to transfer information between elements within computer system 3800, such as during start-up, may be stored in the memory 3803.

Fixed storage 3808 is connected bidirectionally to processor(s) 38038, optionally through storage control unit 3807. Fixed storage 3808 provides additional data storage capacity and may also include any suitable tangible computer-readable media described herein. Storage 3808 may be used to store operating system 3809, executable(s) 38380, data 383838, applications 38382 (application programs), and the like. Storage 3808 can also include an optical disk drive, a solid-state memory device (e.g., flash-based systems), or a combination of any of the above. Information in storage 3808 may, in appropriate cases, be incorporated as virtual memory in memory 3803.

In one example, storage device(s) 3835 may be removably interfaced with computer system 3800 (e.g., via an external port connector (not shown)) via a storage device interface 3825. Particularly, storage device(s) 3835 and an associated machine-readable medium may provide non-volatile and/or volatile storage of machine-readable instructions, data structures, program modules, and/or other data for the computer system 3800. In one example, software may reside, completely or partially, within a machine-readable medium on storage device(s) 3835. In another example, software may reside, completely or partially, within processor(s) 38038.

Bus 3840 connects a wide variety of subsystems. Herein, reference to a bus may encompass one or more digital signal lines serving a common function, where appropriate. Bus 3840 may be any of several types of bus structures including, but not limited to, a memory bus, a memory controller, a peripheral bus, a local bus, and any combinations thereof, using any of a variety of bus architectures. As an example and not by way of limitation, such architectures include an Industry Standard Architecture (ISA) bus, an Enhanced ISA (EISA) bus, a Micro Channel Architecture (MCA) bus, a Video Electronics Standards Association local bus (VLB), a Peripheral Component Interconnect (PCI) bus, a PCI-Express (PCI-X) bus, an Accelerated Graphics Port (AGP) bus, HyperTransport (HTX) bus, serial advanced technology attachment (SATA) bus, and any combinations thereof.

Computer system 3800 may also include an input device 3833. In one example, a user of computer system 3800 may enter commands and/or other information into computer system 3800 via input device(s) 3833. Examples of an input device(s) 3833 include, but are not limited to, an alphanumeric input device (e.g., a keyboard), a pointing device (e.g., a mouse or touchpad), a touchpad, a touch screen, a multi-touch screen, a joystick, a stylus, a gamepad, an audio input device (e.g., a microphone, a voice response system, etc.), an optical scanner, a video or still image capture device (e.g., a camera), and any combinations thereof. In some embodiments, the input device is a Kinect, Leap Motion, or the like. Input device(s) 3833 may be interfaced to bus 3840 via any of a variety of input interfaces 3823 (e.g., input interface 3823) including, but not limited to, serial, parallel, game port, USB, FIREWIRE, THUNDERBOLT, or any combination of the above.

In particular embodiments, when computer system 3800 is connected to network 3830, computer system 3800 may communicate with other devices, specifically mobile devices and enterprise systems, distributed computing systems, cloud storage systems, cloud computing systems, and the like, connected to network 3830. Communications to and from computer system 3800 may be sent through network interface 3820. For example, network interface 3820 may receive incoming communications (such as requests or responses from other devices) in the form of one or more packets (such as Internet Protocol (IP) packets) from network 3830, and computer system 3800 may store the incoming communications in memory 3803 for processing. Computer system 3800 may similarly store outgoing communications (such as requests or responses to other devices) in the form of one or more packets in memory 3803 and communicated to network 3830 from network interface 3820. Processor(s) 38038 may access these communication packets stored in memory 3803 for processing.

Examples of the network interface 3820 include, but are not limited to, a network interface card, a modem, and any combination thereof. Examples of a network 3830 or network segment 3830 include, but are not limited to, a distributed computing system, a cloud computing system, a wide area network (WAN) (e.g., the Internet, an enterprise network), a local area network (LAN) (e.g., a network associated with an office, a building, a campus or other relatively small geographic space), a telephone network, a direct connection between two computing devices, a peer-to-peer network, and any combinations thereof. A network, such as network 3830, may employ a wired and/or a wireless mode of communication. In general, any network topology may be used.

Information and data can be displayed through a display 3832. Examples of a display 3832 include, but are not limited to, a cathode ray tube (CRT), a liquid crystal display (LCD), a thin film transistor liquid crystal display (TFT-LCD), an organic liquid crystal display (OLED) such as a passive-matrix OLED (PMOLED) or active-matrix OLED (AMOLED) display, a plasma display, and any combinations thereof. The display 3832 can interface to the processor(s) 38038, memory 3803, and fixed storage 3808, as well as other devices, such as input device(s) 3833, via the bus 3840. The display 3832 is linked to the bus 3840 via a video interface 3822, and transport of data between the display 3832 and the bus 3840 can be controlled via the graphics control 38238. In some embodiments, the display is a video projector. In some embodiments, the display is a head-mounted display (HMD) such as a VR headset. In further embodiments, suitable VR headsets include, by way of non-limiting examples, HTC Vive, Oculus Rift, Samsung Gear VR, Microsoft HoloLens, Razer OSVR, FOVE VR, Zeiss VR One, Avegant Glyph, Freefly VR headset, and the like. In still further embodiments, the display is a combination of devices such as those disclosed herein.

In addition to a display 3832, computer system 3800 may include one or more other peripheral output devices 3834 including, but not limited to, an audio speaker, a printer, a storage device, and any combinations thereof. Such peripheral output devices may be connected to the bus 3840 via an output interface 3824. Examples of an output interface 3824 include, but are not limited to, a serial port, a parallel connection, a USB port, a FIREWIRE port, a THUNDERBOLT port, and any combinations thereof.

In addition or as an alternative, computer system 3800 may provide functionality as a result of logic hardwired or otherwise embodied in a circuit, which may operate in place of or together with software to execute one or more processes or one or more steps of one or more processes described or illustrated herein. Reference to software in this disclosure may encompass logic, and reference to logic may encompass software. Moreover, reference to a computer-readable medium may encompass a circuit (such as an IC) storing software for execution, a circuit embodying logic for execution, or both, where appropriate. The present disclosure encompasses any suitable combination of hardware, software, or both.

Those of skill in the art will appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by one or more processor(s), or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In accordance with the description herein, suitable computing devices include, by way of non-limiting examples, cloud computing platforms, distributed computing platforms, server clusters, server computers, desktop computers, laptop computers, notebook computers, sub-notebook computers, netbook computers, and netpad computers.

In some embodiments, the computing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smartphone operating systems include, by way of non-limiting examples, Nokia® Symbian® OS, Apple® iOS®, Research in Motion® BlackBerry OS®, Google® Android®, Microsoft® Windows Phone® OS, Microsoft® Windows Mobile® OS, Linux*, and Palm® WebOS®.

Non-transitory Computer Readable Storage Medium

In some embodiments, the platforms, systems, media, and methods disclosed herein include one or more non-transitory computer readable storage media encoded with a program including instructions executable by the operating system of an optionally networked computing device. In further embodiments, a computer readable storage medium is a tangible component of a computing device. In still further embodiments, a computer readable storage medium is optionally removable from a computing device. In some embodiments, a computer readable storage medium includes, by way of non-limiting examples, CD-ROMs, DVDs, flash memory devices, solid state memory, magnetic disk drives, magnetic tape drives, optical disk drives, distributed computing systems including cloud computing systems and services, and the like. In some cases, the program and instructions are permanently, substantially permanently, semi-permanently, or non-transitorily encoded on the media.

Computer Programs

In some embodiments, the platforms, systems, media, and methods disclosed herein include at least one computer program, or use of the same. A computer program includes a sequence of instructions, executable by one or more processor(s) of the computing device's CPU, written to perform a specified task. Computer readable instructions may be implemented as program modules, such as functions, objects, Application Programming Interfaces (APIs), computing data structures, and the like, which perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, a distributed computing resource, a cloud computing resource, or combinations thereof. In further various embodiments, a software module comprises a plurality of files, a plurality of sections of code, a plurality of programming objects, a plurality of programming structures, a plurality of distributed computing resources, a plurality of cloud computing resources, or combinations thereof. In various embodiments, the one or more software modules comprise, by way of non-limiting examples, a web application, a mobile application, a standalone application, and a distributed or cloud computing application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on a distributed computing platform such as a cloud computing platform. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for storage and retrieval of information, for example customer incident data. In various embodiments, suitable databases include, by way of non-limiting examples, relational databases, non-relational databases, object oriented databases, object databases, entity-relationship model databases, associative databases, XML databases, document oriented databases, and graph databases. Further non-limiting examples include SQL, PostgreSQL, MySQL, Oracle, DB2, Sybase, and MongoDB. In some embodiments, a database is Internet-based. In further embodiments, a database is web-based. In still further embodiments, a database is cloud computing-based. In a particular embodiment, a database is a distributed database. In other embodiments, a database is based on one or more local computer storage devices.

EXAMPLES

Example 1—Use of Transdermal Smart Patch to Treat Atrial Fibrillation

Atrial fibrillation is a direct cause of one in four strokes in people over age of 80. Current standard-of-care is to provide patients with daily oral doses of Rivaroxaban that prevent blood clots and reduce the risk of stroke. However, one in three patients miss their doses more than 80% of the time, leading to costly emergency department visits, hospital stays, rehab stays, and early dementia.

This example is to use transdermal smart patch incorporated with Rivaroxaban for treating patients with atrial fibrillation. In particular, an 80-year patient with chronic atrial fibrillation is provided with a 3-month supply of transdermal smart patches comprising twelve 7-day smart patches each with 35 mg of Rivaroxaban. Rivaroxaban is transferred by diffusion from the drug-containing layer of the smart patch to the patient's skin in a slow steady release over the 7-day period. During the use of the smart patch, the smart patch transmits its status via wireless communication through an IoT network to a cloud application.

At the end of day 7 of the treatment, the patient forgets to remove the exhausted smart patch and replace it with the next dose. The cloud application detects that the exhausted smart patch has not been removed and the next dose has not been applied and that the patient is non-compliant. A medical alert response center receives an alert on a computing device that this patient missed his regular dose. Accordingly, a trained operator at the medical alert response center dispatches an onsite nurse or family member to intervene on the forgetful patient's behalf, apply the next dose, and avoid the adverse consequences caused by missing the dose. The health care provider also receives a notification of the intervention for review and inclusion in the patient's medical record.

Example 2—Use of Transdermal Smart Patch to Treat Epilepsy and Other Seizure Disorders Epilepsy, also known as a seizure disorder, is a brain disorder that causes recurring seizures. It's estimated that 1 in 26 people develop the disorder, according to the Epilepsy Foundation. Epilepsy affects people of all genders, races, ethnic backgrounds, and ages. Patients with epilepsy and other seizure disorders are at constant risk of seizures that lead to falls and injuries, emergency room admissions, hospitalizations, and even death. A standard-of-care treatment is a daily oral dose of Perampanel to inhibit seizures onset. However, non-adherence is rampant—30% to 60%; missed doses are the leading cause of breakthrough seizures.

This example is to use transdermal smart patch incorporated with Perampanel for treating patients with Epilepsy. In particular, a 15-year-old female patient with Epilepsy is on a daily 2 mg oral dose of Perampanel. Even though she understands the importance of taking her daily dosage, with her busy and everchanging schedule of teenage activities, she regularly forgets to take her dose. As a result, she is experienced with having dangerous seizure episodes. The patient changes from a daily oral dose to a 7-day transdermal smart patch containing 14 mg of Perampanel. Perampanel is transferred by diffusion from the drug-containing layer of the smart patch to the patient's skin steadily and continuously for 7 days. During the use of the smart patch, the patient uses her Apple watch to track drug compliance and connect with her parents and health care providers via a wireless network. Instead of having to remember to take an oral dose every day, she can be at ease knowing she is being dosed continuously for an entire week at which point her Apple watch will remind her to remove the exhausted smart patch and apply the next one.

On the third day of a smart patch dosage, the female patient accidentally lost her smart patch when she was playing lacrosse with her friends. The patient's mobile device transmits the patient's smart patch usage data indicating the non-compliance to the wireless network. Her parents and a medical alert response center receive an alert on their computers and mobile phones that this patient's dosage has been terminated early. Accordingly, the medical alert response center sends out an alert to the patient's mobile device and reminds the patient to comply with the treatment. Her parents immediately contact the lacrosse coach at school to make sure the transdermal smart patch is reapplied, thereby avoiding adverse consequences caused by missing the dose. The health care provider also receives a notification of the intervention for review and inclusion in the patient's medical record.

Example 3—Use of Transdermal Smart Patch to Treat Schizophrenia and Bipolar Disorder Schizophrenia is a mental disorder characterized by continuous or relapsing episodes of psychosis. Major symptoms include hallucinations (typically hearing voices), delusions, and disorganized thinking. Other symptoms include social withdrawal, decreased emotional expression, and apathy. About 0.3% to 0.7% of people are diagnosed with schizophrenia during their lifetime. Symptoms typically appear from late adolescence to the early 20s in males and in the late 20s to mid-30s in females.

Bipolar disorder is another mental disorder characterized by periods of depression and periods of abnormally elevated mood that each last from days to weeks. Some people with bipolar disorder also experience symptoms of psychosis. Statistics from the National Institute of Mental Health (NIMH) Trusted Source suggest that approximately 2.8% of U.S. adults experience bipolar disorder in a given year and 4.4% experience it at some point in their lives. Symptoms of bipolar disorder usually start to appear around age 25, and the condition affects males and females equally.

Patients with schizophrenia, bipolar disorder, or other mental disorders require ongoing medications to stabilize their disease. The consequences of missing a dose include psychotic episodes that lead to emergency department admissions, hospitalizations, and even loss of housing. Restarting a drug regimen after a period of missed doses can take weeks to restabilize the patient. Olanzapine is one common and effective antipsychotic drug that is delivered as a once daily oral tablet. Over half of psychotic patients are non-adherent despite the profoundly negative consequences.

This example is to use transdermal smart patch incorporated with Olanzapine for treating patients with Schizophrenia. In particular, a 45-year-old male patient with schizophrenia is provided with a transdermal smart patch comprising 70 mg of Olanzapine for 7 days. Olanzapine is transferred by diffusion from the drug-containing layer of the smart patch to the patient's skin. During the use of the smart patch, the patient uses his tablet to track drug compliance and connect with health care providers via a wireless network.

On day 4 of the treatment, the male patient rips off his transdermal smart patch as a voice in his head tells him that there is no medicine in the smart patch left. The patient's mobile device transmits the patient's smart patch usage data indicating the non-compliance to the wireless network. A medical alert response center receives an alert on their computer that this patient missed his regular dose. Accordingly, a trained operator at the medical alert response center sends out an alert to the patient's mobile device to remind the patient to comply with the treatment and also sends out a message to the caregiver to check on the patient as he has a history of severe hallucinations. His caregiver immediately goes to the patient's house to intervene. The caregiver puts the smart patch back on the patient assuring him there is medicine in the smart patch, thereby avoiding adverse consequences caused by missing the dose.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations, or equivalents. It is intended that the following claims define the scope of the invention and that methods and structures within the scope of these claims and their equivalents be covered thereby.

What is claimed is:

1. A transdermal drug delivery smart patch comprising, in and/or on the transdermal drug delivery smart patch:
   a drug-containing layer;
   a communication interface;
   one or more sensors configured to detect a status change of the smart patch, the status change comprising one or more of (i) removing a packaging from the smart patch, (ii) removing a liner from an adhesive layer of the smart patch, (iii) applying the smart patch to the skin of the patient, or (iv) removing the smart patch from the skin of the patient; and
   a processor communicatively coupled to the one or more sensors and the communication interface, wherein the processor is configured to perform operations comprising:
   (a) automatically transiting between a plurality of working conditions based on the status change of the smart patch, wherein the plurality of working conditions of the smart patch comprises a hibernation mode, a sleep mode, and a work mode, and wherein the smart patch does not send out or receive communication signals in the hibernation mode, and
   (b) transmitting smart patch status data using the communication interface.

2. The transdermal drug delivery smart patch of claim 1, wherein the one or more sensors comprise a light sensor, a resistive sensor, or both.

3. The transdermal drug delivery smart patch of claim 1, wherein the smart patch is disposable.

4. The transdermal drug delivery smart patch of claim 1, wherein the smart patch sends data wirelessly, or receives data wirelessly, or both.

5. The transdermal drug delivery smart patch of claim 1, wherein the one or more sensors detect information concerning the smart patch status data.

6. The transdermal drug delivery smart patch of claim 1, further comprising a flex circuit in electrical connection with the one or more sensors, the flex circuit comprising one or more conducting pads.

7. The transdermal drug delivery smart patch of claim 6, wherein the one or more sensors detect an electrical signal change between the liner and the conducting pads on the flex circuit when the liner is removed.

8. The transdermal drug delivery smart patch of claim 6, wherein the one or more sensors detect an electrical signal change between the conducting pads on the flex circuit and the skin when the smart patch is applied to the skin.

9. The transdermal drug delivery smart patch of claim 1, wherein the processor controls the smart patch to transit (i) between the work mode and the sleep mode based on data input from the one or more sensors, a wirelessly received communication signal, or both or (ii) between the hibernation mode and the work mode or the sleep mode based on data input from the one or more sensors.

10. The transdermal drug delivery smart patch of claim 1, wherein the one or more sensors comprise an optical sensor that detects light change in response to the status change of the smart patch.

11. The transdermal drug delivery smart patch of claim 1, wherein the processor determines a current state of the smart patch based on a state of the one or more sensors, a sequence of state changes and a timing of each state change.

12. The transdermal drug delivery smart patch of claim 1, wherein the processor wirelessly transmits the current state of the smart patch, a smart patch identifier, or both.

13. The transdermal drug delivery smart patch of claim 1, wherein the processor determines drug compliance of the patient based at least in part on the smart patch usage data.

14. The transdermal drug delivery smart patch of claim 1, wherein the communication interface wirelessly transmits data to one or more user devices to generate an alert, a reporting message, or an intervention message, or any combination thereof, concerning the drug compliance of the patient.

15. The transdermal drug delivery smart patch of claim 14, wherein the communication interface transmits data to the one or more user devices using a communication protocol selected from the group consisting of Bluetooth®, Bluetooth® Low Energy (BLE), Wi-Fi, Zigbee, Z-Wave®, LoRa®, near field communications (NFC), broadband, NarrowBand-Internet of Things (NB-IoT), Radio Frequency Identification System (RFID), WLAN, cellular signaling, or future revisions thereof.

16. A computer-implemented method for enhancing drug compliance of a patient in need thereof, the method comprising:
(a) receiving from one or more sensors of a transdermal drug delivery smart patch information associated with a plurality of working conditions of the smart patch, the plurality of working conditions comprising a hibernation mode, a sleep mode, and a work mode, wherein the smart patch comprises, in and/or on the smart patch, a drug-containing layer, a communication interface, the one or more sensors, and a processor;
(b) generating smart patch usage data based on the plurality of working conditions of the smart patch, wherein the smart patch usage data comprises at least one of a smart patch status, a dose of a drug administered to the patient, a timing of the dose, or a frequency of doses, and wherein the smart patch status comprises one or more of (i) removing a packaging from the smart patch, (ii) removing a liner from an adhesive layer of the smart patch, (iii) applying the smart patch to the skin of the patient, or (iv) removing the smart patch from the skin of the patient;
(c) automatically transiting between the plurality of working conditions based on a change in the smart patch status, wherein the smart patch does not send out or receive communication signals in the hibernation mode; and
(d) determining drug compliance of the patient based on the smart patch status data and a medical record of the patient transmitted over a network.

17. The method of claim 16, wherein the medical record comprises one or more of a prescription information, an expected dosage of the drug, or an expected timing of administering the drug.

18. The method of claim 16, further comprising generating an alert, a reporting message, or an intervention message of the drug compliance.

19. The method of claim 16, further comprising determining the drug compliance of the patient by comparing an individual value measured by the one or more sensors of the smart patch to an average value of sensor inputs of the smart patch.

20. A non-transitory computer readable medium comprising machine executable instructions that, when executed by one or more processors, implement a method to enhance drug compliance of a patient in need thereof, the method comprising:
(a) receiving from one or more sensors of a transdermal drug delivery smart patch information associated with a plurality of working conditions of the smart patch, the plurality of working conditions comprising a hibernation mode, a sleep mode, and a work mode, wherein the smart patch comprises, in and/or on the smart patch, a drug-containing layer, a communication interface, the one or more sensors, and a processor;
(b) generating smart patch usage data based on the plurality of working conditions of the smart patch, wherein the smart patch usage data comprises at least one of a smart patch status, a dose of a drug administered to the patient, a timing of the dose, or a frequency of doses, and wherein the smart patch status is based on one or more of (i) removal of a packaging from the smart patch, (ii) removal of a liner from an adhesive layer of the smart patch, (iii) application of the smart patch to the skin of the patient, or (iv) removal of the smart patch from the skin of the patient;
(c) automatically transiting between the plurality of working conditions based on a change in the smart patch status, wherein the smart patch does not send out or receive communication signals in the hibernation mode; and
(d) determining drug compliance of the patient based on the smart patch status data and a medical record of the patient.

\* \* \* \* \*